United States Patent [19]

Barth

[11] Patent Number: 4,797,394

[45] Date of Patent: Jan. 10, 1989

[54] 6-(1-CARBAMOYL-1-HYDROXYMETHYL)-PENICILLANIC ACID DERIVATIVES

[75] Inventor: Wayne E. Barth, East Lyme, Conn.

[73] Assignee: Pfizer Inc., New York, N.Y.

[21] Appl. No.: 85,675

[22] PCT Filed: Oct. 29, 1985

[86] PCT No.: PCT/US85/02134

§ 371 Date: Jun. 5, 1987

§ 102(e) Date: Jun. 5, 1987

[51] Int. Cl.[4] .................. C07D 499/00; A61K 31/425
[52] U.S. Cl. ..................... 514/192; 514/195; 540/310
[58] Field of Search ................. 540/310; 514/192, 195

[56] References Cited

U.S. PATENT DOCUMENTS

| 4,272,439 | 6/1981 | Ganguly et al. | 260/245.2 R |
|---|---|---|---|
| 4,283,531 | 8/1981 | Ganguly et al. | 544/30 |
| 4,478,748 | 10/1984 | Barth | 260/245.2 R |
| 4,488,994 | 12/1984 | Bigham | 260/239.1 |
| 4,502,990 | 3/1985 | Barth | 260/245.2 R |
| 4,503,040 | 3/1985 | Barth | 424/114 |
| 4,590,073 | 5/1986 | Barth | 424/114 |
| 4,613,462 | 9/1986 | Barth | 540/310 |
| 4,738,959 | 4/1988 | Cooke et al. | 540/310 |

FOREIGN PATENT DOCUMENTS

| 2053220 | 2/1981 | United Kingdom . |
| 2122619 | 1/1984 | United Kingdom . |

OTHER PUBLICATIONS

Sheehan, J. Antibiotics Japan, vol. 37, pp. 1441–1448, 1984.

*Primary Examiner*—Nicholas S. Rizzo
*Attorney, Agent, or Firm*—Peter C. Richardson; J. Trevor Lumb; Robert K. Blackwood

[57] ABSTRACT

6-(1-Carbamoyl-1-hydroxymethyl)penicillanic acid derivatives are useful as antibacterials and/or beta-lactamase inhibitors.

86 Claims, No Drawings

6-(1-CARBAMOYL-1-HYDROXYMETHYL)-PENICILLANIC ACID DERIVATIVES

BACKGROUND OF THE INVENTION 6-(1-Carbamoyl-1-hydroxymethyl)penicillanic acid derivatives, having the partial structure

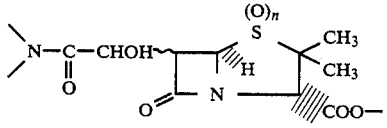

wherein n is 0, 1 or 2, are generally useful as antibacterials and/or beta-lactamase inhibitors. Some of these compounds possess excellent antibacterial activity per se, and so are valuable as industrial or medicinal antibacterial agents in their own right. Additionally, and more generally, they have particular value as beta-lactamase inhibitors; as such, they are useful in combination with conventional beta-lactam antibiotics (penicillins and cephalosporins) against microorganisms resistant or partially resistant to beta-lactam antibiotics through production of beta-lactamase enzymes.

beta-Lactamase inhibiting 6-(1-hydroxyalkyl)penicillanic acid 1,1-dioxides (sulfones) and 3-carboxylate esters thereof have been reported by Kellogg (U.S. Pat. Nos. 4,287,181; 4,342,768; European Pat. Publication No. 83977), while 6-(aminoacyloxymethyl)penicillanic acid 1,1-doxides have been reported by Barth (U.S. Pat. No. 4,503,040). Various antibacterial 6-(1-hydroxyalkyl)penicillanic acids and their 1-oxides (sulfoxides) have been disclosed by Beattie et al., (U.S. Pat. No. 4,207,323), but that disclosure encompasses no compounds containing the key 6-(1-carbamoyl-1-hydroxyalkyl)substituent of the present invention.

U.K. Patent Application No. 2,053,220 broadly discloses beta-lactamase inhibiting compounds of the formula

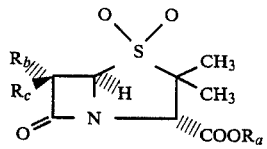

The definitions of $R_a$, $R_b$ and $R_c$ define literally an infinite number of compounds. Said infinity of compounds proposed might be construed to encompass some of the 1,1-dioxide compounds of the present invention. However, there is no specific mention of or preparative method provided for any compounds of the type of the present invention, let alone any hint or suggestion that the present compounds represent preferred compounds, having potent antibacterial and/or beta-lactamase inhibitory activity.

Sheehan et al. [J. Antibiotics Japan, vol. 37, pp. 1441-1448 (1984)] have reported that 6-[1-(N-phenylcarbamoyl)methyl]penicillanic, a compound lacking the present 1-hydroxy group, possesses only limited Gram-positive activity and no Gram-negative activity. Sheehan et al. do not list the latter compound among those having a modicum of beta-lactamase inhibitory activity.

SUMMARY OF THE INVENTION

The present invention is concerned with antibacterials, beta-lactamase inhibitors and/or intermediates containing the following partial structure:

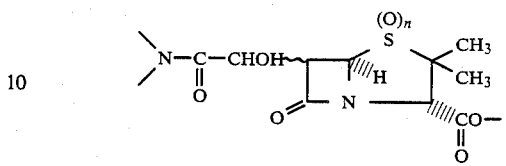

wherien n is 0, 1 or 2. Because of their excellent activity, the present invention is particularly concerned with antibacterial and/or beta-lactamase inhibitory compounds having the formula

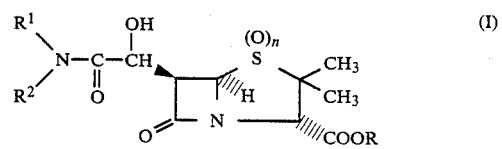

wherein
n is 0, 1 or 2;

R is hydrogen, a radical group forming an ester hydrolyzable under physiological conditions, or an acyloxymethyl or 1-(acyloxy)ethyl radical derived from a conventional beta-lactam antibiotic; and $R^1$ and $R^2$ are taken separately and are each independently hydrogen, $(C_1-C_7)$alkyl, phenyl, $(C_7-C_{12})$phenylalkyl, $(C_3-C_7)$cycloalkyl, naphthyl, or

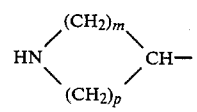

where m is 1 or 2 and p is 2 or 3; or one of said groups substituted on aliphatic, aromatic or heterocyclic carbon with $(C_1-C_4)$alkyl, phenyl, hydroxy, hydroxymethyl, 2-hydroxyethyl, $(C_1-C_4)$alkoxy, $(C_2-C_5)$alkanoyloxy, carbamoyloxy, formamido, $(C_2-C_5)$ alkanecarboxamido, $(C_1-C_4)$alkanesulfonamido,

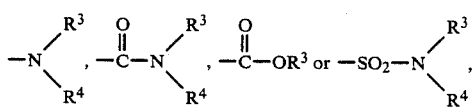

on heterocyclic nitrogen with $(C_1-C_4)$alkyl, phenyl, $(C_7-C_9)$phenylalkyl, pyridyl, 2-hyroxyethyl, formyl, $(C_2-C_5)$alkanoyl or

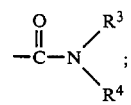

$R^1$ and $R^2$ are taken together with the nitrogen to which they are attached to form a pyrrolidine, piperidine, perhydroazepine, morpholine, piperazine, homopiperazine, indoline, isoindoline, 1,2,3,4-tetrahydroquinoline, 1,2,3,4-tetrahydroisoquinoline or

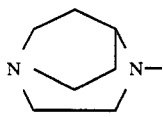

(1,4-diazabicyclo[3.2.2]non-4-yl) ring system; or one of said ring systems substituted on aliphatic, aromatic or heterocyclic carbon with $(C_1-C_4)$alkenyl, phenyl, hydroxy, hydroxymethyl, 2-hydroxyethyl, $(C_1-C_4)$alkoxy, $(C_2-C_5)$alkanoyloxy, carbamoyloxy, formamido, $(C_2-C_5)$alkanecarboxamido, $(C_1-C_4)$alkanesulfonamido,

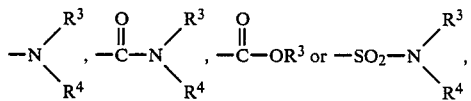

on heterocyclic nitrogen with $(C_1-C_4)$alkenyl, phenyl, $(C_7-C_9)$phenylalkyl, pyridyl, 2-hydroxyethyl, formyl, $(C_2-C_5)$alkanoyl or

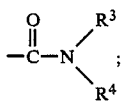

$R^3$ and $R^4$ are taken separately and are each hydrogen, $(C_1-C_4)$alkyl or phenyl; or $R^3$ and $R^4$ are taken together with the nitrogen to which they are attached to form a pyrrolidine, piperidine, morpholine, or 4-[$(C_1-C_3)$alkyl or phenyl]piperazine ring; with the provisos that in said group $-NR^1R^2$ (a) there is no tetrahedral carbon atom which is simultaneously bonded to two of the same or different atoms selected from the group consisting of nitrogen, oxygen and sulfur and (b) when both of $R^1$ and $R^2$ are other than hydrogen, then the carbons of $R^1$ and $R^2$ which are adjacent to the nitrogen branch point are substituted with a total of at least two hydrogens;

a pharmaceutically acceptable cationic salt when the compound contains a carboxylic acid group; or a pharmaceutically acceptable acid addition salt when the compound contains a basic nitrogen atom.

Preferred compounds are those which are readily prepared and show a high level of the desired activity.

When $R^1$ and $R^2$ are taken separately, the preferred values are each independently hydrogen, $(C_1-C_4)$alkyl, $(C_5-C_6)$cycloalkyl, phenyl, benzyl or one of said groups substituted by methyl, hydroxy, $(C_1-C_2)$alkoxy, $-COOR^3$, or $-CONR^3R^4$. When n is 0, most preferred are $R^1$ as methyl or ethyl with $R^2$ as methyl, ethyl, phenyl or benzyl; $R^1$ as benzyl and $R^2$ as $-CH_2CONHCH_3$; and $R^1$ as ethyl and $R^2$ as 3-hydroxyphenyl. When n is 1, $R^1$ and $R^2$ as each methyl with the 1-oxide in the beta-configuration is most preferred. When n is 2, most preferred are $R^1$ as methyl with $R^2$ as methyl, phenyl or cyclohexyl.

When $R^1$ and $R^2$ are taken together with the nitrogen to which they are attached, the preferred ring systems are pyrrolidine, piperidine, perhydroazepine, morpholine, 4-[$(C_1-C_4)$alkyl, phenyl, benzyl, pyridyl or 2-hydroxyethyl]piperazine, indoline, isoindoline, 1,2,3,4-tetrahydroquinoline or 1,2,3,4-tetrahydroisoquinoline ring system, or one of said ring systems substituted by methyl, hydroxy, hydroxymethyl, carboxy, carbamoyl, $-COOR^3$ or $-CONR^3R^4$. When n is 0, most preferred are $R^1R^2N-$ as piperidino, perhydroazepin, 1,2,3,4-tetrahydroisoquinolino, isoindolino and indolino. When n is 1 $R^1R^2N-$ as pyrrolidino with the 1-oxide in the alpha configuration is most preferred. When n is 2, most preferred is $R^1R^2N-$ as piperidino, 4-hydroxypiperidino or 4-phenylpiperidino.

In all cases, the most preferred compounds further have the 1-hydroxy substituted carbon of the side chain in the S-configuration:

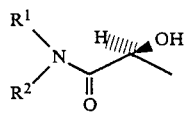

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid. The more preferred ester forming radicals are those wherein R is: (5-methyl-1,3-dioxol-2-on-4-yl)methyl; 1H-isobenzofuran-3-on-1-yl; gamma-butyrolacton-4-yl; $-CHR^5OCOR^6$; or $-CHR^5OCOOR^7$;

wherein $R^5$ is hydrogen or methyl; $R^6$ is $(C_1-C_6)$alkyl, $(C_1-C_6)$carboxalkyl, carboxycyclohexyl or carboxyphenyl; and $R^7$ is $(C_1-C_6)$alkyl. The most preferred radicals are pivaloyloxymethyl and 1-(ethoxycarbonyloxy)ethyl.

The reference to an acyloxymethyl or 1-(acyloxy)ethyl ester derived from a conventional beta-lactam antibiotic refers to a mixed methanediol or 1,1-ethanediol ester of the formula (I) wherein R is derived from one of the standard, well known beta-lactam antibiotics containing a carboxylic acid group on the carbon alpha to the beta-lactam ring nitrogen, i.e., R is a group

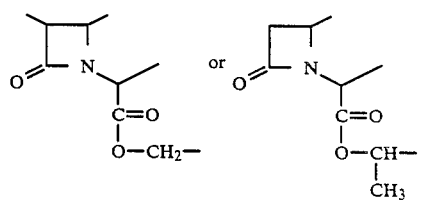

Preferred esters of this class are those wherein R is:

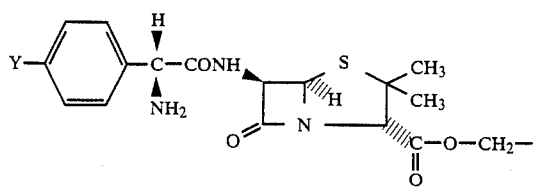

(A)

wherein Y is hydrogen or hydroxy.

The present invention also encompasses a pharmaceutical composition for treating bacterial infections which comprises in a weight ratio of 10:1 to 1:3 a conventional beta-lactam antibiotic and a compound of the formula (I) wherein $R^1$ is hydrogen or a radical group forming an ester which is hydrolyzable under physiological conditions. For this composition, preferred compounds of the formula (I) are defined above. Preferred beta-lactam antibiotics are penicillins or cephalosporins of established clinical utility, viz., amoxicillin, ampicillin, apalcillin, azlocillin, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefbuperazone, cefmenoxime, cefonicid, cefodizime, cefoperazone, ceforanide, cefotaxime, cefotiam, cefoxitin, cefpimazole, cefpiramide, cefpirome, cefsulodin, ceftazidime, ceftizoxime, ceftriaxone, cefuroxime, cephacetrile, cephalexin, cephaloglycin, cephaloridine, cephalothin, cephapirin, cepharidine, cyclacillin, epicillin, furazlocillin, hetacillin, lenampicillin, levopropylcillin, mecillinam, mezlocillin, penicillin G, penicillin V, phenethicillin, piperacillin, pivampicillin, sarmoxicillin, sarpicillin, suncillin, talapicillin and ticarcillin, including the pharmaceutically acceptable salts thereof. The names employed for these beta-lactams are generally USAN, i.e., U.S. Adopted Names.

Also preferred are combinations of the beta-lactamase inhibitors of the invention with 7-[D-(2-[4-carboxy-5-imidazolecarboxamido])-2-phenylacetamido]-3-[4-(2-sulfonatoethyl)pyridinium]-3-cephem-4-carboxylic acid or azetreonam.

The present invention further encompasses a method of treating a bacterial infection in a mammal by topical, oral or parenteral administration of an antibacterially effective amount of a pharmaceutical composition of the preceding paragraphs; a pharmaceutical composition comprising an antibacterially effective amount of a compound of the formula (I) per se, and a method of treating bacterial infections with an antibacterially effective amount of a compound of the formula (I) per se.

The present invention also encompasses intermediate compounds as follows:

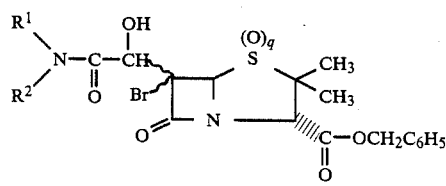

(II)

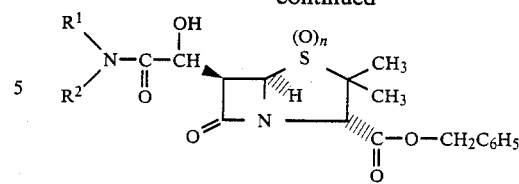

(III)

wherein q is 0 or 2 and n, $R^1$ and $R^2$ are generally as defined above, but with the further proviso that when said group $-NR^1R^2$ contains a substituent $-NH$ or $-NH_2$ group which is more reactive toward cyclic anhydride than the $R^1R^2NH$ nitrogen, said substituent $-NH$ or $-NH_2$ group is protected by a benzyloxycarbonyl group.

Particularly when compounds of the formula (II) are prepared by a Grignard reaction employing a compound of the formula

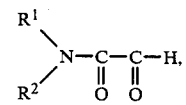

said compound and derived compounds of the formula (II) and (III) will generally have phenolic hydroxy and carboxy groups protected by a benzyl group, i.e., as the corresponding benzyl ether or benzyl ester, respectively.

Finally, the present invention encompasses compounds of the formula

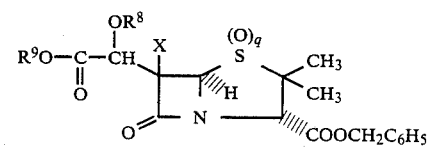

wherein
q is 0 or 2;
$R^8$ and $R^9$ are taken separately and $R^8$ is hydrogen and $R^9$ is allyl, or $R^8$ and $R^9$ are taken together and are

and
X is hydrogen or bromo;
with the proviso that when X is hydrogen, it is of 6-alpha configuration.

The preferred intermediates of this class are:

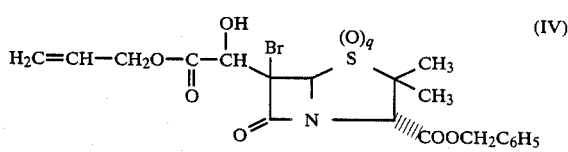

(IV)

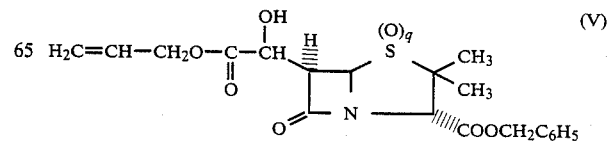

(V)

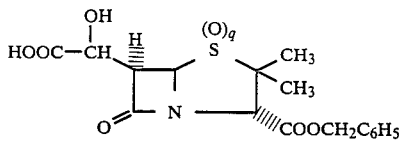

and

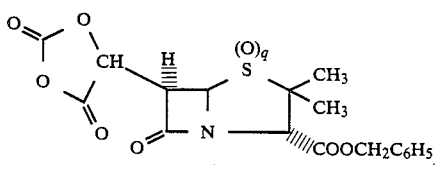

Most preferred of these of the formulas (IV), (V), (VI) and (VII) are those wherein q is 0. The preferred configuration for the side chain in these compounds is

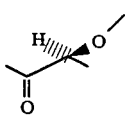

which is the S-configuration in the case of compounds (V), (VI) and (VII) and the R-configuration in the case of compound (IV).

DETAILED DESCRIPTION OF THE INVENTION

The compounds of the formula (I) are preferably prepared by the following synthetic routes:

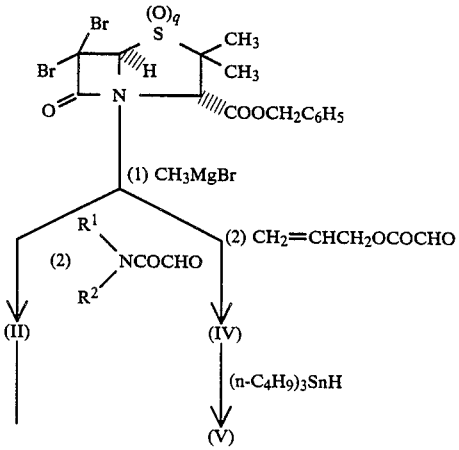

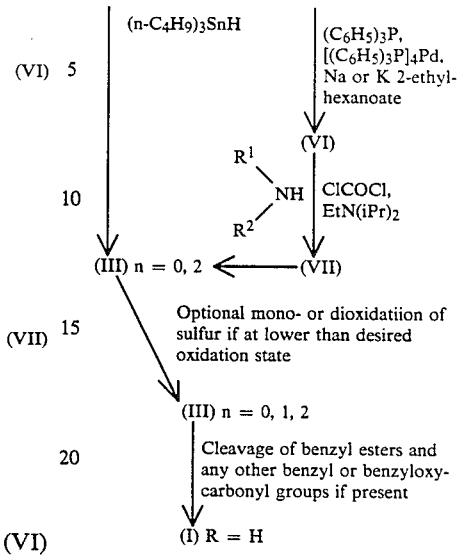

Variations in this sequence, e.g., cyclic anhydride formation and amide formation prior to debromination, will be readily evident to those skilled in the art. To make compounds wherein the group $R^1R^2N-$ contains a basic $-NH_2$ of $>NH$ function, it is preferred to use the cyclic anhydride (VII). It is similarly preferred to make compounds wherein the group $R^1R^2N-$ contains acidic OH groups (particularly phenolic or carboxylic acid groups) via the cyclic anhydride (VII). Alternatively, the latter groups are protected as benzyl ethers or esters, respectively, in the reaction of the Grignard reagent with the glyoxamide.

In the first stage of the above synthetic route, the known dibromo compound (VIII) is dissolved in a dry, reaction-inert solvent such as tetrahydrofuran or toluene, which will remain liquid at the reaction temperature, cooled to $-50°$ to $-100°$ C., and reacted with substantially one molar equivalent of a Grignard reagent such as methylmagnesium bromide in an ethereal solvent such as diethyl ether (said reagent formed by standard methods in the laboratory, or purchased commercially), generally added portionwise over a 5–15 minutes while maintaining the same low reaction temperature. After stirring for 10–30 minutes to allow complete reaction and equilibration, the glyoxylate amide or ester,

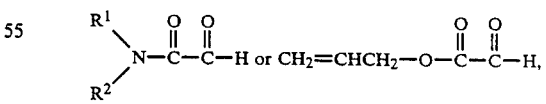

is added, optionally dissolved in the same or another reaction inert solvent, in like manner. After stirring 10 minutes–1 hour at the same low temperature, the reaction mixture is quenched with a weak acid such as acetic acid or an acidic salt such as ammonium chloride, and product isolated by standard methods such as evaporation, extraction and chromatography, including optical chromatographic separation of epimers corresponding to R- and S- side chain configurations:

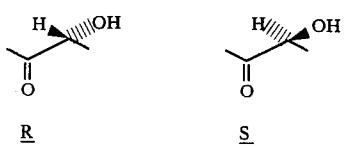

where stability and differences in polarity permit.

As used here and hereinafter, the expression "reaction-inert solvent" refers to any solvent which does not interact with starting materials, reagents, intermediates or products in a manner which significantly reduces the yield of the desired product.

When the allyl esters of the formula (IV) are prepared, the required allyl glyoxylate is preferably prepared according to specific methods detailed below. When the amides of the formula (II) are prepared, the required glyoxylate amides are generally prepared by lead tetraacetate oxidation of the corresponding bis-amide of tartaric acid, as specifically exemplified below. The tartrate bis-amides are in turn available from tartaric acid and its reactive diesters (e.g. dimethyl tartrate) and amines by standard methods.

The C.6 stereochemistry of the intermediates of the formulas (II) and (IV) has not been determined and is therefore not specified. However, C.6 stereochemistry becomes fixed as 6-beta in (III) and (V) during the tributyltin hydride debromination step, regardless of stereochemistry at the 6-position in the precursor. The debrominaton step is optionally carried out in the presence of small amounts of free radical initiator such as 2,2'-azobisisobutyronitrile (AIBN), in a reaction inert solvent such as benzene or toluene. The temperature is usually elevated (e.g., 60°-100° C.), such that reaction occurs in a reasonable period of time, but not so high as to cause undue thermal degradation. Products are once again recovered and purified by standard methods, as noted above, with chromatographic separation of R- and S-sidechain epimers alternatively carried out at this stage.

When the allyl ester (V) is employed as intermediate, it is converted to the acid (VI), conveniently by reaction with substantially one molar equivalent of sodium or potassium ethylhexanoate (or other lipophilic carboxylate salt) in the presence of catalytic amount of tetrakis(triphenylphosphine)palladium (typically 5 mole %) and triphenylphosphine (typically 20-25 mole %) in a reaction inert solvent, preferably one in which the reactants are soluble and the alkali metal salt of the desired product is relatively insoluble. Particularly well suited in the present instance is the sodium salt of 2-ethylhexanoate in ethyl acetate as solvent. In this case the salt is fully precipitated by addition of a lipophilic solvent such as ether.

Temperature is not critical in this deprotection step, e.g., 0°-50° C. is usually satisfactory. Most conveniently, ambient temperature is employed. If desired, the salt is converted to the free acid form, during or after isolation, by standard methods, e.g., acidification of an aqueous solution of the salt, with extraction of the free acid into a water immiscible organic solvent.

The acid compound (VI), conveniently in the form of its sodium salt, is readily converted to the cyclic anhydride (VII) by the action of substantially one molar equivalent of phosgene, in a reaction inert solvent such as tetrahydrofuran or carbon tetrachloride. If desired, the anhydride is isolated, e.g., by simple stripping of solvent from the reaction. Alternatively, and preferably, the solution of anhydride, with at least 1 (usually 2) molar equivalents of a tertiary amine such as diisopropylethylamine added to neutralize by-product HCl, is used directly in the next step.

In the next stage, the anhydride with or without isolation, is reacted with an amine, $R^1R^2NH$, to form the intermediate 6-(1-carbamoyl-1-hydroxymethyl)penicillanate of the formula (III), in the same, or another reaction inert solvent such as tetrahydrofuran, methylene dichloride or, when the amine is highly reactive, even $H_2O$. Temperature is not critical, but will generally be in the range $-25°$ to $50°$ C. With highly reactive amines such as $NH_3$, temperatures lower in this range are preferred, while with less reactive amines, such as N-benzylaniline, temperatures higher in the range can be beneficial. In general, ambient temperatures are perfectly satisfactory. At least 1 molar equivalent of the amine is employed, although an excess, up to 3 or 4 molar equivalents, is beneficially used when the amine is relatively unreactive, particularly when the amine is readily available. According to the present invention, the present products of the formula (I) can contain a substituent primary or secondary amine function in the group $R^1R^2N—$. When that amine substituent is more reactive towards the cyclic anhydride than amino group $R^1R^2NH$, it is strongly preferred to protect that more reactive amine as its benzyloxycarbonyl derivative (readily prepared by reaction with one equivalent of benzyloxycarbonyl chloride). For example, when $R^1$ is ethyl and

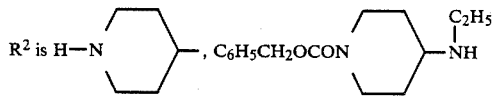

is employed as the reactant. Just to the contrary, when the amine substituent is unreactive or less reactive than the group $R^1R^2NH$, it is preferred to simply react the unprotected diamine with the cyclic anhydride. For example, when $R^1R^2N—$ is $(CH_3)_3CnHCH_2CH_2N(CH_3)—$, $(CH_3)_2CHNHCH_2CH_2NH—$, $(CH_3)_2CHNHCH(CH_3)CH_2NH—$, $(C_6H_5)NHCH_2CH_2NH—$ or

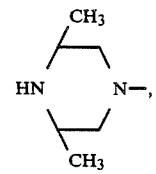

it is preferred to react the unprotected amine directly with the anhydride, thereby avoiding the unnecessary and generally difficult steps of protecting the less reactive amine function of a diamine.

The amines required for the present syntheses are readily available. They are known from the prior art, frequently available from commercial sources, or are prepared by methods analogous to those found in the prior art.

If 1-oxide or 1,1-dioxide is desired, and sulfur is not already in the desired oxidation state, the sulfur is oxidized at this stage in the synthetic sequence. In order to avoid unduly complex mixtures when the 1-oxides (sulfoxides) are desired, said oxidation is preferably carried out on separated R- or S-sidechain epimers. To form a mixture of the 1-alpha-oxide (S→O) and 1-beta-oxide (S⫶O) of the formula (III) wherein n is 1, the corresponding sulfides (III, n=0) are oxidized with substantially 1 molar equivalent of a peracid, conveniently m-chloroperbenzoic acid, in a reaction-inert solvent such as methylene chloride or ethyl acetate, at 0°–50° C., conveniently at ambient temperatures. The resulting mixture is isolated by standard methods such as extraction, evaporation, crystallization and chromatography, including chromatographic separation of the 1-alpha and 1-beta-oxides at this or a later stage of the synthetic sequence, as desired. To form the 1,1-dioxide (sulfone) of the formula (II) wherein n=2, the sulfide is oxidized with at least two molar equivalents of the peracid, otherwise under conditions and with isolation as described above for sulfoxides.

In the final stage of the synthesis of the compounds (I) wherein R is hydrogen, the C.2 benzyl ester group, together with any other benzyl ester, benzyl ether or N-benzyloxycarbonyl group, is removed by hydrogenolysis using methods generally known in the penicillin art. The substrate, in a reaction-inert solvent, is contacted with hydrogen in the presence of a noble metal catalyst, such as palladium, platinum or rhodium, optionally in the form of its oxide or a salt, or on a carrier such as carbon, an alkaline earth carbonate or alumina. Temperature is not critical (e.g. 0°–50° C.), but is preferably 25° C. or lower in order to minimize thermal degradation. Pressure can be varied over a wide range (subatmospheric to 100 atmospheres), but as a matter of convenience will generally be in the range of 1 to 7 atmospheres. The reaction inert solvent is preferably relatively low boiling so as to be readily removed by concentration in vacuo. Aqueous tetrahydrofuran is a solvent particularly well-suited for the present purpose. The preferred catalyst is palladium, supported on carbon. It is further preferred to carry out the hydrogenation in the presence of substantially one equivalent of sodium bicarbonate. Following recovery of the catalyst, tetrahydrofuran is stripped away and the aqueous residue freeze dried to directly yield the sodium salt of the product. If the free acid then is desired, it is obtained by standard methods from the salt, e.g., dissolution in water, acidification, extraction into a solvent such as ethyl acetate, and stripping the solvent away.

Other pharmaceutically-acceptable cationic salts of the present invention are also readily prepared by standard methods. For example, an equivalent of the corresponding cationic hydroxide, carbonate or bicarbonate, or of an amine, is combined with the carboxylic acid in an organic or aqueous solvent, preferably at reduced temperature (e.g., 0°–5° C.), with vigorous agitation and slow addition of the base. The salt is isolated by concentration and/or the addition of a non-solvent. Alternatively, other cationic salts are isolated directly from hydrogenolysis reaction mixtures by replacing the above sodium bicarbonate with an equivalent amount of the appropriate base.

Likewise pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. As noted above for the sodium salt, the acid addition salts are alternatively isolated directly from hydrogenolysis reaction mixtures, i.e., without isolation of the free amine, otherwise using similar techniques.

The compounds of the formula (I) wherein R represents an in vivo hydrolyzable ester are prepared from the corresponding free acids or cationic salts according to known method, readily identified by those skilled in the penicillin art (see for example U.S. Pat. Nos. 3,951,954, 4,234,579; 4,287,181; 4,342,693; 4,452,796; 4,342,693; 4,348,264; 4,416,891; and 4,457,924). A preferred method of preparation is exemplified below. If desired, an ester containing a basic amine or carboxylic acid function is converted to an acid addition salt or cationic salt, respectively, according to the methods of the immediately preceding paragraphs.

Conjugate diesters of the above formula (I) wherein R is an acylmethyl or 1-acylethyl radical derived from a conventional penicillin are conveniently made from a salt (preferably the tetrabutylammonium salt) of the corresponding compound of the formula (I) wherein R is hydrogen, and the halomethyl ester (preferably the iodomethyl ester) of the penicillin, in protected form when the penicillin contains primary or secondary amino or carboxylic acid functionality. The preferred protecting groups are those removed by hydrogenolysis, particularly the benzyloxycarbonyl group removed by hydrogenolysis under the conditions detailed above. Alternatively, azido groups are used in place of the desired amino groups in the precursor penicillin moiety. The azido group is hydrogenated to the amino group under those same conditions. Exemplary is the preparative route for compounds of the formula (I) wherein R is in the form of the preferred radical of the formula (A) defined above. If not already in hand, the requisite N-benzyloxycarbonyl, ampicillin or azidocillin is first converted to its idomethyl ester by known methods. The latter is in turn reacted with a cationic salt of the compound (I) wherein R is hydrogen. (Alternatively the same intermediate is formed by reaction of the idomethyl ester of one of the present compounds with the salt of the penicillin). In the final step the benzyloxycarbonyl amino or azido group is hydrogenated to an amino group, as noted above.

As indicated above, some of the compounds of the formula (I), generally those wherein R is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta Pathologica et Microbiologia Scandinav,* Suppl. 217, Section B: 64–68 ([1971])], and employs brain heart infusion (BHI) agar and an inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Those compounds of the formula (I) having said in vitro antibacterial activity are thus useful as industrial antimicrobials, for example in water treatment, slime control, paint preservation and wood preservation, as well as for topical application in mammals. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formula (I) are generally of sufficient antibacterial activity to be useful as systemic antibacterial agents, particularly when the sidechain is in the preferred S-configuration. In determining such in vivo activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound of the formula (I) is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as $PD_{50}$ (dose which protects 50% of the animals from infection).

Even more generally, the compounds of the formula (I) are of special value as potent inhibitors of microbial beta-lactamases. By this mechanism they increase their own antibacterial effectiveness or the antibacterial effectiveness of a conventional beta-lactam antibiotic (penicillin or cephalosporin) against many microorganisms, particularly those which produce a beta-lactamase. Thus the ability of the said compounds of the formula (I) in vitro is also evaluated by the ability of the compounds (I) wherein R is H to inhibit the hydrolysis of certain beta-lactam antibiotics by beta-lactamase enzymes. For example, the hydrolysis of ampicillin and penicillin G is determined by the microiodometric method of Novick (Biochem. j. 83, 236 (1962)], while cephaloridine hydrolysis is measured by following the decrease in ultraviolet absorbance at 255 nm [O'Callaghan et al., Antimicrob. Agents Chemother. 1968, pp. 57-63 (1969)]. Conditions for both assays are identical: 0.5M potassium phosphate, pH 6.5 and 37° C. Reactions are initiated by the addition of the cell-free beta-lactamase, except in the case of preincubation experiments in which the inhibitor and enzyme are incubated together in the assay mixture for 10 minutes before initiation of the reaction by addition of substrate. With the cell-free extracts of *Staphylococcus aureus, Escherichia coli, Klebsiella pneumoniae* and *Pseudomonas aeruginosa,* the substrate is ampicillin at 33 micro M (13 microg./ml.). Typical specific activities of the beta-lactamase preparations are, respectively, 6,019, 88,970, 260 and 76 micromol/hr. per mg. of protein. Penicillin G (33 micromol) is the substrate used with the *Enterobacter cloacae* beta-lactamase, which shows a typical specific activity of 10,080 micromol/hr. per mg. of protein.

Cell-free extracts are prepared by sonic treatment (using three 30-s bursts at 4° C. except for *S. aureus,* which is broken with a French press) of cultures grown in brain heart infusion on a rotary shaker incubator. For the *S. aureus, P. aeruginosa,* and *E. cloacae* strains, de novo synthesis of beta-lactamase is induced by growing a log-phase culture in the presence of a sublethal concentration of penicillin G at 100, 1,000, and 300 microg./ml., respectively, for 2.5 hours.

The ability of compounds of the formula (I) to increase the effectiveness of a beta-lactam antibiotic can be appreciated by reference to experiments in which the MIC values of the antibiotic alone, and a compound of the formula (I) (having R as hydrogen) alone, are determined. These MIC's are then compared with the MIC values obtained with a combination of the given antibiotic and the compound of the formula (I), wherein R is hydrogen. When the antibacterial potency of the combination is significantly greater than would have been predicted from the potencies of the individual compounds, this is considered to constitute synergism or enhancement of activity. The MIC values of combination are measured using the method described by Barry and Sabath in "Manual of Clinical Microbiology", edited by Lenette, Spaulding and Truant, 2nd Edition, 1974, American Society for Microbiology.

The compounds of the formula (I) also generally enhance the antibacterial effectiveness of beta-lactam antibiotics in vivo. That is, they lower the amount of the antibiotic which is needed to protect mice against an otherwise lethal inoculum of certain beta-lactamase producing bacteria. Such in vivo tests are carried out in the manner described above for single agents, but in this case the mice are dosed with a combination of the test compound (I) wherein R is hydrogen or an in vivo hydrolzable ester and the beta-lactam antibiotic under study.

In determining whether a particular strain of bacteria is sensitive to a particular compound of the formula (I) wherein R is an acyloxymethyl group derived from a beta-lactam antibiotic, it is not necessary to carry out an in vivo test. Instead, the MIC of a 1:1 molar mixture of a compound of the formula (I) wherein R is hydrogen, and the appropriate beta-lactam antibiotic is measured according to methods described above.

The ability of the compounds of formula (I), wherein R is hydrogen or a in vivo hydrolyzable ester, to enhance the effectiveness of a beta-lactam antibiotic against beta-lactamase producing bacteria makes them valuable for co-administration with beta-lactam antibiotics in the treatment of bacterial infections in mammals, particularly man. In the treatment of a bacterial infection, the compound of the formula (I) can be comingled with the beta-lactam antiobiotic, and the two agents thereby administered simultaneously. Alternatively, the compound of the formula (I) can be administered as a separate agent during a course of treatment with a beta-lactam antibiotic. In some instances it will be advantageous to pre-dose the subject with the compound of the formula (I) before initiating treatment with a beta-lactam antibiotic.

When simultaneously administering a compound of formula (I) and a beta-lactam antibiotic, it is preferred to administer a mixture of (I) and the beta-lactam antibiotic in a single formulation. Such a pharmaceutical composition will normally comprise the beta-lactam antibiotic, the compound of formula (I) and from about 5 to about 80 percent of a pharmaceutically acceptable carrier or diluent by weight. Said carrier or diluent is chosen on the basis of the intended mode of administration. For oral administration, tablets, capsules, lozenges, troches, powders, syrups, elixirs, aqueous solutions and suspensions, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening and/or flavoring agents can be added. For parenteral administration, which includes intramuscular, intraperitoneal, subcutaneous, and intravenous injection, sterile solutions of the active ingredient are usually prepared, and the pH of the solutions are suitably adjusted and buffered. For intravenous use, the total concentration of solutes should be controlled to render the preparation isotonic. When dosed separately, compounds of the formula (I) are formulated in like manner.

When using the compounds of formula (I) in combination with another beta-lactam antibiotic, said compounds are administered orally or parenterally, i.e., intramuscularly, subcutaneously or intraperitoneally. Although the prescribing physician will ultimately decide the dosage to be used in a human subject, the ratio of the daily dosages of the compounds of formula (I) and the beta-lactam antibiotic will normally be in the range from about 1:10 to 3:1 by weight. Additionally, when using the compounds of formula (I) in combination with another beta-lactam antibiotic, the daily oral dosage of each component will normally be in the range from about 10 to about 200 mg. per kilogram of body weight and the daily parenteral dosage of each component will normally be about 5 to about 50 mg. per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) is to be used simultaneously (i.e. comingled) with a beta-lactam antibiotic which is effective only on parenteral administration, a combination formulation suitable for parenteral use will be required. When a compound of formula (I) is to be used simultaneously (comingled) with a beta-lactam antibiotic which is effective orally or parenterally, combination suitable for either oral or parenteral administration can be prepared. Additionally, it is possible to administer preparations of the compounds of formula (I) orally, while at the same time administering a further beta-lactam antibiotic parenterally, and it is also possible to administer preparation of the compounds of formula (I) parenterally, while at the same time administering the further beta-lactam antibiotic orally.

It is the capacity of compounds of the formula (I), wherein R is an acyloxymethyl derivative of a beta-lactam antibiotic, to hydrolyze and provide both the compounds of the formula (I) wherein R is hydrogen and the beta-lactam antibiotic which enhances the activity and broadens the antibacterial spectrum of these compounds relative to the use of an equivalent amount of beta-lactam antibiotic alone.

When using one of the present antibacterial compounds of the formula (I) alone for control of bacterial infections in a mammal, particularly man, the compound is administered alone, or mixed with pharmaceutically acceptable carriers or diluents, in the manner described above.

When using the more active compounds of the formula (I) alone to control bacterial infections, the daily dosage will be similar to those of other clinically useful beta-lactam antibiotics. Although the prescribing physician will ultimately decide the dosage to be used in a human subject, these compounds will normally be used orally at dosages in the range from about 20 to about 100 mg. per kilogram of body weight per day, and parenterally at dosages from about 10 to about 100 mg. per kilogram of body weight per day, usually in divided doses. In some instances, the prescribing physician will determine that dosages outside these limits are needed.

The present invention is illustrated by the following examples. However, it should be understood that the invention is not limited to the specific details of these examples. Abbreviations are used as follows: THF for tetrahydrofuran; AIBN for azo-bisisobutyronitrile; DMAP for 4-dimethylaminopyridine; DMF for dimethylformamide; DMSO for dimethylsulfoxide; tlc for thin-layer chromatography on silica gel plates, with detection by u.v. and/or KMnO$_4$ spray; $^1$H-nmr for proton nuclear magnetic resonance spectra, with delta in ppm at 60 MHz, unless otherwise specified. Unless otherwise specified, all operations were carried out at ambient temperature, generally between 17.5° and 26.5° C.; specified temperatures are in °C.; and all solvents were stripped in vacuo.

METHOD A—GRIGNARD REACTIONS

EXAMPLE A1

Benzyl 6-Bromo-6-[R-1-(N,N-dimethylcarbamoyl)-1-hydroxymethyl]penicillanate

Benzyl 6,6-dibromopenicillanate (72.7 g., 0.162 mol) was dissolved in 475 ml. THF and cooled to −78°. Methylmagnesium bromide (59 ml. of 3M in ether, 0.178 mol) was added over 3 minutes and the solution stirred 30 minutes at −78°. Freshly prepared N,N-dimethylglyoxylamide (18 g., 0.178 mol) in 75 ml. THF at −78° was then added in one portion. After stirring 5 minutes, the mixture was quenched with acetic acid (26 ml., 0.445 mol), warmed and stripped. The residue was taken up in 40 ml. ethyl acetate and 500 ml. H$_2$O. The organic layer was separated, washed 3×500 ml. fresh H$_2$O and 1× with brine, dried over Na$_2$SO$_4$, stripped to an oil (84 g.), and chromatographed on 800 g. silica gel with 3:7 ethyl acetate:CHCl$_3$ is eluant, monitoring by tlc, and collecting 500 ml. fractions. Fractions 6 and 7 were stripped to yield 5.3 g. of purified title product. Fractions 3–5 were stripped to a mixture which was rechromatographed in like manner to yield an additional 5 g. of purified title product; tlc Rf 0.4 (3:7 ethyl acetate:CHCl$_3$); $^1$H-nmr (CDCl$_3$) delta (ppm) 1.35 (3H, s), 1.61 (3H, s), 2.94 (3H, s), 3.05 (3H, s), 4.46 (1H, s), 4.98 (1H, br.s), 5.12 (2H, s), 5.84 (1H, s), 7.37 (5H, s).

EXAMPLE A2

Benzyl 6-Bromo-6-[1-(N-isopropylcarbamoyl)-1-hydroxymethyl]penicillanate

By the method of the preceding Example, benzyl 6,6-dibromopenicillanate (12.2 g., 0.027 mol) and N-isopropylglyoxylamide (3.8 g., 0.033 mol) were converted to crude title product (16 g.) as an oil. The latter was taken up in minimal CHCl$_3$, flakey solids (0.5 g.,) removed by filtration and the filtrate chromatographed on 600 g. of silica gel using 3:17 ethyl acetate:CHCl$_3$ as eluant to yield purified title product, 0.65 g., which appeared to be predominantly one isomer; $^1$H-nmr (CDCl$_3$) delta (ppm) 1.17 (6H, d), 1.35 (3H, s), 1.61 (3H, s), 3.7–4.3 (2H, complex), 4.46 (1H, s), 4.62 (1H, s), 5.13 (2H, s), 5.80 (1H, s), 6.52 (1H, br.d), 7.3 (5H, s).

EXAMPLE A3

Benzyl 6-Bromo-6-[1-(pyrrolidinocarbonyl)-1-hydroxymethyl]penicillanate

By the method of Example A1, chromatographing on 550 g. silica gel with 1:4 ethyl acetate:CHCl$_3$ as eluant and collecting 25 ml. fractions, benzyl 6,6-dibromopenicillanate (41.9 g., 0.093 mol) and N-glyoxyloylpyrrolidine (11.87 g., 0.093 mol) were converted to title product, isolated by combining and stripping fractions 76-100, 4.9 g.; $^1$H-nmr (CDCl$_3$) delta (ppm) 1.39 (3H, s), 1.64 (3H, s), 1.7–2.1 (4H, complex), 3.3–3.8 (4H, complex), 4.53 (1H, s), 4.87 (1H, br.s), 5.18 (2H, s), 5.99 (1H, s), 7.36 (5H, s).

EXAMPLE A4

Benzyl 6-Bromo-6-[R-1-(piperidinocarbonyl)-1-hydroxymethyl]penicillanate

By the method of Example A1, chromatographing on 600 g. silica gel with 1:9 ethyl acetate:CHCl$_3$ as eluant and collecting 25 ml. fractions, benzyl 6,6-dibromopenicillante (27 g., 0.06 mol) and N-glyoxyloxylpiperidine (13.74 g.) were converted to title product isolated by stripping combined fractions 45-70, 8.0 g.; $^1$H-nmr (CDCl$_3$) delta (ppm) 1.38 (3H, s), 1.3–1.8 (9H, complex), 3.3–3.8 (4H, complex), 4.51 (1H, s), 5.11 (1H, s), 5.18 (2H, s), 5.81 (1H, s), 7.33 (5H, s).

EXAMPLE A5

Benzyl 6-Bromo-6-[1-(morpholinocarbonyl)-1-hydroxymethyl]penicillanate

By the method of Example A1, benzyl 6,6-dibromopenicillanate (18 g., 0.040 mol) and N-glyoxyloylmorpholine (4.74 g.) were converted to title product, chromatographed on 250 g., silica gel eluted with 3:7 ethyl acetate:CHCl$_3$. Those fractions containing mainly mp isomer were combined, 4.54 g.; tlc Rf 0.4 (3:7 ethyl acetate:CHCl$_3$); $^1$H-nmr (CDCl$_3$) delta (ppm) 1.40 (3H, s), 1.65 (3H, s), 3.4–3.8 (8H, complex), 4.56 (1H, s), 5.03 (1H, br.s), 5.11 (2H, s), 5.90 (1H, s), 7.38 (5H, s).

PREPARATION A1

Benzyl 6-Bromo-6-[R- and S-1-(allyloxycarbonyl)-1-hydroxymethyl]penicillanate Benzyl 6,6-dibromopenicillanate (128.9 g., 0.28 mol) was dissolved in 500 ml. dry THF and cooled to −78° C. Methylmagnesium bromide (98.9 ml. of 2.9M in ether) was added and the cold mixture stirred for 15 minutes. Allyl glyoxalate (37 g., 0.32 mol) was added in one portion and the mixture stirred 1 hour at −78°; quenched with acetic acid (34.4 ml., 0.57 mol), warmed and stripped. The residue was distributed between 500 ml. ethyl acetate and 200 ml. H$_2$O, and the organic layer separated, washed with 2×100 ml. fresh H$_2$O and 1×200 ml. brine, dried over Na$_2$SO$_4$, stripped to an oil and chromatographed on 1200 g. of silica gel with 1:19 ethyl acetate:CHCl$_3$ as eluant. After the initial 1.5 l. of eluate was discarded, 20 ml. fractions were collected. Fractions 21–40 gave benzyl 6-bromopenicillanate, and fractions 41–60 gave 40 g. of a mixture of said 6-bromopenicillanate and title R- and S-isomers. Fractions 61–140 gave 56 g. of residue which was slurried in 100 ml. of ether and filtered to yield crystalline, more polar S-isomer of title product, of unspecified stereochemistry of C.6, 12.3 g.; mp 123°–125° C.; $^1$H-nmr (CDCl$_3$) delta (300 MHz) 1.38 (3H, s), 1.63 (3H, s), 4.53 (1H, s), 4.56–4.76 (3H, complex), 5.17 (2H, s), 5.22–5.36 (3H, complex), 5.63 (1H, s), 5.82 (1H, m), 7.34 (5H, s).

The 40 g. mixture from above fractions 41–60 was rechromatographed on 1200 g. of silica gel with CHCl$_3$ as eluant. After discarding the intitial 2 l. of eluate, 20 ml. fractions were collected. Fractions 10–60 gave an additional 30 g. of benzyl 6-bromopenicillanate; fractions 120–250 gave less polar title R-isomer, 23.6 g.; mp 78°–79° C.; $^1$H-nmr (CDCl$_3$) delta (300 MHz) 1.37 (3H, s), 1.60 (3H, s), 4.52 (1H, s), 4.64–4.72 (3H, complex), 5.15 (2H, ABq), 5.26 (1H, dd, J(1 g)=10 Hz), 5.36 (1H, dd, J(1 g)=16 Hz), 5.56 (1H, s), 5.88 (1H, m), 7.32 (5H, s); fractions 251–450 were combined, stripped and the residue slurried in 100 ml. ether to yield additional S-isomer, 17 g., identical with the material isolated from the initial chromatography.

DEBROMINATION REACTIONS

EXAMPLE B1

Benzyl 6-beta-[S-1-(Dimethylcarbamoyl)-1-hydroxymethyl]penicillanate

R-Title product of Example A1 (5 g., 0.011 mol) was dissolved in 50 ml. benzene. Tributyltin hydride (9.1 ml., 9.8 g., 0.033 mol) was added and the mixture refluxed for 2.5 hours, stripped of solvent and the residue taken up in 100 ml. CH$_3$CN and hexane. The CH$_3$CN layer was separated, washed 2×75 ml. fresh hexane, stripped to an oil, crystallized from ether, cooled to 0° and title product recovered by filtration, 1.1 g.; $^1$H-nmr (CDCl$_3$) delta (TMS): 1.37 (3H, s), 1.61 (3H, s), 2.94 (3H, s), 3.16 (3H, s), 3.53 (1H, d, J=6 Hz), 4.00 (1H, dd, J=4 Hz, 9 Hz), 4.43 (1H, s), 4.83 (1H, dd, J=6 Hz, 9 Hz), 5.16 (2H, s), 5.46 (1H, d, J=4 Hz), 7.3 (5H, s).

EXAMPLE B2

Benzyl 6-beta-[R- and S-1-(Isopropylcarbamoyl)-1-hydroxymethyl]penicillanate Title product of Example A2 (mixed R- and S-isomers; 0.65 g., 1.34 mmol), was debrominated and crude product isolated as an oil (0.70 g.) from hexane washed acetonitrile according to Example B1. The crude product was chromatographed on 25 g. silica gel using 1:9 ethyl acetate:CHCl$_3$ as eluant, collecting 7 ml. fractions. Fractions 12–18 were stripped to yield title product R-epimer, 210 mg.; $^1$H-nmr (CDCl$_3$) delta (TMS) : 1.20 (6H, d, J=6 Hz), 1.40 (3H, s), 1.65 (3H, s), 3.63 (1H, dd, J=4 Hz, 10 Hz), 3.8-4.5 (3H, complex overlapping multiplets), 4.41 (1H, s), 5.14 (2H, s), 5.38 (1H, d, J=4 Hz), 7.3 (5H, s). Fractions 24–48 were stripped to yield S-epimer, 25 mg.; $^1$H-nmr (CDCl$_3$) delta (TMS): 1.15 (6H, d, J=7 Hz), 1.40 (3H, s), 1.64 (3H, s), 3.57 (1H, d, J=3 Hz), 3.83 (1H, dd, J=4 Hz, 9 Hz), 4.18 (1H, m), 4.44 (1H, s), 4.64 (1H, dd, J=3 Hz, 9 Hz), 5.20 (2H, s), 5.51 (1H, d, J=4 Hz), 7.35 (5H, s).

EXAMPLE B3

Benzyl 6-beta-[R- and S-1-(Pyrrolidinocarbonyl)-1-hydroxymethyl]penicillanate Title product of Example A3 (4.9 g., 9.9 mmol) was debrominated according to Example B1 to yield crude title product as an oil (4.0 g.) from the hexane washed CH$_3$CN. The oil was chromatographed on 300 g. silica gel with 1:3 ethyl acetate:CHCl$_3$ as eluant, collecting 5 ml. fractions and monitoring by tlc. More polar fractions 140–200 were combined and stripped to yield purified S title product as a second oil, 1.5 g. Addition of ethyl acetate gave crystalline S title product, 0.40 g., m.p. 88°-92°. Stripping of the ethyl acetate filtrate and treatment with ether gave a second crop thereof, 0.50 g., m.p. 90°-93°; tlc Rf 0.3 (3:7 ethyl acetate:CHCl$_3$); $^1$H-nmr (CDCl$_3$) delta (TMS): 1.38 (3H, s), 1.63 (3H, s), 1.92 (4H, m), 3.3-3.8 (5H, complex multiplet), 4.02 (1H, dd, J=4 Hz, 10 Hz), 4.42 (1H, s), 4.70 (1H, br.d.), 5.14 (2H, s), 5.44 (1H, d, J=4 Hz), 7.3 (5H, s). Less polar fractions 66–85 were stripped to yield the R-epimer as an oil (1.0 g.), crystallized with ether, 0.37 g.; m.p. 88°-90°; tlc Rf 0.45 (3:7 ethyl acetate:CHCl$_3$). Center fractions gave a mixture of R- and S-epimers, 1.15 g., suitable for chromatographic recycling.

EXAMPLE B4

Benzyl 6-beta-[S-1-(Piperidinocarbonyl)-1-hydroxymethyl]-penicillanate

Using a reflux time of 6.5 hours the procedure of the preceding Example was used to convert title product of Example A4 (8 g., 0.016 mol) to present chromatographed title product; 3.6 g.; tlc Rf 0.15 (1:1 ethyl acetate:CHCl$_3$), $^1$H-nmr (CDCl$_3$) delta (TMS): 1.33 (3H, s), 1.2-1.7 (9H, complex overlapping multiplets), 3.1-3.6 (4H, complex overlapping mulitplets), 3.93 (1H, dd, J=4 Hz, 10 Hz), 4.41 (1H, s), 4.5-4.9 (2H, overlapping multiplets), 5.13 (2H, s), 5.41 (1H, d, J=4 Hz), 7.3 (5H, s).

EXAMPLE B5

Benzyl 6-beta-[R- and S-1-(Morpholinocarbonyl)-1-hydroxymethyl]penicillanate Using the procedure of Example B3, title product of Example A5 (4.62 g., 0.0086 mol) was converted to mixed title products as an oil (6.0 g.). The latter was chromatographed on 240 g. of silica gel with 3:7 ethyl acetate:CHCl$_3$ as eluant with 10 ml. fractions. Fractions 59–72 were combined and stripped to yield the less polar R-epimer of title product, an oil which partially crystallized on standing at 5° and was completely crystallized from ethyl acetate and ether, 0.12 g.; $^1$H-nmr (CDCl$_3$) delta (TMS): 1.40 (3H, s), 1.64 (3H, s), 3.4-4.0 (10, complex overlapping multiplets), 4.40 (1H, s), 4.81 (1H, dd, J=8 Hz, 10 Hz), 5.16 (2H, s), 5.46 (1H, d, J=4 Hz), 7.35 (5H, s). Fractions, 90–119 were combined and stripped to yield the more polar S-epimer of title product, 1.3 g.; $^1$H-nmr (CDCl$_3$) delta (TMS): 1.38 (3H, s), 1.61 (3H, s), 3.2-3.9 (9H, complex overlapping multiplets), 4.03 (1H, dd, J=4 Hz, 8 Hz), 4.43 (1H, s), 4.83 (1H, dd, J=6 Hz, 8 Hz), 5.17 (2H, br.s.), 5.46 (1H, d, J=4 Hz), 7.3 (5H, s).

PREPARATION B1

Benzyl 6-beta-[S-1-(Allyloxycarbonyl)-1-hydroxymethyl]-penicillanate

R-Title product of Preparation A1 (16.3 g.; 0.00337 mol) dissolved in 200 ml. benzene was purged with N$_2$ for 15 minutes. Tributyltin hydride (17.6 ml. of 3.826N in benzene, 0.0673 mol) was then added and the mixture refluxed 18 hours, stripped of solvent and partioned in 100 ml. CH$_3$CN and 100 ml hexane. The CH$_3$CN layer was separated, stripped to an oil and instant title product crystallized by stirring with 100 ml. ether, 6.5 g.; mp 108°-110°; $^1$H-nmr (CDCl$_3$) delta (300 MHz): 1.46 (3H, s), 1.71 (3H, s), 3.13 (1H, d, J=3 Hz), 3.92 (1H, dd, J=4 Hz, 10 Hz), 4.59 (1H, s), 4.77 (2H, d), 4.85 (1H, dd, J=3 Hz, 10 Hz), 5.26 (2H, s), 5.37 (1H, d), 5.43 (1H, d), 5.55 (1H, d, J=4 Hz), 5.96 (1H, complex), 7.44 (5H, s).

The present preparation was repeated on 21 g. of R-title product of Preparation A1, using a reflux time of 1 hour. The residual oil following acetonitrile strip was chromatographed on 800 g. of silica gel with 1:19 ethyl acetate:CHCl$_3$ as eluant. After discarding the initial liter of eluate, 20 ml. fractions were collected. Fractions 131–190 were stripped to an oil which was crystallized from 100 ml. of ether, 5.8 g.; m.p. 108°-110° C.; structure and stereochemistry confirmed by X-ray crystallographic analysis.

PREPARATION B2

Benzyl 6-beta-[R-1-(Allyloxycarbonyl)-1-hydroxymethyl]-penicillanate

S-Title product of Preparation A1 (10.1 g., 0.0208 mol), by the procedure of the preceding Preparation, was converted to instant title product. The initially obtained oil was chromatographed on 400 g., of silica gel, eluting with CHCl$_3$. After 1.5 l. forerun, 20 ml. fractions were collected. Fractions 48–75 were combined and stripped to yield purified title product still as an oil, 5.5 g.; $^1$H-nmr (CDCl$_3$) delta (CDCl$_3$) (300 MHz): 1.43 (3H, s), 1.69 (3H, s), 3.41 (1H, d, J=8 Hz), 3.98 (1H, dd, J=4 Hz, 8 Hz), 4.53 (1H, s), 4.75 (3H, complex), 5.23 (2H, s), 5.32 (1H, d), 5.41 (1H, d), 5.50 (1H, d, J=4 Hz), 5.96 (1H, complex), 7.42 (5H, s).

The present preparation was repeated on 17 g. of the S-title product of Preparation A1 using a reflux time of 4 hours and chromatography on 300 g. of silica gel with 1:19 ethyl acetate:CHCl$_3$ as eluant to yield 14.0 g. of present purified title product.

METHOD C AMINOLYSIS REACTIONS

EXAMPLE C1

Benzyl 6-beta-(S-1-Carbamoyl-1-hydroxymethyl)penicillanate

Title product of Preparation F1 (400 mg., 1.0 mmol) was dissolved in 3.6 ml. THF and cooled to −15° with stirring. COCl$_2$ in CCl$_4$ (0.7M, 2.2 ml., 1.6 mmol); 0.5 minutes later, diisopropylethylamine in THF (0.57M, 3.6 ml., 2.1 mmol); and 2.0 minutes later, conc. NH$_4$OH (8.25M, 0.5 ml., 4.1 mmol) were added. After stirring 20 minutes at $-15°$, the reaction mixture was quenched with acetic acid (0.42 ml., 0.43 g., 7.2 mmol) and then poured into 75 ml. of ethyl acetate and 35 ml. H$_2$O. The organic phase was washed 3×35 ml. fresh H$_2$O, 1× brine, dried and stripped to an oil (500 mg.) which was chromatographed on 30 g. silica gel employing 1:2 ethyl acetate:CHCl$_3$ as eluant. Clean product fractions were combined, stripped and crystallized from ethyl acetate and ether, 100 mg.; $^1$H-nmr (CDCl$_3$) delta (TMS): 1.40 (3H, s), 1.63 (3H, s), 3.7–4.0 (2H, overlapping multiplets), 4.43 (1H, s), 4.65 (1H, m), 5.16 (2H, s), 5.46 (1H, d, J=4 Hz), 5.77 (1H, br.), 6.62 (1H, br.), 7.32 (5H, s).

EXAMPLE C2

Benzyl 6-beta-[S-1-(Benzylcarbamoyl)-1-hydroxymethyl]-penicillanate

Title product of Preparation F1 (0.5 g., 0.0013 mol) was dissolved in 5 ml. THF. COCl$_2$ in CCl$_4$ (1.2M, 10 ml., 0.012 ml.) was added. After stirring 5 minutes, the mixture was stripped to yield the cyclic anhydride, benzyl 6-beta-(1,3-dioxolane-2,5-dion-4-yl)penicillanate as a solid foam. The latter was dissolved in 5 ml. fresh THF and a solution of benzylamine (0.14 ml., 0.0013 mol) in 1 ml. CH$_2$Cl$_2$ added, forming an immediate precipitate. The reaction mixture was diluted with 10 ml. CH$_2$Cl$_2$ and stirred 5 minutes. An additional portion of benzylamine (0.14 ml.) was added, stirring continued 10 minutes longer, and the reaction mixture stripped. The residue was distributed between 30 ml. ethyl acetate and 30 ml. H$_2$O. The pH was adjusted to 6.0 with dilute HCl and the organic layer was separated washed 2×20 ml. fresh H$_2$O, 1×20 ml. brine, dried, stripped to an oil, chromatographed on 40 g. silica gel with 3:7 ethyl acetate:CHCl$_3$ as eluant, collecting 10 ml. fractions. Fraction numbers 6 to 8 were combined, stripped to an oil, rechromatographed on 50 g. fresh silica gel with 3:17 ethyl acetate:CHCl$_3$ as eluant, monitoring by tlc, to yield purified title product, 60 mg.; tlc Rf 0.6 (3:17 ethyl acetate:CHCl$_3$); $^1$H-nmr (CDCl$_3$) delta (TMS): 1.37 (3H, s), 1.62 (3H, s), 3.81 (1H, dd, J=4 Hz, 9 Hz), 4.38 (2H, m), 4.41 (1H, s), 4.68 (1H, d, 9 Hz), 5.13 (2H, s), 5.46 (1H, d, J=4 Hz), 7.2 (5H, s), 7.3 (5H, s).

EXAMPLE C3

Benzyl 6-beta-[S-1-(tert-Butylcarbamoyl)-1-hydroxymethyl]-penicillanate

Title product of Preparation F1 (0.5 g., 0.0013 mol) was coupled with tert-butylamine in THF (0.95N, 5.4 ml., 0.0052 mol) according to Example C1. Following acetic acid quench, precipitated acetate salts were removed by filtration. The filtrate was poured into 75 ml. ethyl acetate/35 ml. H$_2$O. The pH was 5.0. The organic layer was separated, washed 3×35 ml. H$_2$O, dried, and stripped to an oil (0.7 g.). The latter was chromatographed on 30 g. silica gel using 3:17 ethyl acetate:CHCl$_3$ as eluant, collecting 10 ml. fractions and monitoring by tlc. Fractions 12 to 15 were combined and stripped to yield purified title product, 0.20 g.; tlc Rf 0.45 (1:4 ethyl acetate:CHCl$_3$); $^1$H-nmr (CDCl$_3$) delta (TMS): 1.36 (9H, s), 1.39 (3H, s), 1.63 (3H, s), 3.77 (1H, dd, J=4 Hz, 8 Hz), 3.97 (1H, d, J=3 Hz), 4.41 (1H, s), 4.58 (1H, dd, J=3 Hz, 8 Hz), 5.16 (2H, s), 5.49 (1H, d, J=4 Hz), 6.55 (1H, br.s), 7.3 (5H, s).

EXAMPLE C4

Benzyl 6-beta-[S-1-(Phenylcarbamoyl)-1-hydroxymethyl]-penicillanate

By the method of Example C2, title product of Preparation F1 (0.5 g., 0.0013 mol) and a single portion of aniline (0.1175 ml., 0.0013 mol) were converted to instant title product, as an oil, using 1:10 ethyl acetate:CHCl$_3$ as eluant on chromatography, 0.1 g.; $^1$H-nmr (CDCl$_3$) delta (TMS): 1.40 (3H, s), 1.66 (3H, s), 3.87 (1H, dd, J=4 Hz, 9 Hz), 4.46 (1H, s), 4.83 (1H, d, J=9 Hz), 5.17 (2H, s), 5.53 (1H, d, J=4 Hz), 7.0–7.6 (10H, arom.), 8.5 (1H, br.s).

EXAMPLE C5

Benzyl 6-beta-[S-1-(Diethylcarbamoyl)-1-hydroxymethyl]-penicillanate

Using 1:3 ethyl acetate:CHCl$_3$ as chromatography eluant, the method of Example C1 was used to convert title product of Preparation F1 (0.4 g., 1 mmole) and diethylamine (4.2 ml. of 0.97M in THF, 4.1 mmol) to instant title product, 0.35 g.; $^1$H-nmr (CDCl$_3$) delta (TMS): 1.03 (3H, t), 1.15 (3H, t), 1.27 (3H, s), 1.53 (3H, s), 3.0–3.9 (4H, overlapping multiplets), 3.95 (1H, dd, J=4 Hz, 10 Hz), 4.34 (1H, s), 4.69 (1H, d, J=10 Hz), 5.06 (2H, s), 5.37 (1H, d, J=4 Hz), 7.25 (5H, s).

EXAMPLE C6

Benzyl 6-beta-[S-1-(Perhydroazepinocarbonyl)-1-hydroxymethyl]penicillanate

Using 2:9 ethyl acetate:CHCl$_3$ as eluant, the procedure of Example C1 was used to convert title product of Preparation F1 (0.5 g., 0.0013 mol) and perhydroazepine (homopiperidine, 5.8 ml. of 0.89M in THF, 0.0052 mol) to instant chromatographed title product, 0.33 g., tlc Rf 0.45 (3:7 ethyl acetate:CHCl$_3$); $^1$H-nmr (CDCl$_3$) delta (TMS): 1.39 (3H, s), 1.2–2.0 (11H, overlapping complex multiplet), 3.0–4.3 (5H, complex overlapping multiplets), 4.04 (1H, dd, J=4 Hz, 10 Hz), 4.45 (1H, s), 4.81 (1H, d, J=10 Hz), b 5.17 (2H, s), 5.45 (1H, d, J=4 Hz), 7.3 (5H, s).

EXAMPLE C7

Benzyl 6-beta-[S-1-Hydroxypiperidinocarbonyl)-1-hydroxymethyl]penicillanate

By the method of Example C1, title product of Preparation F1 (0.45 g., 0.00116 mol) and 4-hydroxypiperidine (0.117 g., 0.00116 mol) were converted to instant title product. The crude material was isolated as a solid foam (0.38 g.) which was chromatographed on 50 g. silica gel using ethyl acetate as eluant to yield purified title product as a second solid foam, 0.13 g.; tlc Rf 0.3 (ethyl acetate); $^1$H-nmr (CDCl$_3$) delta (TMS): 1.36 (3H, s), 1.4–2.0 (4H, complex multiplet), 2.9–4.1 (8H, complex overlapping multiplets), 4.40 (1H, s), 4.80 (1H, br.d, J=9 Hz), 5.14 (2H, br.s), 5.43 (1H, d, J=4 Hz), 7.3 (5H, s).

EXAMPLE C8

Benzyl 6-beta-[S-1-(4-Formylpiperazinocarbonyl)-1-hydroxymethyl]penicillanate By the procedure of Example C1, adjusting the pH from 3.2 to 5.8 with 2N NaOH during aqueous wash and using 3% methanol in ethyl acetate as eluant, title product of Preparation F1 (0.40 g., 1.0 mmol) and N-formylpiperazine (4.2 ml. of 0.97M in THF, 4.1 mmol) were converted to instant, chromatographed title product, 0.26 g.; tlc Rf 0.4 (1:19 methanol:ethyl acetate); $^1$H-nmr (CDCl$_3$) delta (TMS): 1.39 (3H, s), 1.60 (3H, s), 3.2–4.0 (8H, overlapping multiplets), 4.05 (1H, dd, J=4 Hz, 10 Hz), 4.47 (1H, s), 4.90 (1H, br.d), 5.20 (2H, s), 5.53 (1H, d, J=4 Hz), 7.35 (5H, s), 8.06 (1H, s).

EXAMPLE C9

Benzyl 6-beta-[S-1-(Methylcarbamoyl)-1-hydroxymethyl]penicillanate

By the procedure of Example C1 adjusting the pH from 3.5 to 5.0 during aqueous wash and using ethyl acetate as eluant, title product of Preparation F1 (0.40 g., 1 mmol) and methylamine (3.3 ml. of 1.24M, 1.24 mmols) were converted to present, chromatographed title product as an oil, 0.37 g.; $^1$H-nmr (CDCl$_3$) delta (TMS): 1.41 (3H, s), 1.66 (3H, s), 2.83 (3H, d, J=5 Hz), 3.85 (1H, dd, J=4 Hz, 9 Hz), 4.33 (1H, br.d), 4.46 (1H, s), 4.73 (1H, br. dd), 5.11 (2H, s), 5.54 (1H, d, J=4 Hz), 6.9 (1H, br. multiplet), 7.4 (5H, s).

EXAMPLE C10

Benzyl 6-beta-[S-1-(2-Hydroxyethylcarbamoyl)-1-hydroxymethyl]penicillanate

By the method of Example C1, using ethyl acetate as eluant, title product of Preparation F1 (0.40 g., 1.0 mmol) and ethanolamine (2.5 ml. of 1.7M in THF, 4.1 mmols) were converted to instant, chromatographed title product as an oil, 0.33 g.; tlc Rf 0.2 (ethyl acetate), 0.6 (1:9 methanol:ethyl acetate); $^1$H-nmr (CDCl$_3$) delta (TMS): 1.40 (3H, s), 1.64 (3H, s), 3.2–4.0 (6H, overlapping multiplets), 4.43 (1H, s), 4.5–4.8 (2H, overlapping multiplets), 5.16 (2H, s), 5.46 (1H, d, J=4 Hz), 7.35 (5H, s).

EXAMPLE C11

Benzyl 6-beta-[S-1-(1,2,3,4-Tetrahydroisoquinolinocarbonyl)-1-hydroxymethyl]penicillanate By the method of Example C9, using 3:17 ethyl acetate:CHCl$_3$ as eluant, title product of Preparation F1 (0.40 g., 1.0 mmol) and 1,2,3,4-tetrahydroisoquinoline (5.1 ml. of 0.8M in THF, 4.1 mmols) were converted to instant, chromatographed title product, 0.25 g.; tlc Rf 0.55 (3:17 ethyl acetate:CHCl$_3$); $^1$H-nmr (CDCl$_3$) delta (TMS): 1.35 (3H, br.s), 1.60 (3H, br.s), 2.7–3.0 (2H, complex multiplets), 3.6–4.2 (5H, overlapping multiplets), 4.44 (1H, s), 4.6–5.0 (3H, overlapping multiplets), 5.15 (2H, s), 5.47 (1H, d, J=4 Hz), 7.09 (4H, s), 7.3 (5H, s).

EXAMPLE C12

Benzyl 6-beta-[S-1-(N-Methyl-N-[2-hydroxyethyl]carbamoyl)-1-hydroxymethyl]penicillanate By the procedure of Example C1, adjusting the pH from 3.2 to 5.5 during water wash and using 3:1 ethyl acetate:CHCl$_3$ as eluant, title product of Preparation F1 (0.40 g., 1 mmol) and N-methylethanolamine (3.3 ml. of 0.8M in THF, 4.1 mmols) were converted to chromatographed title product as an oil, 0.25 g.; tlc Rf 0.25 (3:1 ethyl acetate:CHCl$_3$); $^1$H-nmr (CDCl$_3$) delta (TMS), 300 MHz: 1.37 (3H, br.s), 1.62 (3H, br.s), 2.96 (1.5H, s), 3.22 (1.5H, s), 3.4–3.9 (4H, overlapping multiplets), 4.0–4.2 (1H, overlapping multiplets), 4.48 (0.5H, s), 4.49 (0.5H, s), 4.85 (0.5H, d, J=9 Hz), 4.93 (0.5H, d, J=10 Hz), 5.20 (2H, s), 5.50 (1H, d, J=4 Hz), 7.4 (5H, s), reflecting a 1:1 mixture of amide conformers.

EXAMPLE C13

Benzyl 6-beta-[S-1-(2-Acetamidoethylcarbamoyl)-1-hydroxymethyl]penicillanate By the procedure of Example C6, adjusting the pH from 4.0 to 5.3 during aqueous wash and 1:19 methanol:ethyl acetate as eluant title product of Preparation F1 (0.40 g., 1.0 mmol) and N-acetylethylenediamine (0.42 g., 4.1 mmols) in 1 ml. THF were converted to instant, chromatographed title product, 0.20 g.; tlc Rf 0.25 (1:19 methanol:ethyl acetate); $^1$H-nmr (CDCl$_3$) delta (TMS): 1.40 (3H, s), 1.64 (3H, s), 1.95 (3H, s), 3.4 (4H, overlapping complex), 3.93 (1H, dd, J=4 Hz, 7 Hz), 4.46 (1H, s), 4.65 (2H, overlapping multiplets), 5.20 (2H, s), 5.52 (1H, d, J=4 Hz), 6.8 (1H, broad s), 7.35 (5H, s).

EXAMPLE C14

Benzyl 6-beta-[S-1-(Di(2-hydroxyethyl)carbamoyl)-1-hydroxymethyl]penicillanate Using 1:19 methanol:ethyl acetate as eluant, but otherwise according to the procedure of Example C1, title product of Preparation F1 (400 mg., 1.0 mmol) and diethanolamine (4.3 ml. of 1.04M in THF, 4.1 mmols) were converted to instant title product, 90 mg.; tlc Rf 0.3 (1:19 methanol:ethyl acetate); $^1$H-nmr (CDCl$_3$) delta (300 MHz): 1.36 (3H, s), 1.61 (3H, s), 3.3–3.9 (8H, overlapping multiplets), 4.05 (1H, dd, J=4 Hz, 9 Hz), 4.47 (1H, s), 4.91 (1H, d, J=9 Hz), 5.19 (2H, s), 5.49 (1H, d, J=4 Hz), 7.4 (5H, s).

EXAMPLE C15

Benzyl 6-beta-[S-1-(Dipropylcarbamoyl)-1-hydroxymethyl]penicillanate

Using 1:10 ethyl acetate:CHCl$_3$ as eluant, but otherwise according to the procedure of Example C1, title product of Preparation F1 (280 mg., 0.72 mmol) and dipropylamine (3.9 ml. of 0.73M in THF, 1.17 mmoles) were converted to instant title product, 110 mg.; $^1$H-nmr (CDCl$_3$) delta: 0.7–1.1 (6H, overlapping triplets), 1.37 (3H, s), 1.62 (3H, s), 1.2–1.9 (4H, overlapping multiplets), 3.1–3.5 (4H, overlapping multiplets), 3.79 (1H, d, J=7 Hz), 4.03 (1H, dd, J=4 Hz, 10 Hz), 4.43 (1H, s), 4.78 (1H, dd, J=7 Hz, 10 Hz), 5.13 (2H, s), 5.44 (1H, s, J=4 Hz), 7.3 (5H, s).

EXAMPLE C16

Benzyl 6-beta-[S-1-(N-Benzyl-N-methylcarbamoyl)-1-hydroxymethyl]penicillanate

Using 1:10 methanol:ethyl acetate as eluant, but otherwise according to Example C1, title product of Preparation F1 (0.5 g., 1.29 mmols) and N-methylbenzylamine (0.68 ml., 5.17 mmols) were converted to instant title product, 0.23 g.; $^1$H-nmr (CDCl$_3$) delta: 1.37 (3H, br. s), 1.47 (1.2H, s), 1.61 (1.8H, s), 2.84 (1.2H, s), 3.00 (1.8H, s), 3.32 (1H, br.d, J=6 Hz), 4.00 (1H, dd, J=4 Hz, 9 Hz), 4.3–4.9 (4H, complex), 5.12 (2H, s), 5.45 (1H, d, J=4 Hz), 7.4–7.2 (10H, aromatics), reflecting amide conformers in 2:3 ratio.

EXAMPLE C17

Benzyl 6-beta-[S-1-(N-Methyl-N-phenylcarbamoyl)-1-hydroxymethyl]penicillanate

Using 1:4 ethyl acetate:CHCl$_3$ as eluant, the method of Example C1 was employed to convert title product of Preparation F1 (0.5 g., 1.29 mmols) and N-methylaniline (0.56 ml., 5.17 mmols) to instant title product, 0.31 g.; $^1$H-nmr (CDCl$_3$) delta (300 MHz): 1.38 (3H, s), 1.43 (3H, s), 3.37 (3H, s), 4.06 (1H, dd, J=4 Hz, 10 Hz), 4.44 (1H, s), 4.58 (1H, d, J=10 Hz), 5.23 (2H, s), 5.37 (1H, d, J=4 Hz), 7.3–7.6 (10H, aromatics).

EXAMPLE C18

Benzyl 6-beta-[S-1-(N-Benzyl-N-(2-hydroxyethyl)carbamoyl)-1-hydroxymethyl]penicillanate Using 1:1 ethyl acetate:CHCl$_3$ as eluant, the procedure of Example C1 was used to convert title product of Preparation F1 (0.5 g., 1.29 mmols) and N-benzylethanolamine (0.78 g., 5.17 mmols) to instant title product, 0.19 g.; $^1$H-nmr (CDCl$_3$) delta: 1.35 (3H, s), 1.41, (1.5H, s), 1.58 (1.5H, s), 3.2–4.3 (7H, complex), 4.36 (0.5H, s), 4.40 (0.5H, s), 4.5–4.9 (2H, complex), 5.07 (2H, s), 5.42 (1H, d, J=4 Hz), 7.1–7.3 (10H, aromatics), reflecting an approximately 1:1 mixture of amide conformers.

EXAMPLE C19

Benzyl 6-beta-[S-1-(4-Phenylpiperazinocarbonyl)-1-hydroxymethyl]pencillanate

Using 1:10 ethyl acetate:CHCl$_3$ as eluant and otherwise the method of Example C1, title product of Preparation F1 (0.4 g., 1 mmol) and 4-phenylpiperidine (0.66 g., 4.1 mmols) were converted to instant title product, 0.46 g.; $^1$H-nmr (CDCl$_3$) delta: 1.38 (3H, br. s), 1.5–2.0 (4H, complex), 2.3–3.4 (4H, complex), 3.7–4.3 (3H, complex), 4.42 (1H, br.s), 4.86 (1H, br.d, J=9 Hz), 5.13 (2H, br.s), 5.50 (1H, br.d., J=4 Hz), 7.0–7.4 (10H, aromatics).

EXAMPLE C20

Benzyl 6-beta-[S-1-(Dibenzylcarbamoyl)-1-hydroxymethyl]penicillanate

Using CHCl$_3$ as eluant, the method of Example C1 was employed to convert title product of Preparation F1 (0.4 g., 1 mmol) and dibenzylamine (7.9 ml. of 0.52M in THF, 4.1 mmols) title product, 0.53 g.; Rf 0.78 (3:7 ethyl acetate:CHCl$_3$); $^1$H-nmr (CDCl$_3$) delta: 1.35 (3H, s), 1.43 (3H, s), 4.10 (1H, dd, J=4 Hz, 10 Hz), 4.43 (1H, s), 3.8–5.2 (6H, complex overlapping multiplets), 5.16 (2H, s), 5.54 (1H, d, J=4 Hz), 7.1–7.5 (15H, aromatics).

EXAMPLE C21

Benzyl 6-beta-[S-1-(L-2-(Hydroxymethyl)pyrrolidinocarbonyl)-1-hydroxymethyl)penicillanate Using ethyl acetate as eluant, the method of Example C1 was employed to convert title product of Preparation F1 (0.4 g., 1 mmol) and L-prolinol (0.40 ml., 0.41 g., 4.1 mmols) to instant title product, 0.25 g.; tlc Rf 0.2 (ethyl acetate); $^1$H-nmr (CDCl$_3$) delta: 1.37 (3H, s), 1.63 (3H, s), 1.7–2.1 (4H, complex), 3.3–3.8 (4H, complex), 3.8–4.6 (3H, complex), 4.46 (1H, s), 4.6–4.9 (2H, complex), 5.17 (2H, s), 5.45 (1H, d, J=4 Hz), 7.35 (5H, s).

EXAMPLE C22

Benzyl 6-beta-[S-1-(L-2-(Benzyloxycarbonyl)pyrrolidinocarbonyl)-1-hydroxymethyl]penicillanate The hydrochloride salt of the benzyl ester of L-proline (1 g., 4.1 mmols) was dissolved in 7 ml. H$_2$O, layered with 10 ml. ethyl acetate, and the pH adjusted from 3.0 to 8.0 with 2N NaOH. The aqueous layer was separated and extracted 1×10 ml. fresh ethyl acetate. The organic layers were combined, dried and stripped to yield the free base form of the benzyl ester of L-proline (800 mg.).

Using 1:9 ethyl acetate:CHCl$_3$ as eluant, the method of Example C1 was used to convert title product of Preparation F1 (0.4 g., 1 mmole) and the above free base to instant title product, 0.50 g.; tlc Rf 0.3 (1:9 ethyl acetate:CHCl$_3$); $^1$H-nmr (CDCl$_3$) delta (300 MHz): 1.36 (2.2H, s), 1.38 (0.8H, s), 1.61 (0.8H, s), 1.62 (2.2H, s), 1.8–2.3 (4H, complex), 3.5–4.0 (3H, complex), 4.01 (0.25H, dd, J=4 Hz, 10 Hz), 4.05 (0.75H, dd, J=4 Hz, 10 Hz), 4.49 (0.25H, s), 4.50 (0.75H, s), 4.5–4.8 (1H, complex), 4.87 (0.75H, d, J=10 Hz), 5.18 (0.5H, s), 5.20 (1.5H, s), 5.22 (1.5H, s), 5.23 (0.5H, s), 5.49 (0.75H, d, J=4 Hz), 5.56 (0.25H, d, J=4 Hz), 7.3–7.5 (10H, complex), reflecting an amide conformer mixture in about 1:3 ratio.

EXAMPLE C23

Benzyl 6-beta-[S-1-(N-cyclohexyl-N-methylcarbamoyl)-1-hydroxymethyl]penicillanate Using 1:4 ethyl acetate as eluant, the method of Example C1 was employed to convert title product of Preparation F1 (0.4 g., 1 mmol) and N-methylcyclohexylamine (0.5 ml., 4.1 mmol) to instant title product, 81 mg.; $^1$H-nmr (CDCl$_3$) delta: 1.36 (3H, s), 1.60 (3H, s), 1.0–2.0 (10H, complex), 2.77 (1.5H, s), 2.94 (1.5H, s), 3.9–4.1 (1H, complex), 4.42 (1H, s), 4.5–4.9 (2H, complex), 5.13 (2H, s), 5.43 (1H, d, J=4 Hz), 7.25 (5H, s), reflecting amide conformers in about 1:1 ratio.

EXAMPLE C24

Benzyl 6-beta-[S-1-(N-Benzyl-N-phenylcarbamoyl)-1-hydroxymethyl]penicillanate

Using ethyl acetate as eluant, the method of Example C1 was used to convert title product of Preparation F1 (0.4 g., 1 mmol) and N-phenylbenzylamine (0.75 g., 4.1 mmols) to instant title product, 200 mg.; tlc Rf 0.6 (3:7 ethyl acetate:CHCl$_3$); $^1$H-nmr (CDCl$_3$) delta (300 MHz): 1.40 (3H, s), 1.43 (3H, s), 3.20 (1H, d, J=7 Hz), 4.09 (1H, dd, J=4 Hz, 9 Hz), 4.45 (1H, s), 4.56 (1H, dd), 4.97 (2H, s), 5.24 (2H, s), 5.43 (1H, d, J=4 Hz), 7.1–7.6 (15H, aromatic complex).

EXAMPLE C25

Benzyl 6-beta-[S-1-(N-Benzyl-N-ethylcarbamoyl)-1-hydroxymethyl]penicillanate

Using 1:9 ethyl acetate:CHCl$_3$ as eluant in the procedure of Example C1, title product of Preparation F1 (0.4 g., 1 mmole) and N-ethylbenzylamine (6.1 ml. of 0.67M in THF, 4.1 mmols) were converted to instant title product, 0.50 g.; Rf 0.25 (1:4 ethyl acetate:CHCl$_3$); $^1$H-nmr (CDCl$_3$) delta: 1.06 (1.5H, t), 1.18 (1.5H, t), 1.37 (3H, br.s), 1.45 (1.5H, s), 1.60 (1.5H, s), 3.0–3.8 (3H, complex), 3.9–4.2 (1H, complex), 4.6–5.0 (4H, complex), 5.17 (2H, s), 5.50 (1H, d, J=4 Hz), 7.2–7.4 (10H, aromatic complex), reflecting amide conformers in about 1:1 ratio.

EXAMPLE C26

Benzyl 6-beta-[S-1-(4-Phenylpiperazinocarbonyl)-1-hydroxymethyl]penicillanate

By the procedure of Example C1, using 3:7 ethyl acetate:CHCl$_3$ as eluant, title product of Preparation F1 (0.4 g., 1.03 mmols) and N-phenylpiperazine (neat, 0.63 ml., 4.13 mmols) were converted to instant title product as a dry foam, 0.43 g.; tlc Rf 0.4 (3:7 ethyl acetate:CHCl$_3$), $^1$H-nmr (CDCl$_3$) delta: 1.36 (3H, s), 1.61 (3H, s), 3.0–3.9 (8H, complex), 4.02 (1H, dd, J=4 Hz, 9 Hz), 4.43 (1H, s), 4.9 (1H, dd), 5.14 (2H, s), 5.46 (1H, d, J=4 Hz), 7.2–7.6 (10H, aromatics).

EXAMPLE C27

Benzyl 6-beta-[S-1-(Isoindolinocarbonyl)-1-hydroxymethyl]penicillanate

By the procedure of the preceding Example, title product of Preparation F1 (400 mg., 1.0 mmol) and isoindoline (neat, 0.6 g., 4.1 mmol) were converted to instant, chromatographed crystalline title product, finally recovered by slurry in a small amount of ether and filtration, 0.258 g.; $^1$H-nmr (CDCl$_3$) delta (300 MHz): 1.40 (3H, s), 1.67 (3H, s), 4.15 (1H, dd, J=4 Hz, 10 Hz), 4.7–5.0 (5H, complex), 5.24 (2H, s), 5.58 (1H, d, J=4 Hz), 7.3–7.5 (9H, aromatics).

EXAMPLE C28

Benzyl 6-beta-[S-1-(N-(2-Hydroxyethyl)-N-phenylcarbamoyl)-1-hydroxymethyl]penicillanate Except that the acetic acid quenched reaction mixture was stripped prior to dilution with ethyl acetate and extraction with water, the procedure of Example C26 was used to convert title product of Preparation F1 (0.37 g., 0.956 mmol) and N-(2-hydroxyethyl)aniline (neat, 0.479 ml., 3.824 mmol) to instant, chromatographed title product as an oil, 0.13 g.; tlc Rf 0.35 (3:7 ethyl acetate:CHCl$_3$); $^1$H-nmr (CDCl$_3$) delta 1.36 (3H, s), 1.60 (3H, s), 3.3–4.4 (5H, complex), 4.42 (1H, s), 4.6–4.8 (2H, complex), 5.13 (2H, s), 5.35 (1H, d, J=4 Hz), 6.6–7.4 (10H, aromatics).

EXAMPLE C29

Benzyl 6-beta-[S-1-(N-(Ethoxycarbonylmethyl)-N-benzylcarbamoyl)-1-hydroxymethyl]penicillanate By the method of Example C1, title product of Preparation F1 (0.387 g., 1 mmol) and N-benzylglycine ethyl ester (7.7 ml., 4.1 mmol) were converted to instant title product, chromatographed using 1:9 ethyl acetate:CHCl$_3$ as eluant, 0.371 g.; tlc Rf 0.5 (3:7 ethyl acetate:CHCl$_3$); $^1$H-nmr (CDCl$_3$) delta: 1.22 (3H, t), 1.37 (3H, br.s), 1.52 (1.5H, s), 1.58 (1.5H, s), 3.2 (1H, br.s), 3.8–4.3 (5H, complex), 4.41 (1H, s), 4.8 (2H, complex), 5.12 (2H, s), 5.46 (1H, overlapping doublets), 7.2–7.4 (10H, aromatics), representing amide conformers in about 1:1 ratio.

EXAMPLE C30

Benzyl 6-beta-[S-1-(N-(Dimethylcarbamoylmethyl)-N-benzylcarbamoyl)-1-hydroxymethyl]penicillanate By the method of Example C1, employing ethyl acetate as eluant, title product of Example F1 (0.387 g., 1 mmol) and 2-benzylamino-N,N-dimethylacetamide (0.8 g., 4.1 mmols) were converted to instant title product, 0.232 g.; tlc Rf 0.3 (ethyl acetate); $^1$H-nmr (CDCl$_3$) delta (representing amide conformers in about 3:4 ratio): 1.36 (3H, s), 1.53 (1.7H, s), 1.60 (1.3H, s), 2.85 (1.3H, s), 2.90 (4.5H, br.s), 3.8–4.3 (5H, complex), 4.42 (1H, s), 4.6–5.0 (2H, complex), 5.16 (2H, s), 5.50 (1H, overlapping doublets), 7.3–7.4 (10H, aromatics).

EXAMPLE C31

Benzyl 6-beta-[S-(1-(N-Methyl-N-(4-methylphenyl)carbamoyl)-1-hydroxymethyl]penicillanate By the method of the Example C1, eluting with 1:4 ethyl acetate:CHCl$_3$, title product of Preparation F1 (0.8, 2.07 mmols) and N-methyl-p-toluidine (1 g., 8.27 mmols) were converted to instant title product 0.58 g., $^1$H-nmr (CDCl$_3$) delta (300 MHz): 1.37 (3H, s), 1.45 (3H, s), 2.40 (3H, s), 3.30 (3H, s), 4.03 (1H, dd, J=4 Hz, 10 Hz), 4.41 (1H, s), 4.56 (1H, overlapping doublets), 5.19 (2H, s), 5.34 (1H, d, J=4 Hz), 7.25 (5H, s), 7.40 (4H, s).

EXAMPLE C32

Benzyl 6-beta-[S-1-(N-(Methylcarbamoylmethyl)-N-benzylcarbamoyl)-1-hydroxymethyl)penicillanate By the method of Example C30, title product of Preparation F1 (3.87 g., 1 mmol) and 2-benzylamino-N-methylacetamide (1 g., 5.2 mmols) were converted to instant title product, 0.34 g.; $^1$H-nmr (CDCl$_3$) delta (representing amide conformers in about 1:1 ratio): 1.36 (3H, s), 1.49 (1.5H, s), 1.56 (1.5H, s), 2.68 (3H, d), 3.6–4.4 (4H, complex), 4.43 (1H, s), 4.6–5.1 (3H, complex), 5.18 (2H, s), 5.52 (1H, overlapping doublets), 6.4 (1H, complex), 7.2–7.3 (10H, aromatics).

EXAMPLE C33

Benzyl 6-beta-[S-1-(N-Methyl-N-(4-methoxyphenyl)carbamoyl)-1-hydroxymethyl]penicillanate By the method of Example C26, title product of Preparation F1 (0.8 g., 2.07 mmols) and N-methyl-p-anisidine (1.13 g., 8.26 mmols) were converted to instant, chromatographed title product, 0.63 g.; $^1$H-nmr (CDCl$_3$) delta (300 MHz); 1.37 (3H, s), 1.46 (3H, s), 3.29 (3H, s), 3.86 (3H, s), 4.02 (1H, dd, J=4 Hz, 10 Hz), 4.41 (1H, s), 4.53 (1H, overlapping doublets), 5.19 (2H, s), 5.35 (1H, d, J=4 Hz), 7.12 (4H, ABq), 7.40 (5H, s).

EXAMPLE C34

Benzyl
6-beta-[S-1-(4-(2-Pyridyl)piperazinocarbonyl)-1-hydroxymethyl]penicillanate By the method of Example C19, title product of Preparation F1 (0.8 g., 2.07 mmols) and N-(2-pyridyl)piperazine (1.35 g., 8.26 mmols) were converted to instant, chromatographed title product, 0.5 g.; mp 144°-146°; tlc Rf 0.3 (1:1 ethyl acetate:CHCl$_3$); $^1$H-nmr (CDCl$_3$) delta: 1.37 (3H, s), 1.62 (3H, s), 3.4-3.8 (8H, complex), 4.01 (1H, dd, J=4 Hz, 9 Hz), 4.42 (1H, s), 4.97 (1H, d, J=9 Hz), 5.15 (2H, s), 5.46 (1H, d, J=4 Hz), 6.6 (2H, complex), 7.3 (5H, s), 7.5 (1H, complex), 8.15 (1H, complex).

EXAMPLE C35

Benzyl
6-beta-[S-1-(Indolinocarbonyl)-1-hydroxymethyl]penicillanate

By the method of Example C26, except to recover a portion of the indoline as a crystalline salt on stripping prior to chromatography, title product of Preparation F1 (0.8 g., 2.07 mmols) and indoline (9.2 ml. of 0.89M in THF, 8.2 mmols) were converted to instant, chromatographed title product, 0.100 g.; tlc Rf 0.65 (3:7 ethyl acetate:CHCl$_3$); $^1$H-nmr (CDCl$_3$) delta (300 MHz): 1.40 (3H, s), 1.67 (3H, s), 3.06 (2H, complex), 4.0-4.5 (4H, complex), 4.56 (1H, s), 4.89 (1H, d, J=9 Hz), 5.24 (2H, s), 5.62 (1H, d, J=4 Hz), 7.0-7.5 (8H, complex), 8.19 (1H, d, J=8 Hz).

EXAMPLE C36

Benzyl
6-beta-[S-1-(N-(Pyrrolidinocarbonylmethyl)-N-benzylcarbamoyl)-1-hydroxymethyl]penicillanate By the method of Example C24, title product of Preparation F1 (0.42 g., 1.1 mmols) and N-[2-(benzylamino)acetyl]pyrrolidine (0.95 g., 4.3 mmols) were converted to instant, chromatographed title product, 0.317 g.; tlc Rf 0.5 (ethyl acetate); $^1$H-nmr (CDCl$_3$) delta (300 MHz) (representing the two amide rotamers in 6:7 ratio): 1.35 (1.6H, s), 1.37 (1.4H, s), 1.50 (1.6H, s), 1.60 (1.4H, s), 1.7-2.0 (4H, complex), 3.0-3.5 (4H, complex), 3.69 (0.5H, d, J=17 Hz), 4.0-4.2 (2H, complex), 4.37 (0.5H, d, J=15 Hz), 4.46 (0.54H, s), 4.47 (0.46H, s), 4.67 (0.5H, d, J=17 Hz), 4.80 (0.5H, d, J=10 Hz), 4.91 (1H, complex), 5.17 (1.1H, s), 5.18 (0.9H, s), 5.54 (0.54H, d, J=4 Hz), 5.57 (0.46H, d, J=4 Hz), 7.2-7.5 (10H, complex).

EXAMPLE C37

Benzyl
6-beta-[S-1-(N-Benzyl-N-isopropylcarbamoyl)-1-hydroxymethyl]penicillanate By the method of Example C20, title product of Example F1 (0.8 g., 2.06 mmols) and N-benzyliosropylamine (0.718 ml., 4.13 mmols) were converted to instant chromatographed title product, 0.31 g.; $^1$H-nmr (CDCl$_3$) delta (300 MHz) (reflecting two amide conformers in 5:6 ratio): 1.14 (1.6H, d, J=7 Hz), 1.19 (2.7H, br.d, J=7 Hz), 1.23 (1.6H, d, J=7 Hz), 1.38 (1.4H, s), 1.42 (1.6H, s), 1.44 (1.4H, s), 1.67 (1.6H, s), 2.98 (1H, complex), 4.06 (0.45H, dd, J=4 Hz, 9 Hz), 4.11 (0.55H, dd, J=4 Hz, 10 Hz), 4.4 (4H, complex), 4.9-5.1 (1H, complex), 5.21 (0.9H, s), 5.23 (1.1H, s), 5.49 (0.45H, d, J=4 Hz), 5.55 (0.55H, d, J=4 Hz), 7.2-7.5 (10H, complex).

EXAMPLE C38

Benzyl
6-beta-[S-1-(N-(2-(2-Pyridyl)ethyl)-N-methylcarbamoyl)-1-hydroxymethyl]penicillanate By the method of Example C1, using 1:49 methanol:ethyl acetate as eluant, title product of Example F1 (0.8 g., 2.06 mmols) and 2-(2-methylaminoethyl)pyridine (1.14 ml., 4.13 mmols) were converted to instant title product, 0.7 g.; $^1$H-nmr (CDCl$_3$) delta (300 MHz) (reflecting two amide conformers in 3:4 ratio): 1.46 (3H, s), 1.62 (3H, s), 2.89 (1.7H, s), 3.08 (1.3H, s), 2.9-3.2 (2H, complex), 3.73 (1.2H, complex), 4.08 (1.8H, complex), 4.47 (0.43H, s), 4.48 (0.57H, s), 4.83 (0.43H, d, J=9 Hz), 5.04 (0.57H, d, J=10 Hz), 5.20 (2H, s), 5.48 (0.43H, d, J=4 Hz), 5.52 (0.57H, d, J=4 Hz), 7.1-8.6 (9H, aromatics).

EXAMPLE C39

Benzyl
6-beta-[S-1-(N-(Ethoxycarbonylmethyl)-N-methylcarbamoyl)-1-hydroxymethyl]penicillanate By the method of Example C23, title product of Preparation F1 (0.611 g., 1.6 mmol) and sarcosine ethyl ester (5.5 ml. of 0.57M in THF, 6.3 mmols) were converted to instant, chromatographed title product, 0.59 g.; tlc Rf 0.25 (3:7 ethyl acetate:CHCl$_3$); $^1$H-nmr (CDCl$_3$) delta (300 MHz) (reflecting the two amide conformers in 3:5 ratio): 1.27 (3H, t), 1.38 (3H, br.s), 1.60 (1.1H, s), 1.64 (1.9H, s), 3.00 (1.1H, s), 3.24 (1.9H, s), 3.92 (0.6H, d, J=18 Hz), 4.0-4.4 (5H, complex), 4.46 (0.4H, s), 4.49 (0.6H, s), 4.80 (0.4H, d, J=10 Hz), 4.95 (0.6H, d, J=9 Hz), 5.20 (2H, s), 5.51 (0.6H, d, J=4 Hz), 5.55 (0.4H, d, J=4 Hz), 4.4 (5H, s).

EXAMPLE C40

Benzyl
6-beta-[S-1-(N-(Pyrrolidinocarbonylmethyl)-N-methylcarbamoyl)-1-hydroxymethyl]penicillanate By the method of Example C19, title product of Preparation F1 (600 mg., 1.6 mmol) and N-[2-(methylamino)acetyl]pyrrolidine (0.88 g., 6.2 mmols) were converted to instant chromatographed title product, 0.20 g.; tlc Rf 0.6 (3:2 ethyl acetate:CHCl$_3$); $^1$H-nmr (CDCl$_3$) delta (reflecting the two amide conformers in 2:1 ratio): 1.35 (3H, s), 1.60 (3H, s), 1.86 (4H, complex), 2.95 (1H, s), 3.22 (2H, s), 3.40 (4H, complex), 3.9-4.3 (3H, complex), 4.40 (0.3H, s), 4.42 (0.7H, s), 4.8 (1H, overlapping doublets), 5.15 (2H, s), 5.44 (1H, overlapping doublets), 7.3 (5H, s).

EXAMPLE C41

Benzyl
6-beta-[S-1-(N,N-bis-(Ethoxycarbonylmethyl)carbamoyl)-1-hydroxymethyl]penicillanate By the method of Example C23, title product of Example F1 (600 mg., 1.6 mmols) and diethyl iminodiacetate (1.2 g., 6.2 mmols) were converted to instant chromatographed title product, 0.30 g.; $^1$H-nmr (CDCl$_3$)

delta (300 MHz): 1.30 (6H, complex), 1.39 (3H, s), 1.64 (3H, s), 4.0–4.7 (10H, complex), 4.92 (1H, d, J=10 Hz), 5.22 (2H, s), 5.55 (1H, d, J=4 Hz), 7.42 (5H, s).

EXAMPLE C42

Benzyl 6-beta-[S-1-(N-(Dimethylcarbamoylmethyl)-N-methylcarbamoyl)-1-hydroxymethyl]penicillanate By the method of Example C1, using 1:19 methanol:ethyl acetate as eluant, title product of Preparation F1 (600 mg., 1.6 mmols) and 2-(methylamino)-N,N-dimethylacetamide (0.72 g., 6.2 mmols) were converted to instant title product, 0.50 g.; tlc Rf 0.5 (1:9 methanol:ethyl acetate); $^1$H-nmr (CDCl$_3$) delta (reflecting the two amide conformers in about 1:2 ratio): 1.36 (3H, s), 1.61 (3H, s), 2.93 (7H, br.s), 3.17 (2H, s), 3.8–4.3 (3H, complex), 4.35 (1H, br.s), 4.65 (0.3H, d, J=10 Hz), 4.84 (0.7H, d, J=10 Hz), 5.11 (2H, s), 5.40 (1H, overlapping doublets), 7.3 (5H, s).

EXAMPLE C43

Benzyl 6-beta-[S-1-(N-(Methylcarbamoylmethyl)-N-methylcarbamoyl)-1-hydroxymethyl]penicillanate By the procedure of Example C1, using 1:9 methanol:ethyl acetate as eluant, title product of Preparation F1 (600 mg., 1.6 mmols) 2-(methylamino)-N-methylacetamide (0.63 g., 6.2 mmols) were converted to instant title product, 0.50 g.; tlc Rf 0.55 (1:9 methanol:ethyl acetate); $^1$H-nmr (CDCl$_3$) delta (reflecting the amide conformers in about 2:3 ratio): 1.38 (3H, s), 1.62 (3H, br. s), 2.74 (3H, br.d), 2.93 (1.2H, s), 3.20 (1.8H, s), 3.8–4.2 (3H, complex), 4.43 (1H, s), 4.85 (1H, br.d), 5.13 (2H, s), 5.45 (1H, overlapping doublets), 6.47 (0.6H, br.d), 6.74 (0.4H, br.d), 7.3 (5H, s).

EXAMPLE C44

Benzyl 6-beta-[S-1-(N-(Carbamoylmethyl)-N-methylcarbamoyl)-1-hydroxymethyl]penicillanate By the method of the preceding Example, title product of Preparation F1 (516 mg., 1.3 mmols) and 2-(methylamino)acetamide (0.47 g., 5.3 mmols) were converted to instant title product, 0.32 g.; tlc Rf 0.45 (1:10 methanol:ethyl acetate); $^1$H-nmr (CDCl$_3$) delta (300 MHz) (reflecting the two amide conformers in 2:3 ratio): 1.35 (1.2H, s), 1.36 (1.8H, s), 1.59 (1.2H, s), 1.62 (1.8H, s), 2.97 (1.2H, s), 3.23 (1.8H, s), 3.71 (0.6H, d, J=16 Hz), 3.90 (0.4H, d, J=18 Hz), 4.05 (1H, complex), 4.28 (0.6H, d, J=16 Hz), 4.41 (0.4H, d, J=18 Hz), 4.46 (0.4H, s), 4.49 (0.6H, s), 4.86 (1H, complex), 5.18 (2H, s), 5.49 (0.6H, d, J=4 Hz), 5.54 (0.4H, d, J=4 Hz), 6.51 (0.6H, br.s), 6.62 (0.6H, br.s), 6.20 (0.4H, br.s), 6.86 (0.4H, br.s), 7.38 (5H, s).

EXAMPLE C45

Benzyl 6-beta-[R-1-(N-Methyl-N-phenylcarbamoyl)-1-hydroxymethyl]penicillanate

By the method of Example C23, title product of Example F2 (0.8 g., 2.06 mmols) and N-methylaniline (0.89 ml., 8.26 mmols) were converted to instant title product, 0.43 g.; tlc Rf 0.35 (1:4 ethyl acetate:CHCl$_3$); $^1$H-nmr (CDCl$_3$) delta (300 MHz) (reflecting the 2 amide conformers in 2:3 ratio): 1.26 (3H, s), 1.34 (3H, s), 3.37 (3H, s), 3.80 (1H, dd, J=4 Hz, 8 Hz), 4.37 (1H, s), 4.73 (1H, t), 5.20 (2H, s), 5.48 (1H, d, J=4 Hz), 7.3–7.5 (10H, aromatics).

EXAMPLES C46-C78

Using the method of Examples C1-C45 above, the following additional compounds were prepared. Shown in sequence is the Example No., the compound prepared, chromatography eluant, the amount prepared, its physical properties, and the starting materials and amounts thereof.

C46. Benzyl 6-beta-[S-1-(S-2-(methoxycarbonyl)pyrrolidinocarbonyl)-1-hydroxymethyl]penicillanate; 3:7 ethyl acetate:CHCl$_3$, 0.52 g.; $^1$H-nmr (CDCl$_3$) delta (ppm) 1.35 (3H, s), 1.63 (3H, s), 1.8–2.3 (4H, complex), 3.70 (3H, s), 3.7–4.0 (3H, complex), 4.06 (1H, dd, J=4 Hz, 10 Hz), 4.45 (1H, s), 4.82 (1H, d, J=10 Hz), 5.18 (2H, s), 5.48 (1H, d, J=4 Hz), 7.40 (5H, s); product of Preparation F1 (0.60 g.; 0.0016 mol) and L-proline methyl ester (0.80 g., 0.0062 mol).

C47. Benzyl 6-beta-[S-1-(N-(carbamoylmethyl)-N-benzylcarbamoyl)-1-hydroxymethyl]penicillanate; ethyl acetate; 0.31 g.; $^1$H-nmr (CDCl$_3$) delta (reflecting two rotamers in about 1:1 ratio) 1.33 (3H, br. s), 1.43 (1.5H, s), 1.56 (1.5H, s), 3.4–4.3 (3H, complexes), 4.38 (1H, s), 4.6–5.1 (complexes), 5.13 (2H, s), 5.43 (0.5H, d, J=4 Hz), 5.52 (0.5H, d, J=4 Hz), 6.1–6.8 (2H, complex), 7.2–7.4 (10H, aromatics); product of Preparation F1 (0.60 g., 0.0016 mol) and 2-(benzylamino)-acetamide (1.0 g., 0.0062 mol).

C48. Benzyl 6-beta-[S-1-(N,N-di(N-methylcarbamoylmethyl)carbamoyl)-1-hydroxymethyl]penicillanate; 7:93 methanol:ethyl acetate; 0.15 g.; tlc Rf 0.25 (1:9 methanol:ethyl acetate); $^1$H-nmr (CDCl$_3$) delta (300 MHz) 1.35 (3H, s), 1.58 (3H, s), 2.80 (6H, m), 3.69 (1H, d, J=16 Hz), 3.9–4.2 (3H, complex), 4.46 (1H, s), 4.6–4.8 (2H, complex), 5.18 (2H, s), 5.45 (1H, d, J=4 Hz), 7.40 (5H, s), 7.52 (1H, m), 8.80 (1H, m); product of Preparation F1 (0.60 g., 0.0016 mol) and di(N-methylcarbamoylmethyl)amine (1.0 g., 0.0064 mol).

C49. Benzyl 6-beta-[S-1-(N-ethyl-N-phenylcarbamoyl)-1-hydroxymethyl]penicillanate, 1:4 ethyl acetate:CHCl$_3$; 0.39; tlc Rf 0.15 (1:4 ethyl acetate:CHCl$_3$), Rf 0.6 (1:1 ethyl acetate:CHCl$_3$); $^1$H-nmr (CDCl$_3$) delta (300 MHz) 1.16 (3H, t), 1.37 (3H, s), 1.44 (3H, s), 3.6–4.0 (2H, m), 4.02 (1H, dd, J=4, 10 Hz), 4.42 (1H, s), 4.48 (1H, d, J=10 Hz), 5.20 (2H, s), 5.33 (1H, d, J=4 Hz), 7.3–7.5 (9H, complex); product of Preparation F1 (0.80 g., 0.0021 mol) and N-ethylaniline (1.04 ml., 0.0083 mol).

C50. Benzyl 6-beta-[S-1-(1,2,3,4-tetrahydroquinolinocarbonyl)-1-hydroxymethyl]penicillanate; CHCl$_3$; tlc Rf 0.55 (3:7 ethyl acetate:CHCl$_3$; $^1$H-nmr (CDCl$_3$) delta (300 MHz) 1.28 (6H, s), 1.36 (1H, m), 1.62 (1H, m), 1.87 (1H, m), 2.13 (1H, m), 2.78 (2H, complex), 3.39 (1H, m), 3.69 (1H, m), 4.13 (1H, dd, J=4 Hz, 10 Hz), 4.25 (1H, m), 4.42 (1H, s), 5.00 (1H, br. d), 5.16 (2H, s), 5.33 (1H, m), 7.1–7.6 (9H, aromatics); product of Preparation F1 (1.0 g., 0.0026 mol) and 1,2,3,4-tetrahydroquinoline (1.2 ml., 1.3 g., 0.010 mol).

C51. Benzyl 6-beta-[S-1-(N-ethyl-N-(4-benzyloxyphenyl)carbamoyl)-1-hydroxymethyl]penicillanate; 1:9 hexane:CHCl$_3$; 0.40 g., $^1$H-nmr (CDCl$_3$) delta (300 MHz) 1.12 (3H, t), 1.35 (3H, s), 1.42 (3H, s), 3.10 (1H, br. s), 3.64 (1H, m), 3.78 (1H, m), 4.02 (1H, dd, J=4 Hz, 10 Hz), 4.40 (1H, s), 4.44 (1H, d, J=10 Hz), 5.10 (2H, s), 5.17 (2H, s), 5.36 (1H, d, J=4 Hz), 7.0–7.5 (14H, aromatics); product of Preparation F1 (0.80 g., 0.0021 mol)

and N-[4-(benzyloxy)phenyl]ethylamine (1.87 g., 0.0083 mol).

C52. Benzyl 6-beta-[S-1-(N-ethyl-N-(3-benzyloxyphenyl)carbamoyl)-1-hydroxymethyl]penicillanate; CHCl$_3$, then 1:9 ethyl acetate:CHCl$_3$ (twice chromatographed); 0.11 g., ; $^1$H-nmr (CDCl$_3$) delta (300 MHz); 1.15 (3H, s), 1.37 (3H, s), 1.46 (3H, s), 2.80 (1H, br.d), 3.6-3.9 (2H, m), 4.00 (1H, dd, J=4 Hz, 10 Hz), 4.42 (1H, s), 4.52 (1H, m), 5.11 (2H, s), 5.20 (2H, s), 5.33 (1H, d, J=4 Hz), 6.9-7.5 (14H, aromatics); product of Preparation F1 (0.80 g., 0.0021 mol) and N-[3-(benzyloxy)phenyl]ethylamine (1.87 g., 0.0083 mol).

C53. Benzyl 6-Beta-[S-1-(1-(methoxycarbonyl)isoindolinocarbonyl)-1-hydroxymethyl]penicillanate; 1:9 ethyl acetate:CHCl$_3$; tlc Rf 0.4 (1:9 ethyl acetate:CHCl$_3$); $^1$H-nmr (CDCl$_3$) delta (300 MHz), reflecting C-1 isoindolino diastereoisomers and two amide rotamers of one of those isomers in near equal amounts, 1.36 (1.7H, s), 1.39 (1.3H, s), 1.62 (2.1H, br.s), 1.67 (0.9H, s), 3.74 (1H, s), 3.76 (2H, s), 4.0-4.2 (1H, complex), 4.47 (0.26H, s), 4.50 (0.46H, s), 4.51 (0.28H, s), 4.8-5.4 (3H, overlapping multiplets), 5.20 (2H, s), 5.56 (0.8H, complex), 5.60 (0.2H, d, J=4 Hz), 5.65 (0.26H, br, s), 5.73 (0.46H, br.s), 6.26 (0.23H, br.s), 7.3-7.5 (9H, aromatic complex); product of Preparation F1 (0.40 g., 0.001 mol) and methyl isoindoline-1-carboxylate (0.49 g., 0.0028 mol).

C54. Benzyl 6-beta-[S-1-(N-(N-isopropylcarbamoylmethyl)-N-benzyl)carbamoyl-1-hydroxymethyl]penicillanate; 3:7 ethyl acetate:CHCl$_3$; 0.34 g.; tlc Rf 0.3 (1:1 ethyl acetate:CHCl$_3$); $^1$H-nmr (CDCl$_3$) delta (300 MHz), revealing amide conformers in about 1:1 ratio, 0.9-1.1 (6H, complex), 1.30 (1.5H, s), 1.31 (1.5H, s), 1.43 (1.5H, s), 1.52 (1.5H, s), 3.6-4.2 (5.5H, complex), 4.40 (1H, s), 4.5-5.1 (2.5H, complex), 5.14 (2H, s), 5.49 (0.5H, d, J=4 Hz), 5.53 (0.5H, d, J=4 Hz), 5.95 (0.5H, br.d, J=8 Hz), 6.03 (0.5H, br.d, J=8 Hz), 7.1-7.4 (10H, complex); product of Preparation F1 (0.60 g., 0.0016 mol) and 2-(benzylamino)-N-isopropylacetamide (1.2 g., 0.0064 mol).

C55. Benzyl 6-beta-[S-1-(S-2-(carbamoyl)pyrrolidinocarbonyl)-1-hydroxymethyl]penicillanate; ethyl acetate; 0.26 g.; tlc Rf 0.7 (ethyl acetate); $^1$H-nmr (CDCl$_3$) delta (300 MHz), 1.37 (3H, s), 1.61 (3H, s), 1.97 (2H, m), 2.2-2.5 (2H, complex), 3.56 (2H, complex), 4.06 (1H, dd, J=4Hz, 10 Hz), 4.31 (1H, t), 4.54 (1H, s), 5.18 (2H, s) 5.12 (1H, d, J=10 Hz), 5.72 (1H, d, J=4 Hz), 7.37 (5H, s); product of Example F1 (0.60 g., 0.0016 mol) and L-prolinamide (0.73 g., 0.0064 mol).

C56. Benzyl 6-beta-[S-1-(S-2-(N-methylcarbamoyl)-pyrrolidinocarbonyl)-1-hydroxymethyl]penicillanate; ethyl acetate; 0.26 g.; tlc Rf 0.2 (ethyl acetate); $^1$H-nmr (CDCl$_3$) delta (300 MHz), reflecting amide rotamers in 1:3 ratio, 1.35 (0.75H, s), 1.37 (2.25H, s), 1.58 (0.75H, s), 1.61 (2.25H, s), 1.8-2.1 (4H, complex), 2.75 (3H, d), 3.5-4.0 (2H, complex), 4.05 (1H, dd, J=4 Hz, 10 Hz), 4.44 (0.25H, s), 4.48 (0.75H, s), 4.5-4.8 (3H, complex), 5.19 (2H, s), 5.50 (1H, d, J=4 Hz), 6.69 (0.25H, d), 6.91 (0.75H, d), 7.38 (5H, s); product of Preparation F1 (0.60 g., 0.0016 mol) and N-methyl-L-prolinamide (0.82 g., 0.0064 mol).

C57. Benzyl 6-beta-[S-1-(N,N-di(pyrrolidinocarbonylmethyl)carbamoyl-1-hydroxymethyl]penicillanate; 1:19 CH$_3$OH:ethyl acetate; 0.40 g.; $^1$H-nmr (CDCl$_3$) delta (300 MHz), 1.35 (3H, s), 1.60 (3H, s), 1.7-2.1 (8H, complex), 3.3-3.5 (8H, complex), 4.07 (1H, dd, J=4 Hz, 10 Hz), 4.10 (2H, ABq), 4.46 (1H, s), 4.51 (2H, ABq), 4.79 (1H, d, J=10 Hz), 5.18 (1H, s), 5.51 (1H, d, J=4 Hz), 7.37 (5H, s); product of Preparation F1 (0.60 g., 0.0016 mol) and di(pyrrolidinocarbonylmethyl)amine.

C58. Benzyl 6-beta-[S-1-[N-(4-(2-hydroxyethyl)-piperazinocarbonylmethyl)-N-benzylcarbamoyl]-1-hydroxymethyl]penicillanate; 3:17 CH$_3$OH:ethyl acetate; 19 mg.; $^1$H-nmr (CDCl$_3$) delta (300 MHz), reflecting two amide conformers in 1:2 ratio, 1.41 (2H, s), 1.43 (1H, s), 1.66 (2H, s), 1.68 (1H, s), 2.4-2.7 (4H, overlapping multiplets), 3.0-3.2 (2H, m), 3.5-3.8 (4H, overlapping multiplets), 3.86 (2H, d), 3.90 (0.33H, dd, J=4 Hz, 10 Hz), 4.06 (0.67H, dd, J=4 Hz, 10 Hz), 4.30 (1.3H, t), 4.50 (0.67H, s), 4.55 (0.33H, s), 4.80 (0.33H, d, J=10 Hz), 4.88 (0.67H, d, J=10 Hz), 5.22 (2H, s), 5.52 (0.33H, d, J=4 Hz), 5.55 (0.67H, d, J=4 Hz), 7.3-7.5 (10H, aromatics); product of Preparation F1 (0.60 g., 0.0016 mol) and N-[4-(2-hydroxyethyl)piperazinocarbonylmethyl]benzylamine (1.7 g., 0.0062 mol).

C59. Benzyl 6-beta-[S-1-(4-(N-isopropylcarbamoylmethyl)piperazino)carbonyl-1-hydroxymethyl]penicillanate; 1:49 CH$_3$OH:ethyl acetate; 0.282 g.; tlc Rf 0.45 (1:9 CH$_3$OH: ethyl acetate) $^1$H-nmr (CDCl$_3$) delta, 1.16 (6H, d, J=8 Hz), 1.36 (3H, s), 1.60 (3H, s), 2.4-2.6 (4H, complex), 3.01 (2H, s), 3.6-3.8 (5H, complex), 4.03 (1H, dd, J=4 Hz, 10 Hz), 4.45 (1H, s), 4.85 (1H, d, J=10 Hz), 5.20 (2H, s), 5.32 (1H, d, J=4 Hz), 6.89 (1H, d, J=8 Hz), 7.38 (5H, s); product of Preparation F1 (0.60 g.) and 1-(N-isopropylcarbamoylmethyl)piperazine (1.14 g., 0.0062 mol).

C60. Benzyl 6-beta-[S-1-(2,6-dimethylmorpholinocarbonyl)-1-hydroxymethyl]penicillanate; 3:7 ethyl acetate:CHCl$_3$; 0.26 g.; tlc Rf 0.25 (3:7 ethyl acetate:CHCl$_3$); $^1$H-nmr (CDCl$_3$) delta (300 MHz), reflecting two isomers in 1:1 ratio, possibly the amide rotamers of a single meso-2,6-dimethylmorpholine isomer, 1.16 (6H, d), 1.34 (3H, s), 1.61 (3H, s), 2.36 (1H, t), 2.7-3.0 (1H, complex), 3.4-3.7 (2H, complex), 3.9-4.1 (2H, complex), 4.30 (1H, t), 4.44 (1H, s), 4.78 (0.5H, d, J=10 Hz), 4.86 (0.5H, d, J=11 Hz), 5.18 (2H, s), 5.50 (1H, d, J=4 Hz), 7.37 (5H, s); product of Preparation F1 (0.60 g., 0.0016 mol) and 2,6-dimethylmorpholine (commercial "mixture of isomers"; 0.79 ml., 0.74 g., 0.0064 mol).

C61. Benzyl 6-beta-[S-1-(N-(N-ethylcarbamoylmethyl)-N-benzylcarbamoyl)-1-hydroxymethyl]penicillanate; 3:7 ethyl acetate:CHCl$_3$; 0.2 g.; tlc Rf 0.4 (1:1 ethyl acetate:CHCl$_3$); $^1$H-nmr (CDCl$_3$) delta (300 MHz), reflecting two amide rotamers in 1:1 ratio, 1.00 (1.5H, t), 1.06 (1.5H, t), 1.36 (3H, s), 1.48 (1.5H, s), 1.57 (1.5H, s), 3.0-3.3 (2H, complex), 3.78 (1.5H, d, J=16 Hz), 3.9-4.3 (4H, complex), 4.46 (1H, s), 4.62 (0.5H, d, J=16 Hz), 4.8-5.15 (3H, complex), 5.20 (2H, s), 5.55 (0.5H, d, J=4 Hz), 5.60 (0.5H, d, J=4 Hz), 6.30 (0.5H, t), 6.44 (0.5H, t), 7.2-7.4 (10H, complex); the product of Preparation F1 (0.60 g., 0.0016 mol) and 2-(benzylamino)-N-ethylacetamide (1.2 g., 0.0064 mol).

C62. Benzyl 6-beta-[S-1-(N-(1-methyl-4-piperidyl)-N-methylcarbamoyl)-1-hydroxymethyl]penicillanate; 1:3 CH$_3$OH:ethyl acetate; 0.162 g.; tlc Rf 0.1 (1:1 CH$_3$OH:ethyl acetate); $^1$H-nmr (CDCl$_3$) delta (300 MHz), reflecting two amide rotamers in about 3:5 ratio, 0.8-1.0 (2H, complex), 1.1-1.2 (2H, complex), 1.36 (3H, s), 1.62 (3H, br.s), 1.5-2.1 (4H, complex), 2.26 (1.9H, s), 2.28 (1.1H, s), 2.82 (1.1H, s), 2.92 (2H, complex), 3.01 (1.9H, s), 4.03 (1H, complex), 4.47 (1H, s), 4.80 (0.6H, d, J=10 Hz), 4.85 (0.4H, d, J=10 Hz), 5.18 (2H, s), 5.48 (0.6H, d, J=4 Hz), 5.50 (0.4H, d, J=4 Hz), 7.37 (5H, s); product of Preparation F1 (0.60 g., 0.0016 mol) and 1-methyl-4-(methylamino)piperidine (0.82 g., 0.0064 mol).

C63. Benzyl 6-beta-[S-1-(N-(2-morpholinoethyl)-N-benzylcarbamoyl)-1-hydroxymethyl]penicillanate; ethyl acetate; 0.166 g.; tlc Rf 0.3 (ethyl acetate; $^1$H-nmr (CDCl$_3$) delta (300 MHz), reflecting two amide conformers in 1:4 ratio, 1.35 (0.6H, s), 1.38 (2.4H, s), 1.46 (0.6H, s), 1.60 (2.4H, s), 2.3–2.7 (6H, complex), 3.1–4.4 (1H, complex), 4.5–4.8 (5H, complex), 4.08 (0.8H, d), 4.14 (1H, dd, J=4 Hz, J=10 Hz), 4.41 (0.2H, s), 4.49 (0.8H, s), 4.89 (0.8H, d), 5.18 (2H, s), 5.52 (0.2H, d, J=4 Hz), 5.58 (0.8H, d, J=4 Hz), 7.2–7.5 (10H, complex); product of Preparation F1 (0.43 g., 0.0011 mol) and N-(2-morpholinoethyl)benzylamine (0.85 g., 0.0038 mol).

C64. Benzyl 6-beta-[S-1-(4-(2-hydroxyethyl)-piperazinocarbonyl)-1-hydroxymethyl]penicillanate; 3:7 ethyl acetate:CHCl$_3$, 1:19 CH$_3$OH:ethyl acetate (twice chromatographed); 0.14 g.; tlc Rf 0.6 (1:1 CH$_3$OH:ethyl acetate); $^1$H-nmr (CDCl$_3$) delta (300 MHz) 1.37 (3H, s), 1.62 (3H, s), 2.4–2.7 (6H, complex), 3.24 (2H, br.s), 3.5–3.9 (6H, complex), 4.03 (1H, dd, J=4 Hz, 10 Hz), 4.46 (1H, s), 4.86 (1H, d, J=10 Hz), 5.20 (2H, s), 5.51 (1H, d, J=4 Hz), 7.4 (5H, s); product of Preparation F1 (0.70 g., 0.0018 mol) and 1-(2-hydroxyethyl)piperazine (0.94 g., 0.0072 mol).

C65. Benzyl 6-beta-[S-1-(4-benzylpiperazinocarbonyl)-1-hydroxymethyl]penicillanate; ethyl acetate; 0.346 g.; tlc Rf 0.65 (ethyl acetate); $^1$H-nmr (CDCl$_3$) delta (300 MHz) 1.41 (3H, s), 1.66 (3H, s), 2.4–2.6 (4H, complex), 3.5–3.8 (4H, complex), 4.07 (1H, dd, J=4 Hz, 10 Hz), 4.51 (1H, s), 4.90 (1H, d, J=10 Hz), 5.24 (2H, s), 5.56 (1H, d, J=4 Hz), 7.3–7.5 (10H, aromatics); product of Preparation F1 (0.60 g., 0.0016 mol) and N-benzylpiperazine (1.1 ml., 1.1 g., 0.0064 mol).

C66. Benzyl 6-beta-[S-1-(N-(N-ethylcarbamoylmethyl)-N-ethylcarbamoyl)-1-hydroxymethyl]penicillanate; 7:3 ethyl acetate:CHCl$_3$; 0.13 g.; tlc Rf 0.35 (ethyl acetate); $^1$H-nmr (CDCl$_3$) delta (300 MHz), reflecting two amide rotamers in about 3:5 ratio, 1.12 (3H, overlapping triplets), 1.27 (3H, overlapping triplets), 1.38 (1.12H, s), 1.39 (1.88H, s), 1.61 (1.12 H, s), 1.64 (1.88H, s), 3.1–4.3 (7H, overlapping multiplets), 4.48 (0.38H, s), 4.50 (0.62H, s), 4.85 (0.38H, d, J=10 Hz), 4.92 (0.62H, d, J=10 Hz), 5.22 (2H, s), 5.55 (0.62H, d, J=4 Hz), 5.57 (0.38H, d, J=4Hz), 6.36 (1H, m), 7.4 (5H, s); product of Preparation F1 (0.60 g., 0.0016 mol) and 2-(ethylamino)-N-ethylacetamide (0.83 g., 0.0064 mol).

C67. Benzyl 6-beta[S-1-(N-(N-propylcarbamoylmethyl)-N-benzylcarbamoyl)-1-hydroxymethyl]penicillanate; 1:9 ethyl acetate:CHCl$_3$; 0.32 g.; tlc Rf 0.25 (3:7 ethyl acetate:CHCl$_3$); $^1$H-nmr (CDCl$_3$) delta (300 MHz), reflecting two amide rotamers in 1:1 ratio, 0.83 (1.5H, t), 0.86 (1.5H, t), 1.35 (1.5H, s), 1.36 (1.5H, s), 1.40 (2H, m), 1.47 (1.5H, s), 1.56 (1.5H, s), 3.0–3.2 (2H, complex), 3.76 (0.5H, d), 3.90 (0.5H, d), 4.0–4.2 (2H, overlapping multiplets), 4.44 (0.5H, s), 4.46 (0.5H, s), 4.61 (0.5H, d), 4.8–5.0 (1.5H, complex), 5.04 (0.5H, d), 5.19 (2H, s), 5.53 (0.5H, d, J=4 Hz), 5.58 (0.5H, d), 6.26 (0.5H, br.t), 6.40 (0.5H, br.t), 7.2–7.5 (10H, aromatics); product of Preparation F1 (0.60 g., 0.0016 mol) and 2-(benzylamino)-N-propylacetamide (1.3 g., 0.0064 mol).

C68. Benzyl 6-beta-[S-1-[S-(2-(N-ethylcarbamoyl)pyrrolidino)carbonyl]-1-hydroxymethyl]penicillanate; ethyl acetate; 0.225 g.; tlc Rf 0.2 (ethyl acetate); $^1$H-nmr (CDCl$_3$) delta (300 MHz), reflecting two amide rotamers in about 1:5 ratio, 1.08 (3H, t), 1.35 (3H, s), 1.57 (0.5H, s), 1.60 (2.5H, s), 1.7–2.2 (4H, complex), 3.1–3.3 (2H, complex), 3.5–3.8 (3H, complex), 4.01 (1H, dd, J=4 Hz, 10 Hz), 4.42 (0.17H, s), 4.46 (0.83H, s), 4.76 (1H, complex), 5.18 (2H, s), 5.48 (0.83H, d, J=4 Hz), 5.51 (0.17H, d, J=4 Hz), 6.8 (1H, br.s), 7.26 (5H, s), 7.36 (5H, s); product of Preparation F1 (0.60 g., 0.0016 mol) and N(amide)ethyl-L-prolinamide (0.91 g., 0.0064 mol).

C69. Benzyl 6-beta-[S-1-[N-(N-(2-methylpropyl)carbamoylmethyl)-N-(2-methylpropyl)carbamoyl]-1-hydroxymethyl]penicillanate; 3:7 ethyl acetate:CHCl$_3$; 0.12 g.; $^1$H-nmr (CDCl$_3$) delta (300 MHz) reflecting two amide rotamers in about 1:1 ratio, 0.8–1.0 (12H, complex), 1.38 (3H, br.s), 1.61 (3H, br.s), 1.76 (1H, m), 2.04 (1H, m), 2.9–3.2 (3H, complex), 3.47 (0.5H, m), 3.66 (0.5H, m), 3.9–4.2 (2H, complex), 4.3–4.6 (2H, complex), 4.91 (1H, m), 5.22 (2H, br.s), 5.55 (1H, m), 6.63 (1H, m), 7.4 (5H, br.s); product of Preparation F1 (0.60 g., 0.0016 mol) and 2-[(2-methylpropyl)amino]-N-(2-methylpropyl)acetamide (1.1 g., 0.0064 mol). (2-methylpropyl)acetamide (1.1 g., 0.0064 mol).

C70. Benzyl 6-beta-[S-(N-(2-morpholinoethyl)-N-ethylcarbamoyl)-1-hydroxymethyl]penicillanate; 1:99 CH$_3$OH:ethyl acetate; tlc Rf 0.35 (1:19 CH$_3$OH:ethyl acetate); 0.11 g.; $^1$H-nmr (CDCl$_3$) delta (300 MHz), reflecting two amide rotamers in about 1:2 ratio, 0.85 (1H, t), 1.10 (2H, t), 1.33 (3H, s), 1.58 (3H, s), 2.3–3.0 (6H, complex), 3.2–4.0 (8H, complex), 4.0–4.1 (1H, complex), 4.45 (1H, s), 4.78 (1H, d, J=10 Hz), 5.16 (2H, s), 5.47 (0.3H, d, J=4 Hz), 5.51 (0.7H, d, J=4 Hz), 7.35 (5H, s); product of Preparation F1 (0.60 g., 0.0016 mol) and N-[2-(ethylamino)ethyl]morpholine (1.0 g., 0.0064 mol).

C71. Benzyl 6-beta-[S-1-[N-(R-alpha-methylbenzyl)carbamoyl]-1-hydroxymethyl]penicillanate; 1:4 ethyl acetate:CHCl$_3$; 0.35 g.; tlc Rf 0.4 (1:4 ethyl acetate:CHCl$_3$); $^1$H-nmr (CDCl$_3$) delta (300 MHz) 1.35 (3H, s), 1.47 (3H, d, J=7 Hz), 1.62 (3H, s), 3.62 (1H, d, J=3 Hz), 3.77 (1H, dd, J=4 Hz, 10 Hz), 4.44 (1H, s), 4.70 (1H, dd, J=3 Hz, 10 Hz), 5.06 (1H, m), 5.16 (2H, Abq), 5.47 (1H, d, J=4 Hz), 6.98 (1H, d), 7.3–7.4 (10H, aromatics); product of Preparation F1 (0.80 g., 0.0021 mol) and R-(+)-alpha-methylbenzylamine (0.266 ml., 0.0021 mol).

C72. Benzyl 6-beta-[S-1-[N-(S-alpha-methylbenzyl)carbamoyl]-1-hydroxymethyl]penicillanate; 1:4 ethyl acetate:CHCl$_3$; 0.18 g.; $^1$H-nmr (CDCl$_3$) delta (300 MHz), 1.36 (3H, s), 1.48 (3H, d, J=8 Hz), 1.60 (3H, s), 3.86 (1H, dd, J=4 Hz, 8 Hz), 4.42 (1H, s), 4.63 (1H, d, J=8 Hz), 5.06 (1H, m), 5.17 (2H, ABq), 5.50 (1H, d, J=4 Hz), 6.94 (1H, d, J=9 Hz), 7.2–7.4 (10H, aromatics); product of Preparation F1 (0.80 g., 0.0021 mol) and S-(−)-alpha-methylbenzylamine (0.266 ml., 0.0021 mol).

C73. Benzyl 6-beta-[S-1-(N-benzhydrylcarbamoyl)-1-hydroxymethyl]penicillanate; 1:19 ethyl acetate:CHCl$_3$); 0.45 g.; $^1$H-nmr (CDCl$_3$) delta (300 MHz), 1.33 (3H, s), 1.57 (3H, s), 3.77 (1H, dd, J=4 Hz, 8 Hz), 4.35 (1H, s), 4.66 (1H, d, J=8 Hz), 5.07 (2H, ABq), 5.38 (1H, d, J=4 Hz), 6.06 (1H, d, J=9 Hz), 7.0–7.2 (15H, complex), 7.25 (1H, d, J=9 Hz); product of Preparation F1 (0.8 g., 0.0021 mol) and benzhydrylamine (0.71 ml., 0.0041 mol).

C74. Benzyl 6-beta-[S-1-(N-[N-(2-morpholinoethyl)carbamoylmethyl]-N-benzylcarbamoyl)-1-hydroxymethyl]penicillanate; 1:99 CH$_3$OH:ethyl acetate (1 l.) then 1:9 CH$_3$OH:ethyl acetate (1.5 l.); 0.23 g.; tlc Rf 0.5 (1:9 CH$_3$OH:ethyl acetate; $^1$H-nmr (CDCl$_3$) delta (300 MHz), reflecting amide rotamers in about 7:9 ratio, 1.30 (1.3H, s), 1.32 (1.7H, s), 1.42 (1.3H, s), 1.54 (1.7H, s), 2.3–2.5 (6H, complex), 3.0–3.8 (6H, complex), 3.95

(0.44H, dd, J=4 Hz, 10 Hz), 4.10 (0.56 H, dd, J=4 Hz, 10 Hz), 4.2-4.3 (1H, complex), 4.39 (0.44H, s), 4.41 (0.56H, s), 4.51 (0.44H, d, J=16 Hz), 4.72 (0.56H, d, J=10 Hz, 4.83 (0.44H, d, J=10 Hz), 4.92 (0.56H, d, J=14 Hz), 5.13 (2H, br.s), 5.46 (1H, complex), 6.62 (0.56H, m), 6.91 (0.44H, m), 7.1-7.4 (10H, complex); product of Preparation F1 (0.60 g., 0.0016 mol) and 2-benzylamino-N-(2-morpholinoethyl)acetamide (1.8 g., 0.0064 mol).

C75. Benzyl 6-beta-[S-1-(S-2-(N,N-dimethylcarbamoyl)pyrrolidinocarbonyl)-1-hydroxymethyl]-penicillanate; 1:24 $CH_3OH$:ethyl acetate; 0.33 g.; tlc Rf 0.5 (1:9 $CH_3OH$:ethyl acetate); $^1$H-nmr ($CDCl_3$) delta (300 MHz), reflecting amide rotamers in about 1:2 ratio, 1.32 (3H, s), 1.56 (1H, s), 1.59 (2H, s), 1.7-2.2 (4H, complex), 2.88 (2H, s), 2.90 (1H, s), 3.00 (1H, s), 3.03 (2H, s), 3.5-3.9 (3H, complex), 3.9-4.1 (1H, complex), 4.41 (1H, s), 4.7-4.9 (1H, complex), 5.10 (2H, ABq), 5.41 (0.67H, d, J=4 Hz), 5.44 (0.33H, d, J=4 Hz), 7.3 (5H, s); product of Preparation F1 (0.60 g., 0.0016 mol) and the N,N-dimethyl amide of L-proline (0.24 g., 0.0017 mol).

C76. Benzyl 6-beta-[S-1-(1,4-diazabicyclo[3.3.2]non-4-ylcarbonyl)-1-hydroxymethyl]penicillanate; gradient elution with 1 l. each 1:12, 1:9, 1:7, 1:5, 1:1 $CH_3OH$:ethyl acetate and finally $CH_3OH$; 0.11 g.; tlc Rf 0.1 (1:1 $CH_3OH$:ethyl acetate); $^1$H-nmr ($CDCl_3$) delta (300 MHz), reflecting amide rotamers in about 1:3 ratio, 1.36 (3H, s), 1.59 (3H, s), 1.6-1.8 (2H, complex), 1.9-2.1 (2H, complex), 2.8-3.1 (8H, complex), 3.70 (1H, t), 3.97 (0.75H, dd, J=4 Hz, 10 Hz), 4.05 (0.25H, dd, J=4 Hz, 10 Hz), 4.41 (1H, s), 4.48 (1H, br.s), 4.78 (1H, d, J=10 Hz), 5.15 (2H, s), 5.42 (0.25H, d, J=4 Hz), 5.47 (0.75H, d, J=4 Hz), 7.32 (5H, s); product of Preparation F1 (0.60 g., 0.0016 mol) and 1,4-diazabicyclo[3.2.2]nonane (0.20 g., 0.016 mol).

C77 Benzyl 6-beta-[S-1-(S-2-(pyrrolidinocarbonyl)-pyrrolidinocarbonyl)-1-hydroxymethyl]penicillanate; 1:99 $CH_3OH$:ethyl acetate; 0.32 g.; tlc Rf 0.45 (1:9 $CH_3OH$:ethyl acetate; $^1$H-nmr ($CDCl_3$) delta (300 MHz), reflecting amide rotamers in about 3:7 ratio, 1.30 (3H s), 1.54 (0.9H, s), 1.57 (2.1H, s), 1.7-2.2 (8H, complex), 3.2-3.9 (6H, complex), 4.0 (1H, complex), 4.40 (1H, s), 4.42 (0.3H, m), 4.54 (0.7H, m), 4.68 (0.3H, d, J=10 Hz), 4.75 (0.7H, d, J=9 Hz), 5.10 (2H, complex), 5.39 (0.7H, d, J=4 Hz), 5.44 (0.3H, d, J=4 Hz), 7.28 (5H, s); product of Preparation F1 (0.60 g, 0.0016 mol) and the pyrrolidine amide of L-proline (0.26 g., 0.016 mol).

C78. Benzyl 6-beta-[S-1-(N-methyl-N-(4-hydroxyphenyl)carbamoyl)-1-hydroxymethyl]penicillanate; $CHCl_3$; 0.21 g.; tlc Rf 0.4 (1:19 ethyl acetate:$CHCl_3$); $^1$H-nmr ($CDCl_3$) delta (300 MHz) 1.36 (3H, s), 1.62 (3H, s), 2.76 (3H, s), 3.93 (1H, dd, J=4 Hz, 10 Hz), 4.49 (1H, s), 4.90 (1H, d, J=10 Hz), 5.13 (2H, ABq), 5.49 (1H, d, J=4 Hz), 6.51 (2H, d, J=9 Hz), 6.88 (2H, d, J=9 Hz), 7.31 (5H, s); product of Preparation F1 (0.774 g., 0.0020 mol) and N-methyl-p-hydroxyaniline (0.308 g., 0.0022 mol).

METHOD D—OXIDATION REACTIONS

EXAMPLE D1

Benzyl 6-beta-[S-1-(Dimethylcarbamoyl)-1-hydroxymethyl]-penicillanate 1-alpha- and 1-beta-Oxide Title product of Example B1 (2.0 g., 0.0051 mol) was slurried in 20 ml. of ethyl acetate and cooled to 0°. m-Chloroperbenzoic acid (80%, 1.1 g., 0.0051 mol) was added and the reaction stirred for 20 minutes at 0°, complete solution occurring within 1 minute of the peracid addition. The reaction mixture was washed 5×15 ml. cold saturated $NaHSO_3$, 5×15 ml. cold saturated $NaHCO_3$ and 1×15 ml. brine, dried and stripped to a solid foam (2.2 g.). The foam was chromatographed on 90 g. silica gel, collecting 25 ml. fractions. Fractions 48-80 were stripped to yield title 1-beta-oxide as an oil (1.0 g.) which was crystallized from $CHCl_3$ and ether, 0.60 g.; mp 159°-160°; tlc Rf 0.3 (1:1 ethyl acetate:$CHCl_3$); $^1$H-nmr ($CDCl_3$) delta (TMS): 1.06 (3H, s), 1.56 (3H, s), 2.93 (3H, s), 3.13 (3H, s), 3.6 (1H, br.s), 4.05 (1H, dd, J=5 Hz, 9 Hz), 4.59 (1H, s), 5.07 (1H, d, J=5 Hz), 5.20 (2H, Abq), 5.43 (1H, br.d, J=9 Hz), 7.35 (5H, s). Fractions 125-135 were stripped to yield title alpha-oxide, 0.20 g.; tlc Rf 0.15 (1:1 ethyl acetate:$CHCl_3$), $^1$H-nmr ($CDCl_3$) delta (TMS): 1.20 (3H, s), 1.50 (3H, s), 2.96 (6H, br.s), 4.03 (1H, m, J values obscured by residual ethyl acetate in sample), 4.34 (1H, s), 4.68 (1H, d, J=4 Hz), 4.86 (1H, br.m), 5.09 (2H, s), 7.3 (5H, s).

EXAMPLE D2

Benzyl 6-beta-[S-1-(Pyrrolidinocarbonyl)-1-hydroxymethyl]-penicillanate 1-alpha- and 1-beta-Oxide With the initial mixture of products isolated as a solid foam (2.5 g.), and employing ethyl acetate as eluant, the procedure of the preceding Example was employed to convert title product of Example B3 (1.9 g.) into the less polar 1-beta-oxide, 1 g.; tlc Rf 0.4 (ethyl acetate); $^1$H-nmr ($CDCl_3$) delta (TMS): 1.05 (3H, s), 1.56 (3H, s), 1.7-2.0 (4H, overlapping multiplets), 3.3-3.7 (5H, overlapping multiplets), 4.02 (1H, dd, J=5 Hz, 9 Hz), 4.54 (1H, s), 5.03 (1H, d, J=5 Hz), 5.17 (2H, ABq), 5.16 (1H, br.d, J=9 Hz), 7.3 (5H, s); and the more polar 1-alpha-oxide, 100 mg.; $^1$H-nmr ($CDCl_3$) delta (TMS): 1.27 (3H, s), 1.60 (3H, s), 1.7-2.2 (4H, complex overlapping multiplets), 3.3-3.7 (4H, complex overlapping multiplets), 4.17 (1H, dd, J values obscured by ethyl acetate remaining in sample), 4.46 (1H, s), 4.76 (1H, br.m), 4.78 (1H, d, J=5 Hz), 5.20 (2H, s), 7.35 (5H, s).

EXAMPLE D3

Benzyl 6-beta-[S-1-(Dimethylcarbamoyl)-1-hydroxymethyl]-penicillanate 1,1-Dioxide Title product of Example B1 (0.20 g., 0.51 mmol) in 3 ml. ethyl acetate was combined with m-chloroperbenzoic acid (80%, 0.27 g., 0.0013 mol) at 0°-5°, then stirred 22 hours at ambient temperature, recooled to 0°-5°, washed 5×3 ml. cooled, saturated $NaHSO_3$, 5×3 ml. cold, saturated $NaHCO_3$, 1×brine, dried, stripped to an oil (0.10 g.) and chromatographed on 4 g. silica gel with 3:7 ethyl acetate:$CHCl_3$ as eluant to yield title product, 60 mg.; $^1$H-nmr ($CDCl_3$) delta (TMS): 1.26 (3H, s), 1.50 (3H, s), 2.96 (3H, s), 3.17 (3H, s), 3.95 (1H, v.br), 4.25 (1H, dd, J=5 Hz, 10 Hz), 4.48 (1H, s), 4.95 (1H, d, J=5 Hz), 5.26 (2H, ABq), 5.46 (1H, d, J=10), 7.4 (5H, s).

EXAMPLE D4

Benzyl 6-beta-[S-1-(Pyrrolidinocarbonyl)-1-hydroxymethyl]-penicillanate 1,1-Dioxide By the procedure of the preceding Example, title product of Example B3 (0.85 g., 0.002 mol) was converted to instant, chromatographed title product, 90 mg.; $^1$H-nmr (CDCl$_3$) delta (TMS): 1.26 (3H, s), 1.49 (3H, s), 1.7–2.1 (4H, overlapping multiplets), 3.3–3.9 (5H, overlapping multiplets), 4.20 (1H, dd, J=5 Hz, 9 Hz), 4.41 (1H, s), 4.89 (1H, d, J=5 Hz), 4.95–5.40 (4H, overlapping multiplets), 7.3 (5H, s).

EXAMPLE D5

Benzyl 6-beta-[S-1-(4-Hydroxypiperidinocarbonyl)-1-hydroxymethyl]penicillanate 1,1-Dioxide Title product of Example C7 (0.10 g., 0.22 mmol) and m-chloroperbenzoic acid (85%, 0.135 g., 0.67 mmol) in 20 ml. ethyl acetate were stirred under N$_2$ for 20 hours, washed 4×10 ml. saturated NaHSO$_3$, 3×10 ml. saturated NaHCO$_3$, 2×10 ml. H$_2$O and 1×10 ml. brine, dried and stripped on an 80 mg. residue. The latter was chromatographed on 30 g. silica gel with ethyl acetate as eluant, collecting 20 ml. fractions. Fractions 7–12 were combined and stripped to yield title product as a solid foam, 55 mg.; tlc Rf 0.3 (ethyl acetate); $^1$H-nmr (CDCl$_3$) delta: 1.25 (3H, s), 1.48 (3H, s), 1.2–2.1 (4H, complex), 2.33 (1H, complex), 3.0–3.6 (2H, complex), 3.6–4.2 (4H, complex), 4.21 (1H, dd, J=5 Hz, 9 Hz), 4.44 (1H, s), 4.91 (1H, d, J=5 Hz), 5.20 (2H, ABq), 5.40 (1H, broad complex), 7.3 (5H, s).

EXAMPLE D6

Benzyl 6-beta-[S-1-(N-Benzyl-N-methylcarbamoyl)-1-hydroxymethyl]penicillanate 1,1-Dioxide Using 3:7 ethyl acetate:CHCl$_3$ as eluant, the method of the preceding Example was used to convert title product of Example C16 (0.10 g., 0.21 mmol) to instant title product, 33 mg.; $^1$H-nmr (CDCl$_3$) delta: 1.27 (3H, s), 1.50 (3H, s), 2.79 (1H, s), 3.01 (2H, s), 4.20 (1H, dd, J=5 Hz, 10 Hz), 4.42 (1H, s), 4.62 (1H, d, J=5 Hz), 4.88 (1H, d, J=5 Hz), 5.11 (2H, ABq), 5.5 (1H, broad complex), 7.22 (5H, s), 7.33 (5H, s).

EXAMPLE D7

Benzyl 6-beta-[S-1-(N-(2-Phenylethyl)-N-methylcarbamoyl)-1-hydroxymethyl]penicillanate 1,1-Dioxide Using 1:4 ethyl acetate:CHCl$_3$ as eluant, the method of Example D5 was used to convert benzyl 6-beta-[S-1-(N-(2-phenylethyl)-N-methylcarbamoyl)-1-hydroxymethyl]penicillanate (0.10 g, 0.21 mmol) to instant title product, about 30 mg.; $^1$H-nmr (CDCl$_3$) delta (300 MHz): 1.29 (3H, br.s), 1.54 (3H, s), 2.8–3.1 (2H, overlapping multiplets), 2.94 (1.2H, s), 3.08 (1.8H, s), 3.47 (0.6H, multiplet), 3.6–3.8 (1.4H, overlapping multiplets), 4.27 (1H, overlapping multiplets), 4.51 (1H, br.s), 4.98 (1H, overlapping doublets), 5.21 (1.2H, ABq), 5.36 (0.8H, ABq), 5.46 (0.6H, d, J=10 Hz), 5.54 (0.4H, d, J=9 Hz), 7.2–7.5 (10 Hz, aromatics), reflecting amide rotamers in 2:3 ratio.

EXAMPLE D8

Benzyl 6-beta-[S-1-(1,2,3,4-Tetrahydroisoquinolinocarbonyl)-1-hydroxymethyl]penicillanate 1,1-Dioxide Using CHCl$_3$ as eluant, the method of Example D5 was used to convert title product of Example C11 (0.2 g., 0.92 mmol) to instant title product, 0.12 g.; $^1$H-nmr (CDCl$_3$) delta: 1.26 (3H, s), 1.46 (3H, s), 2.8–3.2 (2H, br.t), 3.3–4.4 (4H, complex overlapping multiplets), 4.44 (1H, s), 4.8–5.0 (2H, complex), 5.20 (2H, ABq), 5.60 (1H, br.d), 7.2–7.5 (9H, aromatics).

EXAMPLE D9

Benzyl 6-beta-[S-1-(N-Methyl-N-phenylcarbamoyl)-1-hydroxymethyl]penicillanate 1,1-Dioxide Using 3:7 ethyl acetate:CHCl$_3$ as eluant, the method of Example D5 was used to convert title product of Example C17 (0.14 g., 0.31 mmol) to instant title product, 0.12 g.; $^1$H-nmr (CDCl$_3$) delta: 1.23 (3H, s), 1.46 (3H, s), 3.24 (3H, s), 4.06 (1H, dd, J=5 Hz, 9 Hz), 4.30 (1H, s), 4.80 (1H, d, J=5 Hz), 5.12 (2H, ABq), 7.3 (10H, aromatic).

EXAMPLE D10

Benzyl 6-beta-[S-1-(4-Phenylpiperazinocarbonyl)-1-hydroxymethyl]penicillanate 1,1-Dioxide By the method of Example D7, the title product of Example C19 (0.30 g., 0.61 mmol) was converted to instant title product, 0.11 g.; $^1$H-nmr (CDCl$_3$) delta (300 MHz): 1.26 (3H, s), 1.50 (1.5H, s), 1.52 (1.5H, s), 1.6–2.0 (4H, complex), 2.6–2.9 (3H, complex), 3.1–3.3 (2H, complex), 4.2–4.4 (2H, complex), 4.51 (1H, s), 4.70 (1H, complex), 5.03 (1H, d, J=5 Hz), 5.24 (2H, ABq), 5.53 (0.5H, d), 5.57 (0.5H, d), 7.2–7.5 (10H, complex), reflecting a mixture of the two amide conformations in about 1:1 ratio.

EXAMPLE D11

Benzyl 6-beta-[S-1-(L-2-Benzyloxycarbonylpyrrolidinocarbonyl)-1-hydroxymethyl]penicillanate 1,1-Dioxide By the method of Example D9, title product of Example C22 (0.30 g., 0.54 mmol) was converted to instant title product, 0.16 g.; $^1$H-nmr (CDCl$_3$) delta: 1.23 (3H, s), 1.46 (3H, s), 1.8–2.3 (4H, complex), 3.2–4.4 (5H, complex, 4.4–5.0 (2H, complex), 5.0–5.6 (5H, complex), 7.26 (5H, s), 7.32 (5H, s).

EXAMPLE D12

Benzyl 6-beta-[S-(N-Cyclohexyl-N-methylcarbamoyl)-1-hydroxymethyl]penicillanate 1,1-Dioxide By the method of Example D5, using 1:3 ethyl acetate:CHCl$_3$ as eluant, the title product of Example C23 (0.13 g., 0.28 mmol) was converted to instant title product, 81 mg.; $^1$H-nmr (CDCl$_3$) delta (300 MHz): 1.28 (3H, s), 1.53 (3H, s), 0.9–2.0 (10H, complex), 2.85 (1.3H, s), 3.04 (1.7H, s), 3.8–4.1 (1H, complex), 4.2–4.4 (2H, complex), 4.48 (0.45H, s), 4.49 (0.55H, s), 4.94 (0.55H, d, J=5 Hz), 4.97 (0.45H, d, J=5 Hz), 5.28 (2H, ABq), 5.44 (1H, complex), 7.4 (5H, s), reflecting the two amide rotamers in a ratio of 4:5.

EXAMPLE D13

Benzyl 6-beta-[S-1-(N-Benzyl-N-ethylcarbamoyl)-1-hydroxymethyl]penicillanate 1,1-Dioxide By the method of Example D5, using 1:9 ethyl acetate:CHCl$_3$ as eluant, title product of Example C25 (0.30 g., 0.62 mmol) was converted to instant chromatographed title product, 0.14 g.; $^1$H-nmr (CDCl$_3$) delta (300 MHz) reflecting the 2 amide conformers in 3:4 ratio: 1.02 (1.3H, t), 1.16 (1.7H, t), 1.24 (3H, s), 1.49 (3H, s), 3.1–3.7 (3H, multiplets), 4.24 (1H, complex), 4.4–4.5 (1.6H, complex), 4.6–4.7 (1.2H, complex), 4.92 (0.57H, d, J=5 Hz), 4.94 (0.43H, d, J=5 Hz), 5.23 (2H, ABq), 5.52 (1H, complex), 7.2–7.4 (10H, aromatics).

EXAMPLE D14

Benzyl 6-beta-[S-1-(N-Methyl-N-(4-methoxyphenyl)carbamoyl)-1-hydroxymethyl]penicillanate 1,1-Dioxide By the method of Example D5, without chromatography, title product of Example C33 (0.1 g., 0.206 mmol) was converted to instant title product, 0.105 g.; $^1$H-nmr (CDCl$_3$) delta: 1.18 (3H, s), 1.40 (3H, s), 3.16 (3H, s), 3.73 (3H, s), 4.06 (1H, dd, J=4 Hz, 10 Hz), 4.28 (1H, s), 4.77 (1H, d, J=10 Hz), 5.12 (1H, d, J=4 Hz), 6.97 (4H, ABq), 7.25 (5H, s).

EXAMPLE D15

Benzyl 6-beta-[S-1-[N-(R-alpha-methylbenzyl)carbamoyl]-1-hydroxymethyl]penicillanate 1,1-Dioxide The product of Example C71 (0.12 g.) was converted to the present product according to the method of the preceding Examples using 1:4 ethyl acetate:CHCl$_3$ as eluant on chromatography, 0.11 g.; $^1$H-nmr (CDCl$_3$) delta (300 MHz), 1.21 (3H, s), 1.45 (3H, d, J=8 Hz), 1.50 (3H, s), 3.79 (1H, dd, J=5 Hz, 10 Hz), 4.48 (1H, s), 4.75 (1H, d, J=5 Hz), 5.1–5.3 (3H, complex), 7.11 (1H, d, J=9 Hz), 7.2–7.4 (10 H, complex).

METHOD E—HYDROGENOLYSIS REACTIONS

EXAMPLE E1

Sodium 6-beta-(S-1-Carbamoyl-1-hydroxymethyl)penicillanate

P 10% Pd/C (0.12 g.) was prehydrogenated in 2.5 ml. H$_2$O at 4 atmospheres for 5 minutes. Title product of Example C1 (95 mg., 0.27 mmol) in 2.5 ml. THF and NaHCO$_3$ (21 mg., 0.25 mmols) were added and the mixture hydrogenated 20 minutes at 4 atmospheres. Catalyst was recovered by filtration and the filtrate stripped of THF, adjusted from pH 3.9 to 5.5 with dilute sodium bicarbonate, and freeze dried to yield title product, 60 mg.; $^1$H-nmr (D$_2$O) delta (300 MHz): 1.40 (3H, s), 1.58 (3H, s), 3.87 (1H, dd, J=4 Hz, 10 Hz), 4.20 (1H, s), 4.65 (1H, d, J=10 Hz), 5.44 (1H, d, J=4 Hz).

EXAMPLE E2

Sodium 6-beta-[S-1-(Benzylcarbamoyl)-1-hydroxymethyl]-penicillanate

10% Pd/C (60 mg.) was prehydrogenated in 5 ml. H$_2$O. Title product of Example C2 (60 mg., 0.13 mmol) in 5 ml. THF was added and the mixture hydrogenated at 4 atmospheres for 1 hour. The catalyst was recovered by filtration, the filtrate was stripped of THF, and the aqueous residue was extracted with ethyl acetate. The ethyl acetate was stripped to yield the free acid form of title product, 50 mg. The latter was redissolved in ethyl acetate, layered with 10 ml. H$_2$O and the pH adjusted to 6.0 with dilute NaHCO$_3$. The aqueous layer was freeze dried to yield title product, 7 mg.; $^1$H-nmr (D$_2$O) delta (300 MHz): 1.34 (3H, s), 1.50 (3H, s), 3.79 (1H, dd, J=4 Hz, 10H), 4.12 (1H, s), 4.31 (2H, s), 4.61 (1H, d, J=10 Hz), 5.32 (1H, d, J=4 Hz), 7.23 (5H, m).

EXAMPLE E3

Sodium 6-beta-[S-1-(tert-Butylcarbamoyl)-1-hydroxymethyl]-penicillanate

By the procedure of Example E1, title product of Example C3 (0.20 g., 0.48 mmol) was converted to instant title product, 90 mg.; $^1$H-nmr (D$_2$O) delta (300 MHz): 1.25 (9H, s), 1.41 (3H, s), 1.56 (3H, s), 3.79 (1H, dd, J=4 Hz, 10 Hz), 4.16 (1H, s), 4.48 (1H, d, J=10 Hz), 5.36 (1H, d, J=4 HZ).

EXAMPLE E4

Sodium 6-beta-[S-1-(phenylcarbamoyl)-1-hydroxymethyl]-penicillanate

By the method of Example E2, title product of Example C4 (100 mg.) was hydrogenated. Catalyst was recovered by filtration, THF was stripped from the filtrate, and the aqueous residue extracted 2×10 ml. ethyl acetate, adjusted from pH 4.9 to 6.0 with dilute NaHCO$_3$ and freeze dried to yield title product, 37 mg.; $^1$H-nmr (D$_2$O) delta (300 MHz): 1.39 (3H, s), 1.54 (3H, s), 3.90 (1H, dd, J=4 Hz, 9 Hz), 4.16 (1H, s), 4.68 (1H, d, J=9 Hz), 5.38 (1H, d, J=4 Hz), 7.36 (5H, m).

EXAMPLE E5

6-beta-[S-1-(Dimethylcarbamoyl)-1-hydroxymethyl]-penicillanic Acid and Its Sodium Salt By the method of Example E1, title product of Example B1 (3.9 g., 0.10 mol) was converted to freeze dried title product as the sodium salt, 2.8 g.; $^1$H-nmr (D$_2$O) delta (300 MHz): 1.41 (3H, s), 1.56 (3H, s), 2.91 (3H, s), 3.15 (3H, s), 3.91 (1H, dd, J=4 Hz, 10 Hz), 4.18 (1H, s), 4.89 (1H, d, J=10 Hz), 5.34 (1H, d, J=4 Hz).

The sodium salt (0.5 g.) was dissolved in 3 ml. H$_2$O and layered with 3 ml. of ethyl acetate. The pH was adjusted from 5.6 to 2.0 with dilute HCl. The aqueous layer was extracted 2×3 ml. ethyl acetate. The three organic layers were combined, dried, stripped, and the residue crystallized with ether to yield title product (free acid), 0.37 g.; $^1$H-nmr (CDCl$_3$/DMSO-d$_6$) delta (300 MHz): 1.51 (3H, s), 1.64 (3H, s), 2.94 (3H, s), 3.14 (3H, s), 4.01 (1H, dd, J=4 Hz, 9 Hz), 4.36 (1H, s), 4.83 (1H, d, J=9 Hz), 5.46 (1H, d, J=4 Hz.

EXAMPLE E6

Sodium 6-beta-[S-1-(Diethylcarbamoyl)-1-hydroxymethyl]-penicillanate

Washing 1×3 ml. ethyl acetate before freeze drying, the procedure of Example E1 was employed to convert the title product of Example C5 (0.34 g., 0.81 mmol) to instant title product, 97 mg; $^1$H-nmr (D$_2$O) delta: 1.10 (3H, t), 1.23 (3H, t), 1.47 (3H, s), 1.60 (3H, s), 3.40 (4H, 2 overlapping q), 3.93 (1H, dd, J=4 Hz, 10 Hz), 4.18 (1H, s), 4.86 (1H, d, J=10 Hz), 5.37 (1H, d, J=4 Hz).

EXAMPLE E7

Sodium 6-beta-[S-1-(Isopropylcarbamoyl)-1-hydroxymethyl]-penicillanate

By the procedure of the preceding Example, S-title product of Example B2 (25 mg., 0.06 mmol) was converted to instant title product, 15 mg.; $^1$H-nmr(D$_2$O) delta (300 MHz): 1.04 (6H, d, J=8 Hz), 1.37 (3H, s), 1.52

(3H, s), 3.77 (1H, dd, J=4 Hz, 10 Hz), 3.83 (1H, m, J=8 Hz), 4.12 (1H, s), 4.50 (1H, d, J=10 Hz), 5.32 (1H, d, J=4 Hz).

EXAMPLE E8

Sodium 6-beta-[S-1-(Pyrrolidinocarbonyl)-1-hydroxymethyl]-penicillanate

By the method of Example E6, S-title product of Example B3 (2.09 g., 5 mmol) was converted to instant title product, 1.3 g.; $^1$H-nmr (D$_2$O) delta (300 MHz): 1.37 (3H, s), 1.54 (3H, s), 1.84 (4H, overlapping multiplets), 3.33 (2H, t), 3.60 (2H, t), 3.91 (1H, dd, J=4 Hz, 10 Hz), 4.15 (1H, s), 4.71 (1H, d, J=10 Hz), 5.31 (1H, d, J=4 Hz).

EXAMPLE E9

Sodium 6-beta-[S-1-(Piperidinocarbonyl)-1-hydroxymethyl]-penicillanate

By the method of Example E6, title product of Example B4 (1.6 g., 3.6 mmol) was converted to instant title product. The resulting freeze dried product (0.70 g.) was slurried in a small amount of ethanol to produce crystalline title product, 0.25 g.; $^1$H-nmr (D$_2$O) delta (300 MHz): 1.40 (3H, s), 1.55 (3H, s), 1.58 (6H, complex overlapping multiplets), 3.35–3.65 (4H, overlapping multiplets), 3.87 (1H, dd, J=4 Hz, 10 Hz), 4.15 (1H, s), 4.90 (1H, d, J=10 Hz), 5.33 (1H, d, J=4 Hz).

EXAMPLE E10

Sodium 6-beta-[S-1-(Perhydroazepinocarbonyl)-1-hydroxymethyl]penicillanate

By the method of Example E6, title product of Example C6 (0.33 g., 0.74 mmol) was converted to instant title product, 0.19 g.; $^1$H-nmr (D$_2$O) delta (300 MHz): 1.38 (3H, s), 1.52 (3H, s), 1.54 (8H, complex overlapping multiplets), 3.0–3.8 (4H, complex overlapping multiplets), 3.92 (1H, dd, J=4 Hz, 10 Hz), 4.15 (1H, s), 4.85 (1H, d, J=10 Hz), 5.34 (1H, d, J=4 Hz).

EXAMPLE E11

Sodium 6-beta-[S-1-(4-Hydroxypiperidinocarbonyl)-1-hydroxymethyl]penicillanate

By the method of Example E6, title product of Example C7 (0.13 g., 0.29 mmol) was converted to present product, 70 mg.; $^1$H-nmr (D$_2$O) delta (250 MHz): 1.48 (3/2H, s), 1.49 (3/2H, s), 1.62 (3/2H, s), 1.64 (3/2H, s), 1.6–2.2 (4H, overlapping multiplets), 3.0–3.5 (4H, overlapping multiplets), 3.8–4.3 (4H, overlapping multiplets), 4.27 (1/2H, s), 4.28 (1/2H, s), 4.99 (1/2H, d, J=9 Hz), 5.00 (1/2H, d, J=9 Hz), 5.43 (1H, overlapping doublets), reflecting a 1:1 mixture of the amide conformers.

EXAMPLE E12

Sodium 6-beta-[S-1(Morpholinocarbonyl)-1-hydroxymethyl]-penicillanate

By the method of Example E6, S-title product of Example B5 (0.5 g., 1.2 mmol) was hydrogenated to instant freeze dried title product, 0.13 g.; $^1$H-nmr (D$_2$O) delta (90 MHz): 1.47 (3H, s), 1.60 (3H, s), 3.6–4.1 (9H, overlapping multiplets), 4.33 (1H, s), 5.03 (1H, d, J=10 Hz), 5.50 (1H, d, J=4 Hz).

EXAMPLE E13

Sodium 6-beta-[S-1-(4-Formylpiperazinocarbonyl)-1-hydroxymethyl]penicillanate

By the procedure of Example E6, title product of Example C8 (0.26 g., 0.56 mmol) was converted to the above name product, 123 mg.; $^1$H-nmr (D$_2$O) delta (300 MHz): 1.52 (3H, s), 1.66 L (3H, s), 3.4–4.0 (8H, complex overlapping multiplets), 4.05 (1H, dd, J=4 Hz, 10 Hz), 4.30 (1H, s), 5.05 (1H, d, J=10 Hz), 5.50 (1H, d, J=4 Hz), 8.14 (1H, s).

EXAMPLE E14

Sodium 6-beta-[S-1-(Methylcarbamoyl)-1-hydroxymethyl]-penicillanate

Except that the initial pH was adjusted from 8.0 to 5.2 with 1N HCl, the procedure of Example E1 was employed to convert title product of Example C9 (0.37 g., 0.98 mmols) to present freeze dried title product, 95 mg.; $^1$H-nmr (D$_2$O) delta (90 MHz): 1.46 (3H, s), 1.63 (3H, s), 2.76 (3H, s), 3.88 (1H, dd, J=4 Hz, 9 Hz), 4.23 (1H, s), 4.65 (1H, d, J=9 Hz), 5.45 (1H, d, J=4 Hz).

EXAMPLE E15

Sodium 6-beta-[S-B 1-(2-Hydroxyethylcarbamoyl)-1-hydroxymethyl]-penicillanate

By the procedure of Example E6, title product of Example C10 (0.325 g., 0.8 mmole) was converted to instant title product, 78 mg.; $^1$H-nmr (D$_2$O) delta (300 MHz): 1.40 (3H, s), 1.55 (3H, s), 3.29 (2H, t, J=6 Hz), 3.59 (2H, t, J=6 Hz), 3.83 (1H, dd, J=4 Hz, 10 Hz), 4.16 (1H, s), 4.61 (1H, d, J=10 Hz), 5.37 (1H, d, J=4 Hz).

EXAMPLE E16

6-beta-[S-1-(1,2,3,4-tetrahydroisoquinolinocarbonyl-1-hydroxymethy]penicillanate By the method of Example E6 (no pH adjustment was necessary), title product of Example C11 (0.25 g., 0.52 mmole) was converted to instant title product. A portion of the title product (53 mg.) precipitated from the aqueous residue on stripping THF, and was recovered by filtration and combined with the remaining product (30 mg.) obtained by freeze drying the ethyl acetate washed aqueous filtrate; $^1$H-nmr (DMSO-d$_6$) delta (300 MHz): 1.34 (1.2H, s), 1.36 (1.8H, s), 1.44 (1.2H, s), 1.48 (1.8H), 2.7–2.9 (2H, overlapping multiplets), 3.5–4.0 (5H, complex multiplet), 4.60 (1H, s), 4.7 (1H, overlapping multiplets), 5.26 (1H, d, J=4 Hz), 7.19 (4H, s), reflecting a 2:3 mixture of amide conformers.

EXAMPLE E17

Sodium 6-beta-[S-1-(N-Methyl-N-[2-hydroxyethyl]carbamoyl)-1-hydroxymethyl]penicillanate Except that the initial pH was adjusted from 3.8 to 5.1 with 1N NaOH, the procedure of Example E1 was employed to convert title product of Example C12 (0.20 g.) to present title product, 0.070 g.; ir (KBr) cm$^{-1}$ 1782, 1761; $^1$H-nmr (D$_2$O) delta (300 MHz) 1.55 (3H, s), 1.69 L (1.5H, s), 1.71 (1.5H, s), 3.06 (1.5H, s), 3.33 (1.5H,

EXAMPLE E18

Sodium 6-beta-[S-1-(2-acetamidoethylcarbamoyl)-1-hydroxymethyl]penicillanate

By the method of Example E6, title product of Example C13 (204 mg., 0.45 mmol) was converted to instant title product, 70 mg.; $^1$H-nmr ($D_2O$) delta (300 MHz): 1.40 (3H, s) 1.56 (3H, s), 1.90 (3H, s), 3.26 (4H, complex overlapping multiplets), 3.79 (1H, dd, J=4 Hz, 10 Hz), 4.06 (1H, s), 4.58 (1H, d, J=10 Hz), 5.37 (1H, d, J=4 Hz).

s), 3.45-4.15 (5H, complex overlapping multiplets), 4.34 (1H, br.s), 5.06 (1H, overlapping doublets), 5.51 (1H, overlapping doublets), reflecting an approximately 1:1 mixture of amide rotamers.

EXAMPLE E19

Sodium 6-beta-[R-1-(Isopropylcarbamoyl)-1-hydroxymethyl]penicillanate

By the method of Example E6, R-title product of Example B2 (80 mg., 0.20 mmol) was converted to instant title product, 20 mg.; $^1$H-nmr ($D_2O$) delta (300 MHz): 1.04 (6H, 2 doublets), 1.42 (3H, s), 1.57 (3H, s), 3.89 (1H, multiplet), 3.94 (1H, dd, J=4 Hz, 9 Hz), 4.10 (1H, s), 4.47 (1H, d, J=9), 5.35 (1H, d, J=4 Hz).

EXAMPLE E20

Sodium 6-beta-[R-1-(Morpholinocarbonyl)-1-hydroxymethyl]penicillanate

By the method of Example E6, R-title product of Example B5 (0.12 g., 0.28 mmol) was converted to instant title product, 80 mg.; $^1$H-nmr ($D_2O$) delta (300 MHz): 1.40 (3H, s), 1.53 (3H, s), 3.4-3.8 (overlapping multiplets), 4.01 (1H, dd, J=4 Hz, 11 Hz), 4.08 (1H, s), 4.94 (1H, d, J=11 Hz), 5.39 (1H, d, J=4 Hz).

EXAMPLE E21

Sodium 6-beta-[S-1-(Pyrrolidinocarbonyl)-1-hydroxymethyl]penicillanate 1-beta-Oxide By the method of Example E6, the 1-beta-oxide of Example D2 (1.0 g., 2.3 mmol) was converted to instant title product, 0.60 g.; $^1$H-nmr ($D_2O$) delta (300 MHz): 1.18 (3H, s), 1.54 (3H, s), 1.84 (4H, m), 3.3-3.7 (4H, overlapping multiplets), 4.03 (1H, dd, J=5 Hz, 9 Hz), 4.23 (1H, s), 5.06 (1H, d, J=9 Hz), 5.19 (1H, s, J=5 Hz).

EXAMPLE E22

Sodium 6-beta-[S-1-(Pyrrolidinocarbonyl)-1-hydroxymethyl]penicillanate 1-alpha-Oxide By the method of Example E6, the 1-alpha-oxide of Example D2 (100 mg., 0.23 mmol) was converted to instant title product, 65 mg.; $^1$H-nmr ($D_2O$) delta (300 MHz): 1.20 (3H, s), 1.54 (3H, s), 1.84 (4H, complex multiplet), 3.34 (2H, t), 3.56 (2H, m), 4.15 (1H, dd, J=5 Hz, 8 Hz), 4.16 (1H, s), 4.69 (1H, d, J=5 Hz), 4.91 (1H, d, J=8 Hz).

EXAMPLE E23

Sodium 6-beta-[S-1-(Dimethylcarbamoyl)-1-hydroxymethyl]penicillanate 1-beta-Oxide 10% Pd/C (600 mg.) was prehydrogenated in 10 ml. of $H_2O$ for 5 minutes. The 1-beta-oxide product of Example D1 (0.60 g.) in 10 ml. THF was added and the mixture hydrogenated at 4 atmospheres for 20 minutes. Catalyst was recovered by filtration, the filtrate was stripped of THF, and the aqueous residue was adjusted from pH 2.2 to 4.5 with 0.1N NaOH, washed 2×10 ml. ethyl acetate, and freeze dried to yield title product, 0.33 g.; $^1$H-nmr ($D_2O$) delta (90 MHz): 1.38 (3H, s), 1.74 (3H, s), 3.00 (3H, s), 3.17 (3H, s), 4.17 (1H, dd, J=5 Hz, 9 Hz), 4.37 (1H, s), 5.32 (1H, d, J=5 Hz), 5.35 (1H, d, J=9 Hz).

EXAMPLE E24

Sodium 6-beta-[S-1-(Pyrrolidinocarbonyl)-1-hydroxymethyl]penicillanate 1,1-Dioxide By the method of the preceding Example, title product of Example D4 (90 mg., 0.2 mmol) was converted to instat title product, 35 mg.; $^1$H-nmr ($D_2O$) delta (300 MHz): 1.34 (3H, s), 1.46 (3H, s), 1.87 (4H, complex multiplet), 3.37 (2H, t), 3.59 (2H, m), 4.15 (1H, dd, J=5 Hz, 10 Hz), 4.22 (1H, s), 5.07 (1H, d, J=5 Hz), 5.17 (1H, d, J=10 Hz).

EXAMPLE E25

Sodium 6-beta-[S-1-1(Dimethylcarbamoyl)-1-hydroxymethyl]penicillanate 1,1-Dioxide By the method of Example 23, title product of Example D3 (60 mg.) was converted to instant title product, 50 mg.; $^1$H-nmr ($D_2O$) delta: 1.41 (3H, s), 1.52 (3H, s), 2.93 (3H, s), 3.14 (3H, s), 4.14 (1H, dd, J=5 Hz, 10 Hz), 4.21 (1H, s), 5.04 (1H, d, J=5 Hz), 5.38 (1H, d, J=10 Hz).

EXAMPLE E26

Sodium 6-beta-[S-1-Di(2-hydroxyethyl)carbamoyl-1-hydroxymethyl]penicillanate

By the method of Example E6, title product of Example C14 (90 mg.) was converted to instant title product, 23 mg.; ir (KBr) 1752 cm$^{-1}$; $^1$H-nmr ($D_2O$) delta (300 MHz): 1.51 (3H, s), 1.65 (3H, s), 3.5-4.0 (8H, overlapping multiplet), 4.05 (1H, dd, J=4 Hz, 10 Hz), 4.30 (1H, s), 5.04 (1H, d, J=10 Hz), 5.58 (1H, d, J=4 Hz).

EXAMPLE E27

Sodium 6-beta-[S-1-(Dipropylcarbamoyl)-1-hydroxymethyl]penicillanate

By the method of Example E6, title product of Example C15 (110 mg.) was converted to instant title product, 40 mg.; ir (KBr) 1756 cm$^{-1}$; $^1$H-nmr ($D_2O$) delta (300 Mz): 0.93 (6H, two overlapping triplets), 1.52 (3H, s), 1.5-1.8 (4H, overlapping multiplets), 1.66 (3H, s), 3.2-3.6 (4H, overlapping multiplets), 4.04 (1H, dd, J=4 Hz, 10 Hz), 4.30 (1H, s), 4.94 (1H, d, J=10 Hz), 5.46 (1H, d, J=4 Hz).

EXAMPLE E28

Sodium 6-beta-[S-1-(N-Benzyl-N-methylcarbamoyl)-1-hydroxymethyl]penicillanate

By the method of Example E6, title product of Example C16 (0.13 g.) was converted to instant title product, 50 mg.; $^1$H-nmr (D$_2$O) delta (300 MHz): 1.46 (1.2H, s), 1.48 (1.2H, s), 1.52 (1.8H, s), 1.66 (1.8H, s), 2.96 (1.2H, s), 3.17 (1.8H, s), 4.08 (1H, overlapping multiplets), 4.24 (0.4H, s), 4.30 (0.6H, s), 4.4–5.1 (3H, overlapping multiplets), 5.49 (1H, d, J=4 Hz), 7.3–7.5 (5H, aromatics).

EXAMPLE E29

Sodium 6-beta-[S-1-(N-Methyl-N-phenylcarbamoyl)-1-hydroxymethylpenicillanate

By the method of Example E6, title product of Example C17 (0.163 g.) was converted to instant title product, 0.10 g.; $^1$H-nmr (D$_2$O) delta (300 MHz): 1.40 (3H, s), 1.50 (3H, s), 3.34 (3H, s), 4.06 (1H, overlapping doublets), 4.18 (1H, s), 4.52 (1H, d, J=10 Hz), 5.43 (1H, d, J=4 Hz), 7.4–7.7 (5H, aromatic).

EXAMPLE E30

Sodium 6-beta-[S-1-(N-Benzyl-N-(2-hydroxyethylcarbamoyl-1-hydroxymethyl]penicillanate By the method of Example E6, title product of Example C18 (0.19 g.) was converted to instant title product, 0.11 g.; $^1$H-nmr (D$_2$O) delta (300 MHz): 1.42 (1.4H, s), 1.48 (1.4H, s), 1.52 (1.6H, s), 1.66 (1.6H, s), 3.2–3.9 (4H, overlapping multiplets), 4.06 (1H, overlapping multiplets), 4.23 (0.46H, s), 4.32 (0.54H, s), 4.6–5.2 (3H, overlapping multiplets), 5.51 (1H, d, J=4 Hz), 7.2–7.6 (5H, aromatics), reflecting a mixture of amide rotamers in about 17:20 ratio.

EXAMPLE E31

Sodium 6-beta-[S-1-(4-Phenylpiperazinocarbonyl)-1-hydroxymethyl]penicillanate

By the method of Example E6, title product of Example C19 (0.16 g.) was converted to instant title product, 27 mg.; ir (KBr) 1781, 1763 cm$^{-1}$; $^1$H-nmr (D$_2$O) delta (300 MHz): 1.51 (2H, s), 1.52 (1H, s), 1.57 (2H, s), 1.62 (1H, s), 1.4–2.0 (4H, overlapping multiplets), 2.7–3.0 (2H, overlapping multiplets), 3.1–3.5 (1H, overlapping multiplets), 4.05 (1H, dd, J=4 Hz, 10 Hz), 4.30 (1H, s), 3.9–4.6 (2H, overlapping multiplets), 5.04 (1/3H, d, J=10 Hz), 5.05 (2/3H, d, J=10 Hz), 5.49 (1/3H, d, J=4 Hz), 5.52 (2/3H, d, J=4 Hz), 7.2–7.6 (5H, aromatic, reflecting amide rotamers in about 2:1 ratio.

EXAMPLE E32

Sodium 6-beta-[S-1-(Dibenzylcarbamoyl)-1-hydroxymethyl]penicillanate

By the method of Example E6, title product of Example C20 (262 mg.) was converted to instant title product, 28 mg.; ir (KBr) 1753 cm$^{-1}$; $^1$H-nmr (D$_2$O) delta (300 MHz): 1.42 (3H, s), 1.46 (3H, s), 4.14 (1H, dd, J=4 Hz, 9 Hz), 4.22 (1H, s), 4.2–5.0 (5H, overlapping multiplets), 5.52 (1H, d, J=4 Hz), 6.9–7.5 (10H, aromatic).

EXAMPLE E33

Sodium 6-beta-[S-1-(L-2-(Hydroxymethyl)pyrrolidinocarbonyl)-1-hydroxymethyl]penicillanate By the method of Example E6, title product of Example C21 (253 mg.) was converted to instant title product, 65 mg.; $^1$H-nmr (D$_2$O) delta (300 MHz): 1.54 (3H, s), 1.69 (2H, s), 1.71 (1H, s), 1.9–2.2 (4H, overlapping multiplets), 3.5–3.9 (4H, overlapping multiplets), 4.06 (0.67H, dd, J=4 Hz, 10 Hz), 4.12 (0.33 H, dd, J=4 Hz, 9 Hz), 4.19 (0.67H, multiplet), 4.31 (1H, s), 4.43 (0.33H, multiplet), 4.88 (0.67H, d, J=10 Hz), 4.93 (0.33H, d, J=9 Hz), 5.41 (0.33H, d, J=4 Hz), 5.46 (0.67H, d, J=4 Hz), reflecting a mixture of two amide rotamers in a 1:2 ratio.

EXAMPLE E34

Disodium 6-beta-[S-1-(L-Prolinocarbonyl)-1-hydroxymethyl]penicillanate

By the method of Example E6, but with double the level of catalyst and NaHCO$_3$, title product of Example C22 (200 mg.) was converted to instant title product, 85 mg.; ir (KBr) 1767 cm$^{-1}$; $^1$H-nmr (D$_2$O) delta (300 MHz): 1.50 (3H, s), 1.65 (1.5H, s), 1.66 (1.5H, s), 1.8–2.5 (4H, overlapping multiplets), 3.6–4.2 (3H, overlapping multiplets), 4.270 (0.5H, s), 4.274 (0.5H, s), 4.6–5.1 (2H, overlapping multiplets), 5.40 (0.5H, d, J=4 Hz), 5.44 (0.5H, d, J=4 Hz), reflecting amide rotamers in 1:1 ratio.

EXAMPLE E35

Sodium 6-beta-[S-1-(N-Cyclohexyl-N-methylcarbamoyl)-1-hydroxymethyl]penicillanate By the method of Example E6, title product of Example C23 (100 mg.) was converted to instant title product, 40 mg.; $^1$H-nmr (D$_2$O) delta (300 MHz): 1.50 (3H, s), 1.65 (3H, s), 1.0–2.0 (10H, overlapping multiplets), 2.87 (1.5H, s), 3.10 (1.5H, s), 4.26 (1H, s), 3.8–4.3 (2H, overlapping multiplets), 4.95 (0.5H, d, J=10 Hz), 5.02 (0.5H, d, J=10 Hz), 5.4–5.5 (1H, overlapping multiplets), reflecting the two amide rotamers in about 1:1 ratio.

EXAMPLE E36

Sodium 6-beta-[S-1-(N-Benzyl-N-phenylcarbamoyl)-1-hydroxymethyl]penicillanate

By the method of Example E6, except to wash the recovered catalyst cake with extra THF, title product of Example C24 (160 mg.) was converted to instant freeze dried title product, all of which was taken up in ethyl acetate to leave 16 mg. of a mixture of insoluble products. The ethyl acetate solution (about 5 ml.) wash stripped and the residue taken up in 0.5 ml. CHCl$_3$ and 15 ml. H$_2$O. The pH was adjusted from 5.0 to 3.0 with dilute HCl. The aqueous layer was freeze dried to yield title product, 37 mg.; $^1$H-nmr (D$_2$O) delta (300 MHz): 1.41 (3H, s), 1.50 (3H, s), 4.09 (1H, dd, J=4 Hz, 10 Hz), 4.18 (1H, s), 4.55 (1H, d, J=10 Hz), 4.86 (1H, d, J32 15 Hz), 5.11 (1H, d, J=15 Hz), 5.48 (1H, d, J=4 Hz), 7.4–7.4 (10H, aromatic), a single amide rotamer predominating.

EXAMPLE E37

Sodium 6-beta-[S-1-(N-Benzyl-N-ethylcarbamoyl)-1-hydroxymethyl]penicillanate

By the method of Example E6, title product of Example C25 (200 mg.) was converted to instant title product, 45 mg.; $^1$H-nmr (D$_2$O) delta (300 MHz) 1.10 (1.2H, t), 1.27 (1.8H, t), 1.45 (1.2H, s), 1.47 (1.2H, s), 1.52 (1.8H, s), 1.66 (1.8H, s), 3.2–3.7 (2H, overlapping multiplets), 4.0–4.1 (1H, overlapping multiplets), 4.21 (0.4H, s), 4.29 (0.6H, s), 4.4–5.1 (3H overlapping multiplets), 5.46 (1H, d, J=4 Hz), 7.2–7.6 (5H, aromatic), reflecting amide rotamers (conformations) in a ratio of about 2:3.

EXAMPLE E38

Sodium 6-beta-[S-1-(4-Hydroxypiperidinocarbonyl)-1-hydroxymethyl]penicillanate 1,1-Dioxide Without adjusting the pH (which was 3.7) before freeze drying, the method of Example E6 was used to convert title product of Example D5 (55 mg., 0.11 mmol) was converted to instant title product, 25 mg.; $^1$H-nmr (D$_2$O) delta (300 MHz): 1.43 (3H, s), 1.3–1.7 (2H, complex multiplet), 1.56 (3H, s), 1.9–2.1 (2H, complex multiplet), 2.9–3.5 (2H, overlapping multiplets), 3.7–4.3 (4H, overlapping multiplets), 4.34 (1H, s), 5.16 (1H, d, J=5 Hz), 5.42 (1H, overlapping doublets), indicating the presence of the two amide rotamers in about 1:1 ratio.

EXAMPLE E39

Sodium 6-beta-[S-1-(N-Benzyl-N-methylcarbamoyl)-1-hydroxymethyl]penicillanate 1,1-Dioxide By the method of the preceding Example (the pH was 5.0), title product of Example D6 (33 mg., 0.066 mmol) was converted to instant title product, 15 mg.; $^1$H-nmr (D$_2$O) delta (300 MHz): 1.45 (3H, s), 1.57 (3H, s), 2.87 (0.9H, s), 3.12 (2.1H, s), 4.2–4.5 (3H, complex multiplet), 4.6–5.0 (1H, multiplet partially obscured by HOD peak), 5.20 (1H, overlapping doublets), 5.48 (1H, overlapping doublets), 7.2–7.6 (5H, aromatics), reflecting the presence of the two amide rotamers in about 3:7 ratio.

EXAMPLE E40

Sodium 6-beta-[S-1-(N-(2-Phenylethyl)-N-methylcarbamoyl)-1-hydroxymethyl]penicillanate 1,1-Dioxide By the method of Example E6, title product of Example D7 (40 mg., 0.077 mmol) was converted to instant title product, 18 mg.; $^1$H-nmr (D$_2$O) delta (300 MHz): 1.47 (3H, s), 1.59 (3H, s), 2.94 (1H, s), 3.06 (2H, s), 2.7–3.2 (2H, overlapping multiplets), 3.5–4.0 (2H, overlapping multiplets), 4.25 (1H, multiplet), 4.34 (1H, s), 5.18 (1H, d, J=5 Hz), 5.36 (⅔H, d, J=10 Hz), 5.41 (⅓H, d, J=10 Hz), 7.2–7.7 (5H, aromatic), reflecting the amide rotamers in about 2:1 ratio.

EXAMPLE E41

Sodium 6-beta-[S-1-(1,2,3,4-Tetrahydroisoquinolinocarbonyl)-1-hydroxymethyl]penicillanate 1,1-Dioxide By the method of Example E6, title product of Example D8 (0.12 g., 0.23 mmol) was converted to instant title product, 33 mg.; ir (KBr) 1778 cm$^{-1}$; $^1$H-nmr (D$_2$O) delta (300 MHz): 1.45 (3H, s), 1.54 (3H, s), 3.09 (2H, t), 4.06 (2H, t), 4.33 (1H, s), 4.36 (1H, dd, J=5 Hz, 10 Hz), 5.27 (1H, d, J=5 Hz), 5.98 (1H, d, J=10 Hz), 7.42 (1H, d), 7.50 (1H, t), 7.68 (1H, t), 8.13 (1H, d), representing the dominant amide rotamer composing about 90% of the rotamer mixture.

EXAMPLE E42

Sodium 6-beta-[S-1-(N-Methyl-N-phenylcarbamoyl)-1-hydroxymethyl]penicillanate 1,1-Dioxide By the method of Example E6, title product of Example D9 (0.14 g., 0.29 mmol) was converted to instant title product, 50 mg.; $^1$H-nmr (D$_2$O) delta (300 MHz): 1.46 (3H, s), 1.57 (3H, s), 3.33 (3H, s), 4.22 (1H, s), 4.28 (1H, dd, J=5 Hz, 10 Hz), 5.05 (1H, d, J=10 Hz), 5.18 (1H, d, J=5 Hz), 7.3–7.7 (5H, aromatics), a single amide rotamer predominating.

EXAMPLE E43

Sodium 6-beta-[S-1-(4-Phenylpiperazinocarbonyl)-1-hydroxymethyl]penicillanate 1,1-Dioxide By the method of Example E6, title product of Example D10 (0.11 g., 0.23 mmol) was converted to instant title product, 30 mg.; $^1$H-nmr (D$_2$O) delta (300 MHz): 1.46 (1.8H, s), 1.48 (1.2H, s), 1.54 (1.8H, s), 1.60 (1.2H, s), 1.7–1.9 (4H, complex), 2.6–3.3 (4H, complex), 4.0–4.3 (2H, complex), 4.33 (0.6H, s), 4.35 (0.4H, s), 4.4–4.5 (1H, complex), 5.19 (1H, d, J=5 Hz), 5.46 (0.4H, d, J=10 Hz), 5.52 (0.6H, d, J=10 Hz), 7.1–7.4 (5H, aromatic complex), reflecting the two amide conformers in about 2:3 ratio.

EXAMPLE E44

Disodium 6-beta-[S-1-(L-Prolinocarbonyl)-1-hydroxymethyl]penicillanate 1,1-Dioxide By the method of Example E6, title product of Example D11 (0.16 g., 0.27 mmol) was converted to instant title product, 40 mg.; $^1$H-nmr (D$_2$O) delta (300 MHz): 1.42 (3H, s), 1.56 (3H, s), 1.9–2.3 (4H, complex), 3.5–4.3 (4H, complex), 4.31 (1H, s), 4.63 (1H, d), 5.13 (1H, d, J=4 Hz), 5.18 (1H, d, J=10 Hz), a single amide rotamer predominating.

EXAMPLE E45

Sodium 6-beta-[S-1-(N-Cyclohexyl-N-methylcarbamoyl)-1-hydroxymethyl]penicillanate 1,1-Dioxide By the method of Example E6, title product of Example D12 (81 mg., 0.16 mmol) was converted to instant title product, 15 mg.; $^1$H-nmr (D$_2$O) delta (300 MHz): 1.42 (3H, s), 1.56 (3H, s), 1.0–1.9 (10H, complex), 2.84 (1.5H, s), 3.03 (1.5H, s), 3.7–4.2 (2H, complex), 4.22 (1H, dd, J=5 Hz, J=10 Hz), 4.28 (1H, s), 5.16 (1H, overlapping doublets), 5.33 (0.5H, d, J=10 Hz), 5.42 (0.5H, d, J=10 Hz), reflecting the two amide rotamers in about 1:1 ratio.

EXAMPLE E46

Sodium 6-beta-[S-1-(Isoindolinocarbonyl)-1-hydroxymethyl]-penicillanate

By the method of Example E16, but removing a white solid from the aqueous residue after THF strip and washing the filtrate of the aqueous residue with 5 ml. ethyl acetate prior to freeze drying, title product of Example C27 (0.25 g., 0.54 mmol) was converted to instant title product, 0.125 g.; ir (KBr) 1758, 1732 cm$^{-1}$; $^1$H-nmr (D$_2$O) delta (300 MHz): 1.48 (3H, s), 1.66 (3H, s), 4.09 (1H, dd, J=4 Hz, 10 Hz), 4.31 (1H, s), 4.72 (2H, s), 4.91 (1H, d, J=10 Hz), 5.05 (2H, ABq), 5.47 (1H, d, J=4 Hz), 7.39 (4H, s).

EXAMPLE E47

Sodium 6-beta-[S-1-(4-Phenylpiperazinocarbonyl)-1-hydroxymethyl]penicillanate By the method of Example E16, title product of Example C26 (0.4 g., 0.79 mmol) was converted to instant title product, 80 mg.; $^1$H-nmr (D$_2$O) delta (300 MHz): 1.53 (3H, s), 1.68 (3H, s), 3.1–4.3 (9H, overlapping complexes), 4.32 (1H, s), 5.10 (1H, d, J=10 Hz), 5.52 (1H, d, J=4 Hz), 7.1–7.6 (5H, aromatic).

EXAMPLE E48

Sodium 6-beta-[S-1-(N-(2-Hydroxyethyl)-N-phenylcarbamoyl)-1-hydroxymethyl]penicillanate By the method of Example E16, title product of Example C28 (0.13 g., 0.27 mmol) was converted to instant title product, 57 mg.; $^1$H-nmr (D$_2$O) delta (300 MHz) (predominantly 1 amide conformer): 1.49 (3H, s), 1.64 (3H, s), 3.49 (2H, complex), 3.93 (1H, dd, J=4 Hz, 10 Hz), 4.24 (1H, s), 4.39 (2H, complex), 4.76 (1H, d, J=10 Hz), 5.42 (1H, d, J=4 Hz), 6.8–7.4 (5H, aromatics).

EXAMPLE E49

Sodium 6-beta-[S-1-(N-(Ethoxycarbonylmethyl)-N-benzylcarbamoyl)-1-hydroxymethyl]penicillanate By the method of Example E16, title product of Example C29 (0.371 g., 0.68 mmol) was converted to instant title product 110 mg.; $^1$H-nmr (D$_2$O) delta (300 MHz) (reflecting the 2 amide conformers in about 3:2 ratio): 1.27 (1.8H, t), 1.29 (1.2H, t), 1.54 (1.8H, s), 1.56 (1.2H, s), 1.58 (1.8H, s), 1.68 (1.2H, s), 4.0–4.5 (6H, complex) 4.7–5.1 (3H, complex), 5.52 (0.6H, d, J=4 Hz), 5.56 (0.4H, d, J=4 Hz), 7.3–7.6 (5H, aromatics).

EXAMPLE E50

Sodium 6-beta-[S-1-(N-(Dimethylcarbamoylmethyl)-N-benzylcarbamoyl-1-hydroxymethyl]penicillanate By the method of Example E6, title product of Example C30 (0.232 g., 0.43 mmol) was converted to instant title product, 57 mg.; ir (KBr) 1757 cm$^{-1}$; $^1$H-nmr (D$_2$O) delta (300 MHz) (reflecting the 2 amide conformers in about 2:1 ratio): 1.45 (2H, s), 1.46 (2H, s), 1.50 (1H, s), 1.62 (1H, s), 2.90 (3H, s), 2.92 (3H, s), 4.0–5.1 (7H, complex), 5.44 (0.67H, d, J=4 Hz), 5.47 (0.33H, d, J=4 Hz), 7.3–7.5 (5H, aromatics).

EXAMPLE E51

Sodium 6-beta-[S-1-(N-(Methylcarbamoylmethyl)-N-benzylcarbamoyl)-1-hydroxymethyl]penicillanate By the method of Example E6, title product of Example C32 (0.34 g., 0.65 mmol) was converted to instant title product, 178 mg.; ir (KBr) 1755 cm$^{-1}$; $^1$H-nmr (D$_2$O) delta (300 MHz) (reflecting the two amide conformers in about 1:1 ratio): 1.52 (4.5H, br.s), 1.66 (1.5H, s), 2.73 (1.5H, s), 2.77 (1.5H, s), 3.9–5.1 (7H, complex), 5.51 (0.5H, d, J=4 Hz), 5.54 (0.5H, d, J=4 Hz), 7.3–7.6 (5H, aromatics).

EXAMPLE E52

Sodium 6-beta-[S-1-(N-Methyl-N-(4-methoxyphenyl)carbamoyl)-1-hydroxymethyl]penicillanate By the method of Example E6, title product of Example C33 (0.53 g., 1.1 mmol) was converted to instant title product, 0.3 g.; $^1$H-nmr (D$_2$O) delta (300 MHz) (reflecting predominantly a single amide conformer): 1.41 (3H, s), 1.52 (3H, s), 3.28 (3H, s), 3.90 (3H, s), 4.07 (1H, dd, J=4 Hz, 10 Hz), 4.20 (1H, s), 4.51 (1H, d, J=10 Hz), 5.42 (1H, d, J=4 Hz), 7.29 (4H, ABq).

EXAMPLE E53

Sodium 6-beta-[S-1-(N-Methyl-N-(4-methylphenyl)carbamoyl)-1-hydroxymethyl]penicillanate By the method of Example E6, title product of Example C31 (0.55 g., 1.18 mmols) was converted to instant title product, 0.35 g.; $^1$H-nmr (D$_2$O) delta (300 MHz): 1.38 (3H, s), 1.49 (3H, s), 2.38 (3H, s), 3.28 (3H, s), 4.04 (1H, dd, J=4 Hz, 10 Hz), 4.16 (1H, s), 4.50 (1H, d, J=10 Hz), 5.40 (1H, d, J=4 Hz), 7.38 (4H, s).

EXAMPLE E54

Sodium 6-beta-[S-1-(4-(2-Pyridyl)piperazinocarbonyl)-1-hydroxymethyl]penicillanate By the method of Example E16, title product of Example C34 (0.42 g., 0.82 mmol) was converted to instant title product, 0.2 g.; $^1$H-nmr (D$_2$O) delta (300 MHz): 1.48 (3H, s), 1.64 (3H, s), 3.4–3.9 (8H, complex), 4.04 (1H, dd, J=4 Hz, 10 Hz), 4.18 (1H, s), 5.03 (1H, d, J=10 Hz), 5.47 (1H, d, J=4 Hz), 6.90 (1H, t), 6.97 (1H, d), 7.75 (1H, t), 8.13 (1H, d).

EXAMPLE E55

Sodium 6-beta-[S-1-(Indolinocarbonyl)-1-hydroxymethyl]-penicillanate

By the method of Example E6, but using a double load of catalyst, title product of Example C35 (100 mg., 0.21 mmol) was converted to instant title product, 45 mg.; $^1$H-nmr (D$_2$O) delta (300 MHz) predominantly a single amide conformer): 1.50 (3H, s), 1.68 (3H, s), 3.28 (2H, t), 4.15 (1H, dd, J=4 Hz, 9 Hz), 4.33 (1H, s), 4.38 (2H, complex), 5.00 (1H, d, J=9 Hz), 5.52 (1H, d, J=4 Hz), 7.2–7.5 (3H, complex), 8.04 (1H, d, J=8 Hz).

EXAMPLE E56

Sodium
6-beta-[S-1-(N-(Pyrrolidinocarbonylmethyl)-N-benzyl-carbamoyl)-1-hydroxymethyl]penicillanate By the method of Example E6, title product of Example C36 (0.317 g., 0.56 mmol) was converted to instant title product, 0.15 g.; $^1$H-nmr (D$_2$O) delta (300 MHz) (reflecting the 2 amide conformers in 1:3 ratio): 1.51 (3.6H, s), 1.54 (1.2H, s), 1.66 (1.2H, s), 1.8–2.0 (4H, complex), 3.3–3.5 (4H, complex), 3.9–4.2 (2H, complex), 4.26 (0.6H, s), 4.30 (0.4H, s), 4.4–5.1 (5H, complex), 5.49 (0.6H, d, J=4 Hz), 5.53 (0.4H, d J=4 Hz), 7.3–7.6 (5H, complex).

EXAMPLE E57

Sodium
6-beta-[S-1-(N-Benzyl-N-isopropylcarbamoyl)-1-hydroxymethyl]penicillanate By the method of Example E16, title product of Example C37 (0.31 g., 0.63 mmol) was converted to instant title product, 0.15 g.; $^1$H-nmr (D$_2$O) delta (300 MHz) (reflecting two amide conformers in 3:7 ratio): 1.07 (1.8H, overlapping d), 1.27 (4.2H, overlapping d), 1.40 (0.9H, s), 1.49 (0.9H, s), 1.54 (2.1H, s), 1.70 (2.1H, s), 4.05 (1H, complex), 4.19 (0.3H, s), 4.32 (0.7H, s), 4.5–4.8 (4H, complex), 5.47 (1H, overlapping d), 7.3–7.5 (5H, complex).

EXAMPLE E58

Sodium
6-beta-[S-1-(N-(2-(2-Pyridyl)ethyl)-N-methylcarbamoyl)-1-hydroxymethyl]penicillanate By the method of Example E16, title product of Example C38 (0.7 g., 1.45 mmols) was converted to instant title product, 0.41 g.; $^1$H-nmr (D$_2$O) delta (300 MHz) (reflecting the 2 amide conformers in 1:3 ratio): 1.47 (0.75H, s), 1.49 (2.25H, s), 1.62 (3H, s), 2.97 (0.75H, s), 3.22 (2.25H, s), 3.31 (2H, complex), 3.6–4.2 (3.25H, complex), 4.24 (0.75H, s), 4.72 (0.25H, d, J=10 Hz), 4.88 (0.75H, d), 5.26 (0.75H, d, J=4 Hz), 5.38 (0.25H, d, J=4 Hz), 7.6–8.7 (4H, heteroaromatics).

EXAMPLE E59

Sodium
6-beta-[S-1-(N-Ethoxycarbonylmethyl-N-methylcarbamoyl)-1-hydroxymethyl]penicillanate By the method of Example E6, title product of Example C39 (0.59, 1.3 mmol) was converted to instant title product, 0.3 g.; $^1$H-nmr (D$_2$O) delta (300 MHz) (reflecting amide conformers in 1:2 ratio): 1.36 (3H, complex), 1.56 (3H, s), 1.68 (1H, s), 1.72 (2H, s), 3.08 (1H, s), 3.36 (2H, s), 4.0–4.5 (6H, complex), 4.9–5.1 (1H, doublets), 5.50 (1H, complex).

EXAMPLE E60

Sodium
6-beta-[S-1-(N-Pyrrolidinocarbonylmethyl)-N-methylcarbamoyl)-1-hydroxymethyl]penicillanate By the method of Example E6, title product of Example C40 (0.39 g., 0.8 mmol) was converted to instant title product, 0.17 g.; $^1$H-nmr (D$_2$O) delta (300 MHz) (reflecting amide conformers in 1:2 ratio): 1.54 (3H, s), 1.65 (1H, s), 1.70 (2H, s), 2.00 (4H, complex), 3.03 (1H, s), 3.30 (2H, s), 3.50 (4H, complex), 4.07 (1H, complex), 4.1–4.4 (3H, complex), 5.09 (1H, d, J=10 Hz), 5.48 (1H, complex).

EXAMPLE E61

Sodium
6-beta-[S-1-(N,N-bis-(Ethoxycarbonylmethyl)carbamoyl)-1-hydroxymethyl]penicillanate By the method of Example E6, title product of Example C41 (0.30 g., 0.56 mmol) was converted to instant title product, 60 mg.; $^1$H-nmr (D$_2$O) delta (300 MHz): 1.34 (6H, complex), 1.55 (3H, s), 1.70 (3H, s), 4.0–4.6 (10H, complex), 5.01 (1H, d, J=10 Hz), 5.54 (1H, d, J=4 Hz).

EXAMPLE E62

Sodium
6-beta-[S-1-(N-Dimethylcarbamoylmethyl)-N-methylcarbamoyl)-1-hydroxymethyl]penicillanate By the method of Example E6, title product of Example C42 (0.50 g., 1.1 mmol) was converted to instant title product, 176 mg.; $^1$H-nmr (D$_2$O) delta (300 MHz) (reflecting the 2 amide conformers in 3:7 ratio): 1.54 (3H, br.s), 1.66 (0.9H, s), 1.70 (2.1H, s), 3.00 (3H, s), 3.02 (0.9H, s), 3.10 (3H, s), 3.28 (2.1H, s), 4.07 (1H, dd, J=4 Hz, 10 Hz), 5.47 (0.7H, d, J=4 Hz), 5.50 (0.3H, d, J=4 Hz).

EXAMPLE E63

Sodium
6-beta-[S-1-(N-(Methylcarbamoylmethyl)-N-methylcarbamoyl)-1-hydroxymethyl]penicillanate By the method of Example E6, title product of Example C43 (0.50 g., 1.1 mmol) was converted to instant title product 0.32 g.; $^1$H-nmr (D$_2$O) delta (300 MHz), reflecting the two amide conformers in 1:2 ratio: 1.53 (3H, s), 1.64 (1H, s), 1.69 (2H, s), 2.80 (2H, s), 2.84 (1H, s), 3.04 (1H, s), 3.30 (2H, s), 4.0–4.1 (3H, complex), 4.31 (0.33H, s), 4.32 (0.67H, s), 5.07 (0.67H, d, J=10 Hz), 5.48 (0.67H, d, J=4 Hz), 5.51 (0.33H, d, J=4 Hz).

EXAMPLE E64

Sodium
6-beta-[S-1-(N-(Carbamoylmethyl)-N-methylcarbamoyl)-1-hydroxymethyl]penicillanate By the method of Example E6, title product of Example C44 (0.32 g., 0.73 mmol) was converted to instant title product, 0.18 g.; $^1$H-nmr (D$_2$O) delta (300 MHz), reflecting the 2 amide conformers in 3:7 ratio: 1.54 (3H, br.s), 1.66 (0.9H, s), 1.70 (2.1H, s), 3.06 (0.9H, s), 3.32 (2.1H, s), 4.07 (1H, complex), 4.17 (1.4H, s), 4.32 (0.3H, s), 4.34 (0.7H, s), 4.42 (0.6H, ABq), 5.09 (0.7H, d, J=10 Hz), 5.49 (0.7H, d, J=4 Hz), 5.53 (0.3H, d, J=4 Hz).

EXAMPLE E65

Sodium
6-beta-[R-1-(N-Methyl-N-phenylcarbamoyl)-1-hydroxymethyl]penicillanate

By the method of Example E6, title product of Example C45 (0.43 g., 0.95 mmol) was converted to instant title product, 0.31 g.; $^1$H-nmr (D$_2$O) delta (300 MHz): 1.16 (3H, s), 1.43 (3H, s), 3.38 (3H, s), 4.07 (1H, dd, J=4 Hz, 10 Hz), 4.10 (1H, s), 4.79 (1H, d, J=10 Hz), 5.48 (1H, d, J=4 Hz), 7.3–7.7 (5H, complex).

EXAMPLE E66

Sodium 6-beta-[S-1-(N-Benzyl-N-ethylcarbamoyl)-1-hydroxymethyl]penicillanate 1,1-Dioxide By the method of Example E6, title product of Example D13 (0.14 g., 0.27 mmol) was converted to instant title product, 70 mg.; $^1$H-nmr (D$_2$O) delta (300 MHz), reflecting the 2 amide conformers in 4:7 ratio: 1.04 (1.1H, t), 1.20 (1.9H, t), 1.44 (3H, s), 1.56 (1.1H, s), 1.57 (1.9H, s), 3.2–3.6 (2H, overlapping multiplets), 4.2–4.9 (4H, complexes), 5.17 (0.64H, d, J=5 Hz), 5.20 (0.36H, d, J=5 Hz), 5.42 (0.36H, d, J=10 Hz), 5.47 (0.64H, d, J=10 Hz), 7.2–7.6 (5H, multiplet).

EXAMPLE E67

Sodium 6-beta-[S-1-(N-Methyl-N-(4-methoxyphenyl)carbamoyl)-1-hydroxymethyl]penicillanate 1,1-Dioxide By the method of Example E16, title product of Example D14 (0.1 g., 0.19 mmol) was converted to instant title product, 55 mg.; $^1$H-nmr (D$_2$O) delta (300 MHz), reflecting predominantly a single amide conformer: 1.46 (3H, s), 1.57 (3H, s), 3.29 (3H, s), 3.89 (3H, s), 4.22 (1H, s), 4.27 (1H, dd, J=5 Hz, 10 Hz), 5.01 (1H, d, J=10 Hz), 5.15 (1H, d, J=5 Hz), 7.24 (4H, ABq).

Using the method of E1–E67 above, the following additional compounds were prepared. Shown in sequence is the Example No., the compound, the amount prepared (as a white, lyophilized powder, unless otherwise specified), and the starting material and amount thereof.

E68. Sodium 6-beta-[S-1-(S-2-(methoxycarbonyl)pyrrolidinocarbonyl)-1-hydroxymethyl]penicillanate; 0.33 g.; ir (KBr) 1774, 1747 cm$^-$; $^1$H-nmr (D$_2$O) delta (300 MHz), 1.57 (3H, s), 1.73 (3H, s), 1.9–2.5 (4H, complex), 3.67 (1H, complex), 3.84 (3H, s), 3.94 (2H, complex), 4.07 (1H, dd, J=4 Hz, 10 Hz), 4.96 (1H, d, J=10 Hz), 5.48 (1H, d, J=4 Hz); product of Example C46 (0.52 g.).

E69. Sodium 6-beta-[S-1-(N-carbamoylmethyl-N-benzylcarbamoyl)-1-hydroxymethyl]penicillanate; 0.17 g; ir (KBr) 1756, 1747 cm$^{-1}$; $^1$H-nmr (D$_2$O) delta (300 MHz), reflecting two amide conformers in 3:4 ratio, 1.52 (3.4H, s), 1.56 (1.3H, s), 1.68 (1.3H, s), 3.9–4.4 (4H, complex), 4.5–5.2 (3H, complex), 5.52 (0.57H, d, J=4 Hz), 5.55 (0.43H, d, J=4 Hz), 7.3–7.6 (5H, complex); product of Example C47 (0.31 g.)

E70. Sodium 6-beta-[S-1-(N,N-di(N-methylcarbamoylmethyl)carbamoyl)-1-hydroxymethyl]penicillanate; 78 mg.; ir (KBr) 1750 cm$^{-1}$; $^1$H-nmr (D$_2$O) delta (300 MHz), 1.55 (3H, s), 1.65 (3H, s), 2.82 (3H, s), 2.86 (3H, s), 4.0–4.4 (5H, complex), 4.63 (1H, d, J=17 Hz), 4.83 (1H, d, J=11 Hz), 5.50 (1H, d, J=4 Hz); product of Example C48 (0.15 g).

E71. Sodium 6-beta-[S-1-(N-ethyl-N-phenylcarbamoyl)-1-hydroxymethyl]penicillanate; 0.16 g.; $^1$H-nmr (D$_2$O) delta (300 MHz), 1.17 (3H, t), 1.43 (3H, s), 1.52 (3H, s), 3.77 (2H, m), 4.05 (1H, dd, J=4 Hz, 10 Hz), 4.18 (1H, s), 4.46 (1H, d, J=10 Hz), 5.43 (1H, d, J=4 Hz), 7.5–7.6 (5H, complex); product of Example C49 (0.39 g.).

E72. Sodium 6-beta-[S-1-(1,2,3,4-tetrahydroquinolinocarbonyl)-1-hydroxymethyl]penicillanate; 0.105 g.; $^1$H-nmr (D$_2$O) delta (300 MHz), 1.11 (3H, s), 1.36 (3H, s), 1.49 (1H, m), 1.65 (1H, m), 1.86 (1H, m), 2.11 (1H, m), 2.94 (2H, m), 3.42 (1H, m), 3.7–4.3 (3H, m), 4.97 (1H, m), 5.34 (1H, m), 7.3–7.5 (4H, aromatics); product of Example C50 (0.265 g.).

E73. Sodium 6-beta-[S-1-[N-ethyl-N-(4-hydroxyphenyl)carbamoyl]-1-hydroxymethyl]penicillanate; (twice hydrogenated due to incomplete removal of the phenolic benzyl group in the initial hydrogenation); 54 mg.; $^1$H-nmr (D$_2$O) delta (300 MHz), 1.08 (3H, t), 1.37 (3H, s), 1.44 (3H, s), 3.65 (2H, q), 3.96 (1H, dd, J=4 Hz, 10 Hz), 4.12 (1H, s), 4.39 (1H, d, J=10 Hz), 5.36 (1H, d, J=4 Hz), 6.9–7.4 (4H, aromatics); product of Example C51 (0.40 g.).

E74. Sodium 6-beta-[S-1-(N-ethyl-N-(3-hydroxyphenyl)carbamoyl)-1-hydroxymethyl]penicillanate; (twice hydrogenated since sodium 6-beta-[S-1-(N-ethyl-N-(3-benzyloxyphenyl)carbamoyl)-1-hydroxymethyl]-penicillanate was found in the initial hydrogenation); 70 mg.; $^1$H-nmr (D$_2$O) delta (300 MHz), 1.08 (3H, t), 1.34 (3H, s), 1.42 (3H, s), 3.67 (2H, q), 3.97 (1H, dd, J=4 Hz, 10 Hz), 4.12 (1H, s), 4.40 (1H, d, J=10 Hz), 5.34 (1H, d, J=4 Hz), 6.9–7.5 (4H, aromatics); product of Example C52 (0.20 g.).

E75. Sodium 6-beta-[S-1-(1-(methoxycarbonyl)isoindolinocarbonyl)-1-hydroxymethyl]penicillanate; 0.120 g.; ir (KBr) 1746 cm$^{-1}$; $^1$H-nmr (D$_2$O) delta (300 MHz), reflecting 1-isoindoline diastereoisomers in 1:2 ratio, 1.46 (2H, s), 1.50 (1H, s), 1.64 (2H, s), 1.68 (1H, s), 3.78 (1H, s), 3.81 (2H, s), 4.0–4.2 (1H, complex), 4.29 (0.67H, s), 4.32 (0.33H, s), 4.8–5.3 (4H, overlapping multiplets), 5.4–5.5 (1H, complex), 5.66 (0.33H, s), 5.70 (0.67H, s), 7.4–7.5 (4H, complex); product of Example C53 (0.40 g.).

E76. Sodium 6-beta-[S-1-(N-(N-isopropylcarbamoylmethyl)-N-benzyl)carbamoyl-1-hydroxymethyl]penicillanate; 0.14 g.; ir (KBr) 1749, 1756 cm$^{-1}$; $^1$H-nmr (D$_2$O) delta (300 MHz), reflecting two amide conformers in a ratio of about 5:7, 1.0–1.1 (6H, complex), 1.44 (1.75H, s), 1.46 (1.25H, s), 1.49 (1.75H, s), 1.59 (1.25H, s), 3.7–4.3 (4H, overlapping multiplets), 4.21 (1H, s), 4.5–5.1 (4H, complex), 5.4–5.5 (1H, overlapping doublets), 7.27 (1H, d), 7.3–7.5 (5H, m); product of Example C54 (0.34 g.).

E77. Sodium 6-beta-[S-1-(S-2-(carbamoyl)pyrrolidinocarbonyl)-1-hydroxymethyl]penicillanate; 40 mg.; ir (KBr) 1769 cm$^{-1}$; $^1$H-nmr (D$_2$O) delta (300 MHz), 1.50 (3H, s), 1.63 (3H, s), 1.8–2.3 (4H, complex), 3.4–3.6 (2H, complex), 4.10 (1H, dd, J=4 Hz, 10 Hz), 4.31 (1H, s), 4.61 (1H, t), 5.63 (1H, d, J=10 Hz), 5.67 (1H, d, J=4 Hz); product of Example C55 (0.26 g.).

E78. Sodium 6-beta-[S-1-(S-2-(N-methylcarbamoyl)pyrrolidinocarbonyl)-1-hydroxymethyl]penicillanate; 0.15 g.; ir (KBr) 1753 cm$^{-1}$; $^1$H-nmr (D$_2$O) delta (300 MHz), 1.55 (3H, s), 1.71 (3H, s), 1.9–2.4 (4H, complex), 3.8–4.0 (2H, complex), 4.04 (1H, dd, J=4 Hz, 10 Hz), 4.32 (1H, s), 4.40 (1H, m), 4.94 (1H, d, J=10 Hz), 5.47 (1H, d, J=4 Hz); product of Example C56 (0.26 g.).

E79. Sodium 6-beta-[S-1-(N,N-di(pyrrolidinocarbonylmethyl)carbamoyl)-1-hydroxymethyl]penicillanate; 0.29 g.; $^1$H-nmr (D$_2$O) delta (300 MHz), 1.49 (3H, s), 1.61 (3H, s), 1.8–2.1 (8H, complex), 3.3–3.6 (8H, complex), 4.03 (1H, dd, J=4 Hz, 10 Hz), 4.22 (2H, ABq), 4.26 (1H, s), 4.52 (2H, ABq), 4.86 (1H, d, J=10 Hz), 5.46 (1H, d, J=4 Hz); product of Example C57 (0.40 g.).

E80. Sodium 6-beta-[S-1-[N-(4-(2-hydroxyethyl)piperazinocarbonylmethyl)-N-benzylcarbamoyl]-1-hydroxymethyl]penicillanate; 14 mg; $^1$H-nmr (D$_2$O) delta (300 MHz), reflecting two amide conformers in 1:1 ratio, 1.40 (1.5H, s), 1.42 (1.5H, s), 1.54 (1.5H, s), 1.56 (1.5H, s), 2.6–2.9 (4H, complex), 3.1–3.4 (2H, complex), 3.5–4.1 (8H, complex), 4.1–4.5 (4H, complex), 4.93 (1H, br.d), 5.39 (0.5H, d, J=4 Hz), 5.42 (0.5H, d, J=4 Hz), 7.43 (5H, br.s); product of Example C58 (19 mg.).

E81. Sodium 6-beta-[S-1-(4-(N-isopropylcarbamoylmethyl)piperazinocarbonyl)-1-hydroxymethyl]penicillanate; 0.22 g.; ir (KBr) 1758 cm$^{-1}$; $^1$H-nmr (D$_2$O) delta (300 MHz), 1.11 (6H, d), 1.44 (3H, s), 1.58 (3H, s), 3.0–3.2 (4H, complex), 3.62 (2H, br.s), 3.7–4.0 (6H, complex), 4.22 (1H, s), 4.95 (1H, d, J=10 Hz), 5.43 (1H, d, J=4 Hz); product of Example C59 (0.387 g.). E82. Sodium 6-beta-[S-1-(2,6-dimethylmorpholinocarbonyl)-1-hydroxymethyl]penicillanate; 0.116 g.; ir (KBr) 1762 cm$^{-1}$; $^1$H-nmr (D$_2$O) delta (300 MHz), reflecting two isomers in 1:1 ratio, possible the two amide conformers of a single meso-2,6-dimethylmorpholino isomer, 1.19 (6H, d), 1.46 (3H, s), 1.60 (3H, s), 2.54 (1H, m), 2.98 (1H, m), 3.6–4.3 (6H, overlapping multiplets), 4.91 (0.5H, d, J=10 Hz), 5.01 (0.5H, d, J=10 Hz), 5.41 (0.5H, d, J=4 Hz), 5.43 (0.5H, d, J=4 Hz); product of Example C60 (0.26 g.).

E83. Sodium 6-beta-[S-1-(N-(N-ethylcarbamoylmethyl)-N-benzylcarbamoyl)-1-hydroxymethyl]penicillanate; 0.100 g.; ir (KBr) 1753 cm$^{-1}$; $^1$H-nmr (D$_2$O) delta (300 MHz), reflecting two amide rotamers in 2:3 ratio, 1.01 (3H, complex), 1.44 (1.8H, s), 1.46 (3H, s), 1.58 (1.2H, s), 3.0–3.2 (2H, complex), 4.21 (1H, s), 3.8–5.0 (6H, complex), 5.44 (0.6H, d, J=4 Hz), 5.47 (0.4H, d, J=4 Hz), 7.3–7.5 (5H, m); product of Example C61 (0.20 g.).

E84. Sodium 6-beta-[S-1-(N-(1-methyl-4-piperidyl)-N-methylcarbamoyl)-1-hydroxymethyl]penicillanate; 60 mg.; ir (KBr) 1757 cm$^{-1}$; $^1$H-nmr (D$_2$O) delta (300 MHz), reflecting two amide rotamers in 1:2 ratio, 1.44 (3H, s), 1.58 (3H, s), 1.8–2.2 (4H, complex), 2.82 (1H, s), 2.86 (3H, s), 3.06 (2H, s), 3.0–3.3 (2H, complex), 3.5–3.7 (2H, complex), 3.96 (1H, dd, J=4 Hz, 10 Hz), 4.22 (1H, s), 4.46 (1H, complex), 4.88 (0.7H, d, J=10 Hz), 4.96 (0.3H, d, J=10 Hz), 5.39 (0.7H, d, J=4 Hz), 5.41 (0.3H, d, J=4 Hz); product of Example C62 (162 mg.).

E85. Sodium 6-beta-[S-1-(N-(2-morpholinoethyl)-N-benzylcarbamoyl)-1-hydroxymethyl]penicillanate; 89 mg.; ir (KBr) 1748 cm$^{-1}$; $^1$H-nmr (D$_2$O) delta (300 MHz), reflecting two amide rotamers in 2:3 ratio, 1.42 (3.6H, s), 1.46 (1.2H, s), 1.62 (1.2H, s), 2.5–2.9 (6H, complex), 3.6–3.8 (6H, complex), 4.00 (1H, complex), 4.18 (0.6H, s), 4.25 (0.4H, s), 4.4–5.0 (3H, complex), 5.45 (1H, d, J=4 Hz), 7.4 (5H, complex); product of Example C63 (166 mg.).

E86. Sodium 6-beta-[S-1-(4-(2-hydroxyethyl)-pipierazinocarbonyl)-1-hydroxymethyl]penicillanate; 66 mg.; $^1$H-nmr (D$_2$O) delta (300 MHz), 1.43 (3H, s), 1.58 (3H, s), 2.8–3.1 (6H, complex), 3.6–3.9 (6H, complex), 3.95 (1H, dd, J=4 Hz, 10 Hz), 4.21 (1H, s), 4.96 (1H, d, J=10 Hz), 5.41 (1H, d, J=4 Hz); product of Example C64 (0.14 g.).

E87. Sodium 6-beta-[S-1-(4-benzylpiperazinocarbonyl)-1-hydroxymethyl]penicillanate; 165 mg; ir (KBr) 1751 cm$^{-1}$; $^1$H-nmr (D$_2$O) delta (300 MHz), 1.42 (3H, s), 1.55 (3H, s), 2.8–3.1 (4H, complex), 3.2–3.4 (1H, complex), 3.5–3.9 (3H, complex), 3.94 (1H, dd, J=4 Hz, 10 Hz), 4.05 (2H, s), 4.20 (1H, s), 4.91 (1H, d, J=10 Hz), 5.39 (1H, d, J=4 Hz), 7.46 (5H, br.s); product of Example C65 (346 mg.).

E88. Sodium 6-beta-[S-1-(N-(N-ethylcarbamoylmethyl)-N-ethylcarbamoyl)-1-hydroxymethyl]penicillanate; 40 mg.; ir (KBr) 1749 cm$^{-1}$; $^1$H-nmr (D$_2$O) delta (300 MHz), reflecting two amide rotamers in 1:2 ratio, 1.08 (3H, complex), 1.23 (3H, t), 1.46 (3H, s), 1.57 (1H, s), 1.62 (2H, s), 3.20 (3H, complex), 3.38 (1H, q), 3.59 (2H, complex), 3.9–4.1 (3H, complex), 4.21 (0.33H, s), 4.24 (0.67H, s), 4.26 (1H, q), 4.98 (1H, d, J=10 Hz), 5.40 (0.67H, d, J=4 Hz), 5.42 (0.33H, d, J=4 Hz); product of Example C66 (0.13 g.).

E89. Sodium 6-beta-[S-1-(N-(N-propylcarbamoylmethyl)-N-benzylcarbamoyl)-1-hydroxymethyl]penicillanate; 90 mg; ir (KBr) 1750 cm$^{-1}$; $^1$H-nmr (D$_2$O) delta (300 MHz), reflecting the two amide rotamers in 2:3 ratio, 0.84 (3H, overlapping triplets), 1.42 (2H, complex), 1.47 (1.8H, s), 1.49 (3H, s), 1.61 (1.2H, s), 3.0–3.2 (2H, complex), 3.8–4.3 (4H, complex), 4.5–5.1 (3H, complex), 5.46 (0.6H, d, J=4 Hz), 5.49 (0.4H, d, J=4 Hz), 7.2–7.5 (5H, arom.); product of Example C67 (0.32 g.).

E90. Sodium 6-beta-[S-1-(2-(N-ethylcarbamoyl)pyrrolidino)carbonyl]-1-hydroxymethyl]penicillanate; 120 mg; ir (KBr) 1756 cm$^{-1}$; $^1$H-nmr (D$_2$O) delta (300 MHz), reflecting two amide rotamers in 1:5 ratio, 1.08 (3H, t), 1.47 (3H, s), 1.61 (0.5H, s), 1.63 (2.5H, s), 1.8–2.1 (3H, complex), 2.2–2.3 (1H, complex), 3.1–3.3 (2H, complex), 3.5–3.7 (2H, complex), 3.97 (1H, dd, J=4 Hz, 10 Hz), 4.26 (1H, s), 4.32 (1H, m), 4.64 (0.17H, d), 4.87 (0.83H, d, J=10 Hz), 5.40 (0.83H, d, J=4 Hz), 5.43 (0.17H, d, J=4 Hz); product of Example C68 (225 mg.).

E91. Sodium 6-beta-[S-1-[N-(N-(2-methylpropyl)carbamoylmethyl)-N-(2-methylpropyl)carbamoyl]-1-hydroxymethyl]penicillanate; 60 mg.; ir (KBr) 1754 cm$^{-1}$; $^1$H-nmr (D$_2$O) delta (300 MHz), reflecting two amide rotamers in 1:1 ratio, 0.88 (9H, d), 0.9–1.0 (3H, complex), 1.48 (3H, s), 1.60 (1.5H, s), 1.62 (1.5H, s), 1.7–2.1 (2H, complex), 2.9–3.1 (2H, complex), 3.2–3.4 (1.5H, complex), 3.5–3.6 (0.5H, complex), 4.0–4.2 (2H, complex), 4.22 (0.5H, s), 4.26 (0.5H, s), 4.35 (1H, q), 4.80 (0.5H, d), 4.95 (0.5H, d), 5.44 (1H, m); product of Example C69 (0.12 g.).

E92. Sodium 6-beta-[S-1-(N-(2-morpholinoethyl)-N-ethylcarbamoyl)-1-hydroxymethyl]penicillanate; 50 mg.; $^1$H-nmr (D$_2$O) delta (300 MHz), reflecting two amide rotamers in about 1:2 ratio, 1.09 (1H, t), 1.25 (2H, t), 1.45 (3H, s), 1.61 (3H, s), 2.0–3.1 (6H, complex), 3.2–4.0 (9H, complex), 4.24 (1H, s), 4.8–5.0 (1H, complex), 5.41 (1H, complex); product of Example C70 (0.11 g.). E93. Sodium 6-beta-[S-1-[N-(R-alpha-methylbenzyl)carbamoyl]-1-hydroxymethyl]penicillanate; 0.13 g.; $^1$H-nmr (D$_2$O) delta (300 MHz), 1.44 (3H, s), 1.46 (3H, d), 1.60 (3H, s), 3.81 (1H, dd, J=4 Hz, 10 Hz), 4.20 (1H, s), 4.66 (1H, d, J=10 Hz), 4.91 (1H, q, J=8 Hz), 5.34 (1H, d, J=4 Hz), 7.3–7.4 (5H, m); product of Example C71 (0.23 g.)

E94. Sodium 6-beta-[S-1-[N-(S-alpha-methylbenzyl)-carbamoyl]-1-hydroxymethyl]penicillanate; 0.115 g.; $^1$H-nmr (D$_2$O) delta (300 MHz) 1.44 (3H, s), 1.47 (3H, d, J=6 Hz), 3.88 (1H, dd, J=4 Hz, 10 Hz), 4.20 (1H, s), 4.62 (1H, d, J=10 Hz), 4.91 (1H, q), 5.37 (1H, d, J=4 Hz), 7.3–7.4 (5H, complex); product of Example C72 (0.18 g.).

E95. Sodium 6-beta-[S-1-(N-benzhydrylcarbamoyl)-1-hydroxymethyl]penicillanate; initially isolated as the free acid from the aqueous residue following THF stripping, by acidification to pH 5.5 with 1N HCl, extraction into ethyl acetate, drying over Na$_2$SO$_4$, and stripping, 0.16 g.; converted to the sodium salt by dissolving in 10 ml. H$_2$O, adjusting to pH 6.0 with 1N NaOH and freeze drying, 0.16 g.; $^1$H-nmr (D$_2$O) delta (300 MHz), 1.43 (3H, s), 1.58 (3H, s), 3.85 (1H, dd, J=4 Hz, J=10 Hz), 4.15 (1H, s), 4.65 (1H, d, J=10 Hz), 5.30 (1H, d, J=4 Hz), 5.98 (1H, s), 7.1–7.3 (10H, complex); product of Example C73 (0.23 g.).

E96. Sodium 6-beta-[S-1-(N-[N-(2-morpholinoethyl)-carbamoylmethyl]-N-benzylcarbamoyl)-1-hydroxymethyl]penicillanate; 0.164 g.; ir (KBr) 1754 cm$^{-1}$; $^1$H-nmr (D$_2$O) delta (300 MHz), reflecting two amide rotamers in about 1:2 ratio, 1.46 (2H, s), 1.49 (1H, s), 1.50 (2H, s), 1.62 (1H, s), 3.0–3.3 (6H, complex), 3.5–3.6 (2H, complex), 3.9–4.1 (6H, complex), 4.22 (0.67H, s), 4.30 (0.33H, s), 4.46 (0.33H, d, J=15 Hz), 4.9–5.0 (1H, complex), 5.02 (0.67H, d, J=10 Hz), 5.44 (0.67H, d, J=4 Hz), 5.47 (0.33H, d, J=4 Hz), 7.2–7.5 (5H, complex); product of Example C74 (0.23 g.).

E97. Sodium 6-beta-[S-1-(S-2-(N,N-dimethylcarbamoyl)pyrrolidinocarbonyl)-1-hydroxymethyl]penicillanate; 0.18 g.; ir (KBr) 1753 cm$^{-1}$; $^1$H-nmr (D$_2$O) delta (300 MHz), reflecting amide rotamers in about 1:5 ratio, 1.60 (3H, s), 1.76 (3H, s), 1.9–2.0 (1H, multiplet), 2.1–2.2 (2H, complex), 2.4–2.5 (1H, multiplet), 3.04 (3H, s), 3.26 (3H, s), 3.7–4.0 (3H, complex), 4.1 (1H, dd, J=4 Hz, 10 Hz), 4.36 (1H, s), 5.00 (1H, d, J=10 Hz), 5.49 (1H, d, J=4 Hz); product of Example C75 (0.33 g.).

E98. Sodium 6-beta-[S-1-(1,4-diazabicyclo[3.2.2]non-4-ylcarbonyl)-1-hydroxymethyl]penicillanate; 0.050 g.; ir (KBr) 1751 cm$^{-1}$; $^1$H-nmr (D$_2$O) delta (300 MHz), reflecting amide rotamers in about 1:3 ratio, 1.46 (3H, s), 1.80 (3H, s), 2.0–2.4 (4H, complex), 3.4–3.6 (8H, complex), 3.97 (0.75H, dd, J=4 Hz, 10 Hz), 4.01 (0.25H, dd, J=4 Hz, 10 Hz), 4.1 (2H, complex), 4.23 (1H, s), 4.95 (0.25H, d, J=10 Hz), 4.96 (0.75H, d, J=10 Hz), 5.41 (0.25H, d, J=4 Hz), 5.44 (0.75H, d, J=4 Hz); product of Examplee C76 (0.11 g.).

E99. Sodium 6-beta-[S-1-(S-2-(pyrrolidinocarbonyl)pyrrolidinocarbonyl)-1-hydroxymethyl]penicillanate; 0.18 g.; ir (KBr) 1763 cm$^-$; $^1$H-nmr (D$_2$O) delta (300 MHz), predominantly a single amide rotamer, 1.46 (3H, s), 1.62 (3H, s), 1.8–2.4 (8H, complex), 3.3–3.9 (6H, complex), 3.95 (1H, dd, J=4 Hz, 10 Hz), 4.22 (1H, s), 4.62 (1H, m), 4.85 (1H, d, J=10 Hz), 5.34 (1H, d, H=4 Hz); product of Example C77 (0.32 g.).

E100. Sodium 6-beta-[S-1-(N-methyl-N-(4-hydroxyphenyl)carbamoyl)-1-hydroxymethyl]penicillanate; 0.075 g.; $^1$H-nmr (D$_2$O) delta (300 MHz), 1.46 (3H, s), 1.61 (3H, s), 2.70 (3H, s), 4.09 (1H, dd, J=4 Hz, 10 Hz), 4.22 (1H, s), 4.96 (1H, d, J=10 Hz), 5.50 (1H, d, J=4 Hz), 6.88 (4H, ABq); product of Example C78 (0.21 g.).

E101. Sodium 6-beta-[S-1-[N-(R-alpha-methylbenzyl)carbamoyl]-1-hydroxymethyl]penicillanate 1,1-dioxide; 0.054 g.; $^1$H-nmr (D$_2$O) delta (300 MHz), 1.34 (3H, s), 1.44 (3H, d, J=8 Hz), 1.50 (3H, s), 3.94 (1H, dd, J=5 Hz, 11 Hz), 4.20 (1H, s), 4.88 (1H, d, J=Hz), 4.93 (1H, q, J=8 Hz), 5.10 (1H, d, J=11 Hz), 7.2–0.74 (5H, complex); product of Example D15 (0.11 g.).

MISCELLANEOUS REACTIONS

EXAMPLE F1

Pivaloyloxymethyl 6-beta-[S-1-(1,2,3,4-tetrahydroisoquinolino)carbonyl-1-hydroxymethyl]penicillanate The title product of Example E16 (0.245 g., 0.59 mmol) was dissolved in 1 ml. DMF and cooled to 0° C. Chloromethyl pivalate (0.086 ml., 0.089 g., 0.59 mmol) was added and the mixture stirred for 18 hours at room temperature, then equilibrated with 10 ml. H$_2$O and 10 ml. ether. The organic layer was separated and filtered (yielding 50 mg. of solids). The aqueous layer was extracted with 2×10 ml. of ether, and the filtered organic layer and ether extracts combined, washed 1×10 ml. H$_2$O and 1×10 ml. brine, dried over Na$_2$SO$_4$ and stripped to a foam, 90 mg., which tlc indicated to be incompletely esterified. The solids and the foam were redissolved in 1 ml. of fresh DMF and cooled to 0° C. Diisopropylethylamine (0.053 ml., 0.039 g.) and then chloromethyl pivalate (0.049 ml., 0.051 g.) were added and the mixture stirred 18 hours at room temperature, then isolated according to the procedure above (in this case, no product precipitated from the initial ether layer) to yield an oil, 0.24 g., which was chromatographed on 10 g. silica gel using 1:3 ethyl acetate:CHCl$_3$ as eluant to produce purified title product as a foam, 0.11 g.; $^1$H-nmr (CDCl$_3$) delta (300 MHz), reflecting amide rotamers in about 2:3 ratio, 1.20 (9H, s), 1.44 (1.2H, s), 1.46 (1.8H, s), 1.61 (1.2H, s), 1.65 (1.8H, s), 2.8–3.0 (2H, complex), 3.6–3.8 (2H, complex), 3.85–4.00 (1H, complex), 4.05–4.15 (1H, complex), 4.44 (0.4H, s), 4.46 (0.6H, s), 4.7–5.0 (3H, complex), 5.54 (1H, m), 5.77 (1H, d), 5.87 (1H, d), 7.1–7.3 (4H, complex).

PREPARATION F1

Sodium Salt of Benzyl 6-beta-(S-1-Carboxy-1-hydroxymethyl)penicillanate

Title product of Preparation B1 (11.1 g., 0.0274 mol) was dissolved in 100 ml. CH$_2$Cl$_2$. Sodium 2-ethylhexanoate in ethyl acetate (0.5N, 54.8 ml., 0.0274 mol) and then Pd[(C$_6$H$_5$)$_3$P]$_4$ (0.4 g.) were added, the mixture was stirred 1 hour under N$_2$, diluted with 300 ml. ether, and filtered to yield instant title product, 10.1 g.; $^1$H-nmr (D$_2$O) delta (300 MHz): 1.37 (3H, s), 1.63 (3H, s), 3.86 (1H, dd, J=4 Hz, 10 Hz), 4.45 (1H, d, J=10 Hz), 4.62 (1H, s), 5.28 (2H, ABq), 5.51 (1H, d, J=4 Hz), 7.5 (5H, s).

PREPARATION F2

Sodium Salt of Benzyl 6-beta-(R-1-Carboxy-1-hydroxymethyl)penicillanate

By the method of the preceding Preparation, title product of Preparation B2 (5.48 g., 0.0135 mol) was converted to instant title product, 3.85 g.; $^1$H-nmr (D$_2$O) delta (300 MHz): 1.38 (3H, s), 1.65 (3H, s), 4.05 (1H, dd, J=4 Hz, 8 Hz), 4.44 (1H, d, J=10 Hz), 4.61 (1H, s), 5.28 (2H, ABq), 5.49 (1H, d, J=4 Hz), 7.50 (5H, s).

The cyclic anhydrides employed in the preceding Examples were isolated and characterized as follows:

PEREPARATION F3

6-beta-(S-1,3-dioxolane-2,5-dion-4-yl)penicillanate

Title product of Preparation F1 (0.271 g., 0.7 mmol) was dissolved in 20 ml. dry THF and cooled to −15° C. COCl$_2$ in CCl$_4$ (0.7N, 1.5 ml., 1.05 mmols) was added. After 1 minute, solvent was stripped to produce a near quantitative yield of instant title product as a dry foam, ir (CHCl$_3$) 1900, 1820 and 1780 cm$^{-1}$; $^1$H-nmr (CDCl$_3$) delta (300 MHz): 1.44 (3H, s), 1.68 (3H, s), 4.24 (1H, overlapping doublets), 4.56 (1H, s), 5.22 (2H, s), 5.46 (1H, d, J=5 Hz), 5.59 (1H, d, J=4 Hz), 7.40 (5H, s).

PREPARATION F4

6-beta-(R-1,3-dioxolane-2,5-dion-4-yl)penicillanate

By the procedure of the preceding Preparation, R-title product of Preparation F2 (0.271 g., 0.7 mmol) was converted to instant title product, again in quantitative yield; ir (CHCl$_3$) 1900, 1817 and 1780 cm$^{-1}$; $^1$H-nmr (CDCl$_3$) delta (300 MHz): 1.44 (3H, s), 1.67 (3H, s), 4.27 acyloxymethyl or 1-(acyloxy)ethyl radical derived from a conventional beta-lactam antibiotic; and R$^1$ and R$^2$ are taken separately and are each independently hydrogen, (C$_1$–C$_7$)alkyl, phenyl, (C$_7$–C$_{12}$)-phenylalkyl, (C$_3$–C$_7$)cycloalkyl, naphthyl, or

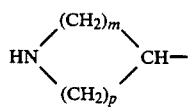

where m is 1 or 2 and p is 1, 2 or 3; or one of said groups substituted on aliphatic, aromatic or heterocyclic carbon with (C$_1$–C$_4$)alkyl, phenyl, hydroxy, hydroxymethyl, 2-hydroxyethyl, (C$_1$–C$_4$)alkoxy, (C$_2$–C$_5$)alkanoyloxy, carbamoyloxy, formamido, (C$_2$–C$_5$)alkanecarboxamido, (C$_1$–C$_4$)alkanesulfonamido,

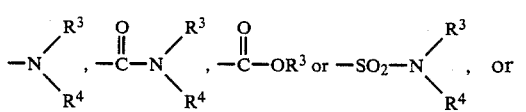

on heterocyclic nitrogen with (C$_1$–C$_4$)alkyl, phenyl, (C$_7$–C$_9$)phenylalkyl, pyridyl, 2-hydroxyethyl, formyl, (C$_2$–C$_5$)alkanoyl; or

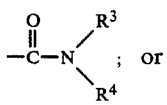

R$^1$ and R$^2$ are taken together with the nitrogen to which they are attached to form a pyrrolidine, piperidine, perhydroazepine, morpholine, piperazine, homopiperazine, indoline, isoindoline, 1,2,3,4-tetrahydroquinoline, 1,2,3,4-tetrahydroisoquinoline or

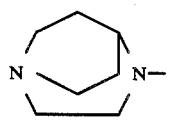

ring system; or one of said ring systems substituted on aliphatic, aromatic or heterocyclic carbon with (C$_1$–C$_4$)alkyl, phenyl, hydroxy, hydroxymethyl, 2-hydroxyethyl, (C$_1$–C$_4$)alkoxy, (C$_2$–C$_5$)alkanoyloxy, carbamoyloxy, formamido, (C$_2$–C$_5$)alkanecarboxamido, (C$_1$–C$_4$)alkanesulfonamido,

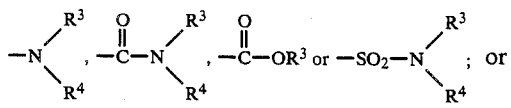

on heterocyclic nitrogen with (C$_1$–C$_4$)alkyl, phenyl, (C$_7$–C$_9$)phenylalkyl, pyridyl, 2-hydroxyethyl, formyl, (C$_2$–C$_5$)alkanoyl; or

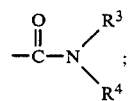

R$^3$ and R$^4$ are taken separately and are each hydrogen, (C$_1$–C$_4$)alkyl or phenyl; or R$^3$ and R$^4$ are taken together with the nitrogen to which they are attached to form a pyrrolidine, piperidine, morpholine, or 4-[(C$_1$–C$_3$)alkyl or phenyl]piperazine ring; with the provisos that in said group —NR$^1$R$^2$ (a) there is no tetrahedral carbon atom which is simultaneously bonded to two of the same or different atoms selected from the group consisting of nitrogen, oxygen or sulfur and (b) when both of R$^1$ and R$^2$ are other than hydrogen, then the carbons of R$^1$ and R$^2$ which are adjacent to the nitrogen branch point are substituted with a total of at least two hydrogens;

a pharmaceutically acceptable cationic salt when the compound contains a carboxylic acid group; or a pharmaceutically acceptable acid addition salt when the compound contains a basic nitrogen atom.

2. A compound of claim 1 wherein R is hydrogen.

3. A compound of claim 1 wherein R$^1$ and R$^2$ are taken separately and are each independently hydrogen, (C$_1$–C$_4$)alkyl, (C$_5$–C$_6$)cycloalkyl, phenyl, benzyl or one of said groups substituted by methyl, hydroxy, (C$_1$–C$_2$)alkoxy, —COOR$^3$, or —CONR$^3$R$^4$.

4. A compound of claim 3 wherein the C-1 hydroxy substituted carbon of the side chain is in the S-configuration.

5. A compound of claim 3 wherein R is hydrogen.

6. A compound of claim 4 wherein R is hydrogen.

7. A compound of claim 3 wherein n is 0.

8. A compound of claim 5 wherein n is 0.

9. A compound of claim 6 wherein n is 0.

10. The compound of claim 9 wherein R$^1$ and R$^2$ are each methyl.

11. The compound of claim 9 wherein R$^1$ is methyl and R$^2$ is benzyl.

12. The compound of claim 9 wherein R$^1$ is methyl and R$^2$ is phenyl.

13. The compound of claim 9 wherein R$^1$ is benzyl and R$^2$ is —CH$_2$CONHCH$_3$.

14. The compound of claim 9 wherein R$^1$ is ethyl and R$^2$ is 3-hydroxyphenyl.

15. A compound of claim 6 wherein n is 1.

16. The compound of claim 15 wherein R$^1$ and R$^2$ are each methyl and the 1-oxide is in the beta-configuration.

17. A compound of claim 6 wherein n is 2.

18. The compound of claim 17 wherein R$^1$ and R$^2$ are each methyl.

19. The compound of claim 17 wherein R$^1$ is methyl and R$^2$ is phenyl.

20. The compound of claim 17 wherein R$^1$ is methyl and R$^2$ is cyclohexyl.

21. A compound of claim 1 wherein R$^1$ and R$^2$ are taken together with the nitrogen to which they are attached to form a pyrrolidine, piperidine, perhydroazepine, morpholine, 4-[formyl, (C$_1$–C$_4$)alkyl, phenyl, benzyl, pyridyl or 2-hydroxyethyl]piperazine, indoline, isoindoline, 1,2,3,4-tetrahydroquinoline or 1,2,3,4-tetrahydroisoquinoline ring system, or one of said ring systems substituted by methyl, hydroxy, hydroxy- (1H, overlapping doublets), 4.57 (1H, s), 5.21 (2H, s), 5.56 (2H, complex), 7.40 (5H, s).

PREPARATION F5

Diallyl Tartarate

Tartaric acid (450 g., 3.0 mols) was slurried in 600 ml. DMF and cooled to 0°–5° C. in an ice bath. Triethylamine (835 ml., 6.0 mols) was added and the resulting solution recooled to 0°–5° C. Allyl bromide (519 ml., 6.0 mols) was then added. An exotherm was noted. The resulting slurry was stirred at room temperature and by-product triethylamine hydrobromide recovered by filtration. The filtrate was diluted with 1.5 l. of ethyl acetate, washed 3×300 ml. $H_2O$, dried over $Na_2SO_4$ and stripped to yield title product as an oil, 434 g.; $^1$H-nmr (CDCl$_3$) delta 3.42 (2H, br.s), 4.5–4.8 (6H, complex), 5.0–5.4 (4H, complex), 5.6–6.2 (2H, complex).

PREPARATION F6

Allyl 2-Methoxy-2-hydroxyacetate

(Allyl Glyoxylate Methyl Acetal)

The product of the preceding Preparation (161 g., 0.74 mol) was dissolved in a mixture of 133 ml. acetic acid and 800 ml. $H_2O$, stirred and cooled to 0°–5° C. A slurry of NaIO$_4$ (157.3 g., 0.74 mol) in 700 ml. $H_2O$ was added over a 10 minute period. The resulting solution was stirred at 0°–5° C., a heavy precipitate beginning to form after 30 minutes. After 1 hour, the mixture was filtered. The cake was washed with 1 l. ethyl acetate and the wash liquor combined with the filtrate. The aqueous layer was separated and washed 3×800 ml. fresh ethyl acetate. The organic layer and three extracts were combined and stripped, the residue taken up in 1 l. ether and washed 2×300 ml. $H_2O$. The latter $H_2O$ extracts were combined and extracted with 300 ml. ethyl acetate. The combined ether layer and ethyl acetate extract were stripped to yield allyl 2,2-dihydroxyacetate (allyl glyoxylate hydrate) as an oil. The hydrate was dissolved in 1 l. CH$_3$OH and stripped, and the process repeated several times, to yield the present hemiacetal product as an oil, 148 g.; $^1$H-nmr (CDCl$_3$) delta 3.45 (3H, s), 4.6–6.3 (6H, complex).

PREPARATION F7

Allyl Glyoxalate

The product of the preceding Preparation (105 g.) was heated at 65° C. under vacuum (0.8 mm) under a reflux condenser for 20 hours, then vacuum distilled and redistilled to yield present title product, 37 g., $^1$H-nmr (CDCl$_3$) delta 4.60 (2H, d), 5.0–5.4 (2H, complex), 5.5–6.2 (1H, m), 9.34 (1H, s).

PREPARATION F8

Tartaric Acid bis-Pyrrolidine Amide

Pyrrolidine (61 ml., 0.73 mol) and diethyl tartrate (50 ml., 0.29 mol) were stirred for 5 minutes and then allowed to stand for 3 days. The resulting solid mass was broken up by the addition of an equal volume of ethyl acetate and title product recovered by filtration, 54 g., mp 132°–134° C.; $^1$H-nmr (CDCl$_3$) delta (ppm) 1.7–2.1 (8H, complex), 3.3–3.7 (8H, complex), 4.2–4.6 (4H, complex).

Other amines were reacted with diethyl tartarate to form bis-tartrate amides useful in the present syntheses. Dimethylamine reacted more rapidly than pyrrolidine, while other secondary amines reacted more slowly.

PREPARATION F9

N-Glyoxyloylpyrrolidine

Title product of the preceding Preparation (20 g., 0.08 mol) was dissolved in 200 ml. benzene. Lead tetraacetate (95%, 36.4 g., 0.08 mol) was added slowly. After stirring for 1 hour, by-products were removed by filtration, the filtrate stripped and the residue distilled at 0.15 mm. from a bath at 100°–125° C. Title product was collected in three fractions, 11.87 g.; $^1$H-nmr (CDCl$_3$) delta (ppm) 1.8–2.2 (4H, complex), 3.4–3.9 (4H, complex), 9.37 (1H, s). The material was used in further processing within a few hours.

PREPARATION F10

N-Isopropylglyoxylamide

By the method of the preceding Preparation, tartaroyl bis-(N-isopropylamide) (20 g., 0.086 mol) was converted to title product, 12.2 g.; bp 70°–72° 2 mm; $^1$H-nmr (CDCl$_3$) delta (ppm) 1.24 (6H, d, J=7 Hz), 4.00 (1H, m), 9.24 (1H, s).

PREPARATION F11

N-Glyoxyloylmorpholine

By the method of Preparation F9, tartaric acid bis-morpholine amide (11.45 g., 0.04 mol) was converted to title product. The residue was distilled at 1.5 mm from a bath at 120°–130°, collecting title product in two fractions (4.74 g.), used immediately in further processing; $^1$H-nmr (CDCl$_3$) delta (ppm) 3.5–3.9 (8H, complex), 9.43 (1H, s).

PREPARATION F12

N-Glyoxyloylpiperidine

By the method of Preparation F9, tartaric acid bis-piperidine amide (20.6 g., 0.072 mol) was converted to title product. The residue was distilled at 1.1 mm. from a bath at 110°–130°, collecting title product in 3 fractions, 13.74 g.; $^1$H-nmr (CDCl$_3$) delta (ppm) 1.4–1.8 (6H, complex), 3.3–3.8 (4H, complex), 9.55 (1H, s).

PREPARATION F13

N,N-Dimethylglyoxylamide

Tartaroyl bis-(dimethylamide) (30 g., 0.15 mol) was converted to title product by the method of Preparation F9. The residue was distilled from a bath at 70° at a pressure from 1.5 to 0.8 mm. The initial fraction (about 5–7 ml.) was discarded. The second and third fractions (11 and 7 g., respectively) represented good quality title product; $^1$H-nmr (CDCl$_3$) delta (ppm) 3.05 (3H, s), 3.23 (3H, s), 9.46 (1H, s).

I claim:
1. A compound having the formula

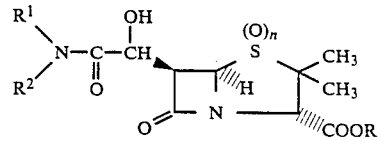

wherein
n is 0, 1 or 2;
R is hydrogen, a radical group forming an ester hydrolyzable under physiological conditions, or an methyl, carboxy, carbamoyl, —COOR³ or —CONR³R⁴.

22. A compound of claim 21 wherein the C-1 hydroxy substituted carbon of the side chain is in the S-configuration.

23. A compound of claim 21 wherein R is hydrogen.

24. A compound of claim 22 wherein R is hydrogen.

25. A compound of claim 21 wherein n is 0.

26. A compound of claim 23 wherein n is 0.

27. A compound of claim 24 wherein n is 0.

28. The compound of claim 27 wherein R¹R²N— is perhydroazepino.

29. The compound of claim 27 wherein R¹R²N— is 1,2,3,4-tetrahydroisoquinolino.

30. The compound of claim 27 wherein R¹R²N— is isoindolino.

31. The compound of claim 27 wherein R¹R²N— is indolino.

32. The compound of claim 27 wherein R¹R²N— is piperidino.

33. A compound of claim 24 wherein n is 1.

34. The compound of claim 33 wherein R¹R²N— is pyrrolidine and the 1-oxide is in the alpha configuration.

35. A compound of claim 24 wherein n is 2.

36. The compound of claim 35 wherein R¹R²N— is piperidino.

37. The compound of claim 35 wherein R¹R²N— is 4-hydroxypiperidino.

38. The compound of claim 35 wherein R¹R²N— is 4-phenylpiperidino.

39. A compound of claim 1 wherein R is a radical group forming an ester hydrolyzable under physiological conditions.

40. A compound of claim 4 wherein R is a radical group forming an ester hydrolyzable under physiological conditions.

41. A compound of claim 40 wherein R is:
(5-methyl-1,3-dioxol-2-on-4-yl)methyl;
1H-isobenzofuran-3-on-1-yl;
gamma-butyrolacton-4-yl;
—CHR⁵OCOR⁶; or
—CHR⁵OCOOR⁷;
wherein R⁵ is hydrogen or methyl; R⁶ is ($C_1$-$C_6$)alkyl, ($C_1$-$C_6$)carboxyalkyl, carboxycyclohexyl or carboxyphenyl; and R⁷ is ($C_1$-$C_6$)alkyl.

42. A compound of claim 41 wherein R is 1-(ethoxycarbonyloxy)ethyl or pivaloyloxymethyl.

43. A compound of claim 22 wherein R is a radical group forming an ester hydrolyzable under physiological conditions.

44. A compound of claim 43 wherein R is:
(5-methyl-1,3-dioxol-2-on-4-yl)methyl;
1H-isobenzofuran-3-on-1-yl;
gamma-butyrolacton-4-yl;
—CHR⁵OCOR⁶; or
—CHR⁵OCOOR⁷;
wherein R⁵ is hydrogen or methyl; R⁶ is ($C_1$-$C_6$)alkyl, ($C_1$-$C_6$)carboxyalkyl, carboxycyclohexyl or carboxyphenyl; and R⁷ is ($C_1$-$C_6$)alkyl.

45. A compound of claim 44 wherein R is 1-(ethoxycarbonyloxy)ethyl or pivaloyloxymethyl.

46. A compound of claim 1 wherein R is an acyloxymethyl radical derived from a conventional beta-lactam antibiotic.

47. A compound of claim 4 wherein R is an acyloxymethyl radical derived from a conventional beta-lactam antibiotic.

48. A compound of claim 47 wherein R is an acyloxymethyl radical of the formula

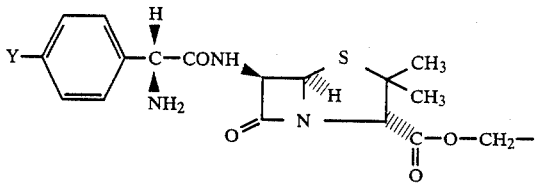

wherein Y is hydrogen or hydroxy.

49. A compound of claim 48 wherein Y is hydrogen.

50. A compound of claim 22 wherein R is an acyloxymethyl radical derived from a conventional beta-lactam antibiotic.

51. A compound of claim 50 wherein R¹ is an acyloxymethyl radical of the formula

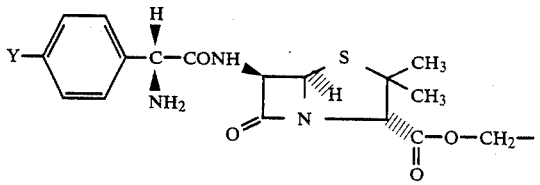

wherein Y is hydrogen or hydroxy.

52. A compound of claim 51 wherein Y is hydrogen.

53. A pharmaceutical composition comprising an antibacterially effective amount of a compound of claim 1 and a pharmaceutically acceptable carrier or diluent.

54. A pharmaceutical composition comprising an antibacterially effective amount of a compound of claim 3 and a pharmaceutically acceptable carrier or diluent.

55. A pharmaceutical composition comprising an antibacterially effective amount of a compound of claim 6 and a pharmaceutically acceptable carrier or diluent.

56. A pharmaceutical composition comprising an antibacterially effective amount of a compound of claim 21 and a pharmaceutically acceptable carrier or diluent.

57. A pharmaceutical composition comprising an antibacterially effective amount of a compound of claim 24 and a pharmaceutically acceptable carrier or diluent.

58. A method of treating a bacterial infection in a mammal which comprises administerint to said mammal an antibacterially effective amount of a compound of claim 1.

59. A method of treating a bacterial infection in a mammal which comprises administering to said mammal an antibacterially effective amount of a compound of claim 3.

60. A method of treating a bacterial infection in a mammal which comprises administering to said mammal an antibacterially effective amount of a compound of claim 6.

61. A method of treating a bacterial infection in a mammal which comprises administering to said mammal an antibacterially effective amount of a compound of claim 21.

62. A method of treating a bacterial infection in a mammal which comprises administering to said mammal an antibacterially effective amount of a compound of claim 24.

63. A pharmaceutical composition for treating bacterial infections which comprises, in a weight ratio of 10:1 to 1:3, a conventional beta-lactam antibiotic and a compound of claim 1 wherein R is hydrogen or a radical group forming an ester which is hydrolyzable under physiological conditions.

64. A pharmaceutical composition for treating bacterial infections which comprises, in a weight ratio of 10:1 to 1:3, a conventional beta-lactam antibiotic and a compound of claim 3 wherein R is hydrogen or a radical group forming an ester which is hydrolyzable under physiological conditions.

65. A pharmaceutical composition for treating bacterial infections which comprises in a weight ratio of 10:1 to 1:3, a conventional beta-lactam antibiotic and a compound of claim 6.

66. A pharmaceutical composition of claim 65 wherein the beta-lactam antibiotic is
amoxicillin,
ampicillin,
apalcillin,
azlocillin,
aztreonam,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefbuperazone,
cefmenoxime,
cefonicid,
cefodizime,
cefoperazone,
ceforanide,
cefotaxime,
cefotiam,
cefoxitin,
cefpimazole
cefpiramide,
cefpirome,
cefsulodin,
ceftazidime,
ceftizoxime,
ceftriaxone,
cefuroxime,
cephacetrile,
cephalexin,
cephaloglycin,
cephaloridine,
cephalothin,
cephapirin,
cepharadine,
cyclacillin,
epicillin,
furazlocillin
hetacillin,
lenampicillin,
levopropylcillin,
mecillinam,
mezlocillin,
penicillin G,
penicillin V,
phenethicillin,,
piperacillin,
pivampicillin,
sarmoxicillin,
sarpicillin,
suncillin,
talampicillin,
ticarcillin; or
7-[D-(2-[4-carboxy-5-imidazolecarboxamido])-2-phenylacetamido]-3-[4-sulfonatoethyl)pyridinium]-3-cephem-4-carboxylic acid;
or a pharmaceutically-acceptable salt of one of said beta-lactam antibiotics.

67. A pharmaceutical composition for treating bacterial infections which comprises, in a weight ratio of 10:1 to 1:3, a conventional beta-lactam antibiotic and a compound of claim 21 wherein R is hydrogen or a radical group forming an ester which is hydrolyzable under physiological conditions.

68. A pharmaceutical composition for treating bacterial infections which comprises in a weight ratio of 10:1 to 1:3, a conventional beta-lactam antibiotic and a compound of claim 24 wherein R is hydrogen or a radical group forming an ester which is hydrolyzable under physiological conditions.

69. A pharmaceutical composition of claim 68 wherein the beta-lactam antibiotic is
amoxicillin,
ampicillin,
apalcillin,
azlocillin,
aztreonam,
bacampicillin,
carbenicillin,
carbenicillin indanyl,
carbenicillin phenyl,
cefaclor,
cefadroxil,
cefaloram,
cefamandole,
cefamandole nafate,
cefaparole,
cefatrizine,
cefazolin,
cefbuperazone,
cefmenoxime,
cefonicid,
cefodizime,
cefoperazone,
ceforanide,
cefotaxime,
cefotiam,
cefoxitin,
cefpimiazole,
cefpiramide,
cefpirome,
cefsulodin,
ceftazidime,
ceftizoxime,
ceftriaxone,
cefuroxime,
cephacetrile,
cephalexin,
cephaloglycin,
cephaloridine,
cephalothin,
cephapirin,
cephradine,
cyclacillin,
epicillin, furazlocillin
hetacillin,
lenampicillin,
levopropylcillin,
mecillinam,
mezlocillin,
penicillin G,
penicillin V,
phenethicillin,,
piperacillin,
pivampicillin,
sarmoxicillin,
sarpicillin,
suncillin,
talampicillin,
ticarcillin; or
7-[D-(2-[4-carboxy-5-imidazolecarboxamido])-2-phenylacetamido]-3-[4-sulfonatoethyl)pyridinium]-3-cephem-4-carboxylic acid;
or a pharmaceutically-acceptable salt of one of said beta-lactam antibiotics.

70. A method of treating a bacterial infection in a mammal which comprises administering to said mammal an antibacterially effective amount of a pharmaceutical composition of claim 63.

71. A method of treating a bacterial infection in a mammal which comprises administering to said mammal an antibacterially effective amount of a pharmaceutical composition of claim 64.

72. A method of treating a bacterial infection in a mammal which comprises administering to said mammal an antibacterially effective amount of a pharmaceutical composition of claim 65.

73. A method of treating a bacterial infection in a mammal which comprises adminstering to said mammal an antibacterially effective amount of a pharmaceutical composition of claim 66.

74. A method of treating a bacterial infection in a mammal which comprises administering to said mammal an antibacterial effective amount of a pharmaceutical composition of claim 67.

75. A method of treating a bacterial infection in a mammal which comprises administering to said mammal an antibacterially effective amount of a pharmaceutical composition of claim 68.

76. A method of treating a bacterial infection in a mammal which comprises administering to said mammal an antibacterially effective amount of a pharmaceutical composition of claim 69.

77. A compound having the formula

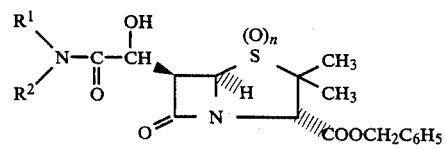

wherein
n is 0, 1 or 2; and
$R^1$ and $R^2$ are taken separately and are each independently hydrogen, $(C_1-C_7)$alkyl, phenyl, $(C_7-C_{12})$phenylalkyl, $(C_3-C_7)$cycloalkyl, naphthyl, or

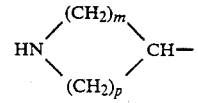

where m is 1 or 2 and p is 2 or 3; or one of said groups substituted on aliphatic, aromatic or heterocyclic carbon with $(C_1-C_4)$alkyl, phenyl, hydroxy, hydroxymethyl, 2-hydroxyethyl, $(C_1-C_4)$alkoxy, $(C_2-C_5)$alkanoyloxy, carbamoyloxy, formamido, $(C_2-C_5)$alkylcarboxamido, $(C_1-C_4)$alkylsulfonamido,

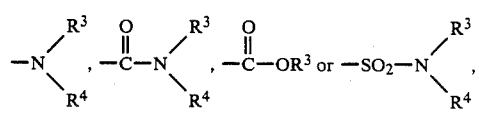

on heterocyclic nitrogen with $(C_1-C_4)$alkyl, phenyl, $(C_7-C_9)$phenylalkyl, pyridyl, 2-hydroxyethyl, formyl, $(C_2-C_5)$alkanoyl, or

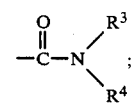

or
$R^1$ and $R^2$ are taken together with the nitrogen to which they are attached to form a pyrrolidine, piperidine, perhydroazepine, morpholine, piperazine, homopiperazine, indoline, isoindoline, 1,2,3,4-tetrahydroquinoline, 1,2,3,4-tetrahydroisoquinoline or

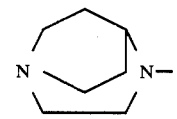

ring system; or one of said ring systems substituted on aliphatic, aromatic or heterocyclic carbon with $(C_1-C_4)$alkyl, hydroxy, hydroxymethyl, 2-hydroxyethyl, $(C_1-C_4)$alkoxy, $(C_2-C_5)$alkanoyloxy, carbamoyloxy, formamido, $(C_2-C_5)$alkylcarboxamido, $(C_1-C_4)$alkylsulfonamido,

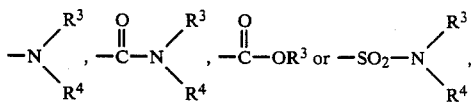

or
on heterocylic nitrogen with $(C_1-C_4)$alkyl, phenyl, $(C_7-C_9)$phenylalkyl, pyridyl, 2-hydroxyethyl, formyl, $(C_2-C_5)$alkanoyl, or

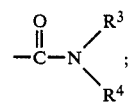

$R^3$ and $R^4$ are taken separately and are each hydrogen, $(C_1-C_4)$alkyl or phenyl; or $R^3$ and $R^4$ are taken together with the nitrogen to which they are attached to form a pyrrolidine, piperidine, morpholine, or 4-[($C_1$-$C_3$)alkyl or phenyl]piperazine ring; with the provisos (a) that said group —$NR^1R^2$ contains no tetrahedral carbon which is simultaneously bonded to two of the same or different atoms selected from the group consisting of nitrogen, oxygen and sulfur; (b) when both of $R^1$ and $R^2$ are other than hydrogen, then the carbons of $R^1$ and $R^2$ which are adjacent to the nitrogen branch point in said group —$NR^1R^2$ are substituted with a total of at least two hydrogens; and (c) that when said group —$NR^1R^2$ contains a substituent —NH or —$NH_2$ group which is more reactive towards cyclic anhydride than the $R^1R^2$NH group, said substituent —NH or —$NH_2$ group is protected by a benzyloxycarbonyl group.

78. A compound of claim 77 wherein substituent NH or $NH_2$ groups are protected by a benzyloxycarbonyl group, and substituent carboxy or phenolic hydroxy groups are protected by a benzyl group.

79. A compound of claim 77 wherein $R^1$ and $R^2$ are taken separately and are each independently hydrogen, ($C_1$-$C_4$)alkyl, ($C_5$-$C_6$)cycloalkyl, phenyl, benzyl or one of said groups substituted by methyl, hydroxy, ($C_1$-$C_2$)alkoxy, —$COOR^3$ or —$CONR^3R^4$.

80. A compound of claim 79 wherein carboxy or phenolic hydroxy groups are protected by a benzyl group.

81. A compound of claim 79 wherein the C-1 hydroxy substituted carbon of the side chain is in the S-configuration.

82. A compound of claim 80 wherein the C-1 hydroxy substituted carbon of the side chain is in the S-configuration.

83. A compound of claim 77 wherein $R^1$ and $R^2$ are taken together with the nitrogen to which they are attached to form a pyrrolidine, piperidine, perhydroazepine, morpholine, 4-[formyl, ($C_1$-$C_4$)alkyl, phenyl, benzyl, pyridyl or 2-hydroxyethyl]piperazine, indoline, isoindoline, 1,2,3,4-tetrahydroquinoline or 1,2,3,4-tetrahydroisoquinoline ring system, or one of said ring systems substituted by methyl, hydroxy, hydroxymethyl, carboxy, carbamoyl, —$COOR^3$ or —$CONR^3R^4$.

84. A compound of claim 83 wherein carboxy or phenolic hydroxy groups are protected by a benzyl group.

85. A compound of claim 83 wherein the C-1 hydroxy substituted carbon of the side chain is in the S-configuration.

86. a compound of claim 84 wherein the C-1 hydroxy substituted carbon of the side chain is in the S-configuration.

* * * * *